US008394510B2

(12) United States Patent
Mizuki et al.

(10) Patent No.: US 8,394,510 B2
(45) Date of Patent: Mar. 12, 2013

(54) AROMATIC AMINE DERIVATIVE AND ORGANIC ELECTROLUMINESCENCE DEVICE USING THE SAME

(75) Inventors: Yumiko Mizuki, Chiba (JP); Masahiro Kawamura, Chiba (JP); Nobuhiro Yabunouchi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 825 days.

(21) Appl. No.: 11/928,907

(22) Filed: Oct. 30, 2007

(65) Prior Publication Data
US 2008/0124572 A1 May 29, 2008

(30) Foreign Application Priority Data

Nov. 24, 2006 (JP) ................................. 2006-317093
Aug. 13, 2007 (JP) ................................. 2007-211117

(51) Int. Cl.
H01L 51/50 (2006.01)
C09K 11/08 (2006.01)
C07D 209/86 (2006.01)
C07D 403/02 (2006.01)
C07D 417/02 (2006.01)
C07D 409/02 (2006.01)
C07D 405/02 (2006.01)

(52) U.S. Cl. ........ 428/690; 428/917; 313/504; 313/506; 548/440; 548/159

(58) Field of Classification Search ........................ None
See application file for complete search history.

(56) References Cited

U.S. PATENT DOCUMENTS

| | | | | |
|---|---|---|---|---|
| 5,968,675 | A * | 10/1999 | Tamano et al. ............... | 428/690 |
| 7,998,596 | B2 * | 8/2011 | Yabunouchi et al. ......... | 428/690 |
| 2003/0219625 | A1 * | 11/2003 | Wolk et al. .................... | 428/690 |
| 2004/0151829 | A1 * | 8/2004 | Boroson et al. ............... | 427/64 |
| 2004/0219387 | A1 * | 11/2004 | Li et al. ......................... | 428/690 |
| 2005/0225235 | A1 * | 10/2005 | Kim et al. ..................... | 313/504 |
| 2006/0020136 | A1 | 1/2006 | Hwang et al. | |
| 2008/0268284 | A1 * | 10/2008 | Kawakami et al. ........... | 428/691 |
| 2010/0145067 | A1 | 6/2010 | Yokota et al. | |
| 2010/0194266 | A1 * | 8/2010 | Seo et al. ...................... | 313/503 |

FOREIGN PATENT DOCUMENTS

| | | | |
|---|---|---|---|
| JP | 63-014156 | * | 1/1988 |
| JP | 63-14156 | | 1/1988 |
| JP | 9-310066 | | 12/1997 |
| JP | 10-168447 | | 6/1998 |
| JP | 10-218887 | | 8/1998 |
| JP | 11-35532 | A | 2/1999 |
| JP | 11-292860 | | 10/1999 |
| JP | 2003-75955 | | 3/2003 |
| JP | 2005-68366 | | 3/2005 |
| JP | 2005-289914 | A * | 10/2005 |
| JP | 2005-290000 | A | 10/2005 |
| JP | 2006-140235 | A | 6/2006 |
| JP | 2006-151935 | | 6/2006 |
| JP | 2006-253015 | | 9/2006 |
| WO | WO 2004/075603 | * | 9/2004 |
| WO | WO 2005/068413 | A1 | 7/2005 |
| WO | WO 2005/090512 | A1 | 9/2005 |
| WO | WO 2006/122630 | A1 | 11/2006 |
| WO | WO 2007/013537 | * | 2/2007 |
| WO | 2008/059943 | A1 | 5/2008 |

OTHER PUBLICATIONS

Machine-generated partial translation for JP 2005-289914 A, which was published Oct. 2005.*
Machine-generated English translation for JP 09-310066 (Dec. 1997).*
U.S. Appl. No. 11/932,100, filed Oct. 31, 2007, Takashima, et al.
Zhong Hui Li, et al., "Synthesis and Functional Properties of End-Dendronized Oligo(9,9-diphenyl)fluorenes", Organic Letters, vol. 8, No. 7, 2006,1 front page, pages 1499-1502.
Saulius Grigalevicius, et al., "Well defined carbazol-3,9-diyl based oligomers with diphenylamino end-cap as novel amorphous molecular materials for optoelectronics", Journal of Photochemistry and Photobiology A: Chemistry, vol. 174, No. 2, XP-025301297, Aug. 2005, pp. 125-129.
Martin Sonntag, "New Carbazole Based Materials for Optoelectronic Applications", Bayreuth, Nov. 13, 2006, 161 pages.
Japanese Office Action issued Jul. 17, 2012, in Japan Patent Application No. 2008-545342.
Observations by a Third Party issued Apr. 24, 2012, in European Patent Application No. 07830656.0.

* cited by examiner

*Primary Examiner* — Dawn L. Garrett
(74) *Attorney, Agent, or Firm* — Oblon, Spivak, McClelland, Maier & Neustadt, L.L.P.

(57) ABSTRACT

An aromatic amine derivative with a specific structure having a carbazole skeleton to which a diarylamino group bonds via a bonding group. An organic electroluminescence device which is composed of one or more organic thin film layers including at least one light emitting layer sandwiched between a cathode and an anode, wherein at least one of the organic thin film layers contains the aromatic amine derivative singly or as its mixture component. Organic electroluminescence devices with enhanced efficiency of light emission and a compound realizing the devices are provided.

21 Claims, No Drawings

AROMATIC AMINE DERIVATIVE AND ORGANIC ELECTROLUMINESCENCE DEVICE USING THE SAME

TECHNICAL FIELD

The present invention relates to an aromatic amine derivative and an organic electroluminescence device using the derivative. More particularly, it relates to an organic electroluminescence device with an enhanced efficiency of light emission and a novel aromatic amine derivative realizing the device.

BACKGROUND ART

An organic electroluminescence ("electroluminescence" will be occasionally referred to as "EL", hereinafter) device is a spontaneous light emitting device which utilizes the phenomenon that a fluorescent substance emits light by energy of recombination of holes injected from an anode and electrons injected from a cathode when an electric field is applied. Since an organic EL device of the laminate type driven under a low electric voltage was reported by C. W. Tang et al. of Eastman Kodak Company (C. W. Tang and S. A. Vanslyke, Applied Physics Letters, Volume 51, Page 913, 1987), many studies have been conducted on organic EL devices using organic materials as the constituting materials. Tang et al. used tris(8-quinolinolato)aluminum for the light emitting layer and a triphenyldiamine derivative for the hole transporting layer. Advantages of the laminate structure are that the efficiency of hole injection into the light emitting layer can be increased, that the efficiency of forming excitons which are formed by blocking and recombining electrons injected from the cathode can be increased, and that the excitons formed in the light emitting layer can be confined. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

Conventionally, aromatic diamine derivatives described in Patent Document 1 below and aromatic diamine derivatives with fused rings described in Patent Document 2 below have been known as hole transporting materials for the organic EL devices.

As improved compounds, Patent Documents 3 to 5 disclose arylamine-based compounds containing carbazole, which are employed as hole transporting materials. Further, Patent Document 6 discloses an arylamine-based compound having 3-position-substituted carbazole {e.g. Compound (A) below}, which is employed as a hole injecting material. Although some improvements in an efficiency of light emission or so are achieved in the devices employing those compounds into a hole injecting layer or a hole transporting layer, the efficiency of light emission is not sufficient yet and further enhancement of the efficiency of light emission was required.

Furthermore, although Patent Document 7 discloses arylamine-based compounds having 3-position substituted carbazole {e.g. Compound (B) below}, they are employed as a phosphorescent host material, without reporting any embodiment of employing them as a hole injecting material or a hole transporting material in the past.

Moreover, although Patent Document 8 discloses compounds wherein 3-position substituted carbazole bonds to amine via a phenylene group, there were problems that the compounds have an elevated vapor deposition temperature and that the efficiency of light emission was small. There was a shortcoming in Compound 24 disclosed in Patent Document 9 that it had a short device lifetime. Further, there was also a shortcoming in Compound 40 disclosed in Patent Document 9 that it had an elevated vapor deposition temperature.

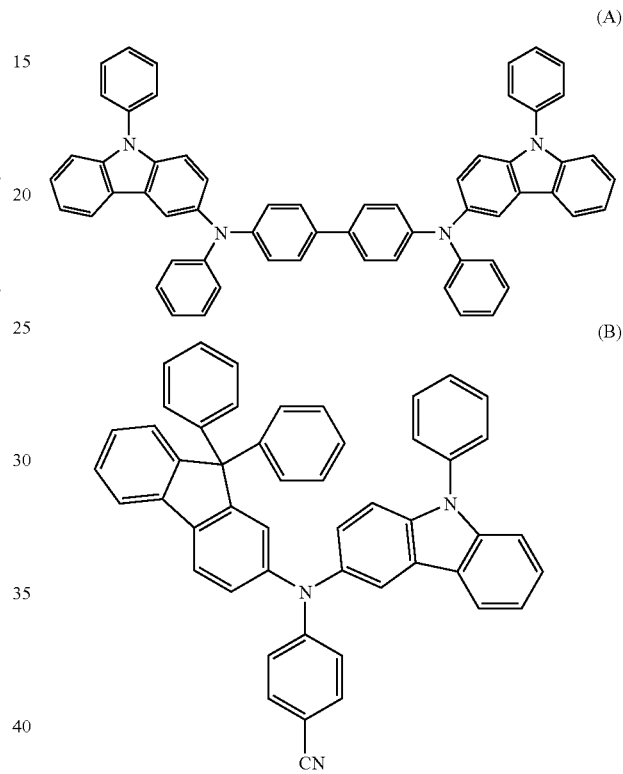

Patent Document 1: U.S. Pat. No. 4,720,432
Patent Document 2: U.S. Pat. No. 5,061,569
Patent Document 3: U.S. Pat. No. 6,242,115
Patent Document 4: JP 11-144873A
Patent Document 5: JP 2000-302756A
Patent Document 6: JP 2006-151979A
Patent Document 7: JP 2005-290000A
Patent Document 8: JP 2003-133075A
Patent Document 9: JP 2004-079265A

DISCLOSURE OF THE INVENTION

Problems to be Solved by the Invention

The present invention has been made to overcome the above problems and has an object of providing an organic EL device having an enhanced efficiency of light emission, and an object of providing a compound realizing the EL device.

Means for Solving the Problem

As a result of intensive researches and studies to achieve the above object by the present inventors, it was found that an employment of an aromatic amine derivative having a carbazole skeleton bonding with a diarylamino group via a bonding group as a material for the organic EL device, especially as a hole transporting material or a hole injecting material for the organic EL device enables to produce an organic EL device having an enhanced efficiency of light emission, resultantly completing the present invention. Because the compound of the present invention has an effect of blocking electrons from a neighboring layer in an electron transporting layer side resulting as Ea (Electron affinity) becoming shallow compared with the compound having structures of the above (A), (B) or so, it is considered that a recombination efficiency rises and an efficiency of light emission enhances.

Namely, the present invention provides an aromatic amine derivative represented by the following general formula (1):

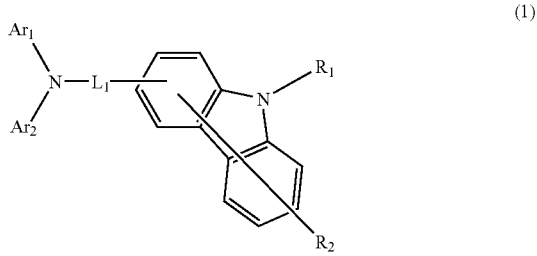

(1)

(In the formula, $L_1$ represents a substituted or unsubstituted arylene group having 6 to 60 carbon atoms forming the aromatic ring, a substituted or unsubstituted fluorenylene group, or a substituted or unsubstituted heteroarylene group having 5 to 60 atoms forming a ring; $Ar_1$ and $Ar_2$ each independently represents a substituted or unsubstituted aryl group having 6 to 60 carbon atoms forming the aromatic ring or a substituted or unsubstituted heteroaryl group having 5 to 60 atoms forming a ring; $R_1$ represents a substituted or unsubstituted aryl group having 6 to 60 carbon atoms forming the aromatic ring; $R_2$ represents a hydrogen atom, a substituted or unsubstituted aryl group having 6 to 60 carbon atoms forming the aromatic ring, a substituted or unsubstituted alkyl group having 1 to 50 carbon atoms, a substituted or unsubstituted alkoxy group having 1 to 50 carbon atoms, a substituted or unsubstituted aryloxy group having 1 to 50 atoms forming a ring, a substituted or unsubstituted arylthio group having 5 to 50 atoms forming a ring, a substituted or unsubstituted alkoxycarbonyl group having 1 to 50 carbon atoms, an amino group substituted by a substituted or unsubstituted aryl group having 5 to 50 carbon atoms forming the aromatic ring, a halogen atom, a cyano group, a nitro group, a hydroxyl group or a carboxyl group; with the proviso that neither $Ar_1$ nor $Ar_2$ contains a fluorene structure, and that the number of a carbazole structure in the aromatic amine derivative represented by the general formula (1) is 1 or 2.)

Further, the present invention provides an organic EL device which is composed of one or more organic thin film layers including at least one light emitting layer and sandwiched between a cathode and an anode, wherein at least one of the organic thin film layers contains the aromatic amine derivative singly or in combination of two or more.

Effect of the Invention

The organic EL device employing the aromatic amine derivative of the present invention as a material for the organic EL device has an enhanced efficiency of light emission.

PREFERRED EMBODIMENT TO CARRY OUT THE INVENTION

The present invention provides an aromatic amine derivative represented by the following general formula (1):

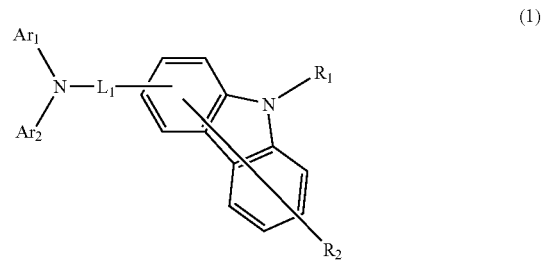

(1)

In the general formula (1), $L_1$ represents a substituted or unsubstituted arylene group having 6 to 60 (preferably 6 to 18) carbon atoms forming the aromatic ring, a substituted or unsubstituted fluorenylene group, or a substituted or unsubstituted heteroarylene group having 5 to 60 (preferably 5 to 20) atoms forming a ring.

Examples of the arylene group and the heteroarylene group represented by $L_1$ include divalent groups of phenyl group, 1-naphthyl group, 2-naphthyl group, 1-anthryl group, 2-anthryl group, 9-anthryl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenylyl group, 4"-t-butyl-p-terphenyl 4-yl group, fluoranthenyl group, fluorenyl group, 1-pyrrolyl group, 2-pyrrolyl group, 3-pyrrolyl group, pyrazinyl group, 2-pyridinyl group, 3-pyridinyl group, 4-pyridinyl group, 1-indolyl group, 2-indolyl group, 3-indolyl group, 4-indolyl group, 5-indolyl group, 6-indolyl group, 7-indolyl group, 1-iso indolyl group, 2-iso indolyl group, 3-iso indolyl group, 4-iso indolyl group, 5-iso indolyl group, 6-iso indolyl group, 7-iso indolyl group, 2-furyl group, 3-furyl group, 2-benzofuranyl group, 3-benzofuranyl group, 4-benzofuranyl group, 5-benzofuranyl group, 6-benzofuranyl group, 7-benzofuranyl group, 1-isobenzofuranyl group, 3-isobenzofuranyl group, 4-isobenzofuranyl group, 5-isobenzofuranyl group, 6-isobenzofuranyl group, 7-isobenzofuranyl group, quinolyl group, 3-quinolyl group, 4-quinolyl group, 5-quinolyl group, 6-quinolyl group, 7-quinolyl group, 8-quinolyl group, 1-isoquinolyl group, 3-isoquinolyl group, 4-isoquinolyl group, 5-isoquinolyl group, 6-isoquinolyl group, 7-isoquinolyl group, 8-isoquinolyl group, 2-quinoxalinyl group, 5-quinoxalinyl group, 6-quinoxalinyl group, 1-carbazolyl group, 2-carbazolyl group, 3-carbazolyl group, 4-carbazolyl group, 9-carbazolyl group, 1-phenanthridinyl group, 2-phenanthridinyl group, 3-phenanthridinyl group, 4-phenanthridinyl group, 6-phenanthridinyl group, 7-phenanthridinyl group, 8-phenanthridinyl group, 9-phenanthridinyl group, 10-phenanthridinyl group, 1-acridinyl group, 2-acridinyl group, 3-acridinyl group, 4-acridinyl group, 9-acridinyl group, 1,7-phenanthroline-2-yl group, 1,7-phenanthroline-3- yl group, 1,7-phenanthroline-4-yl group, 1,7-phenanthroline-5-yl group, 1,7-phenanthroline-6-yl group, 1,7-phenanthroline-8-yl group, 1,7-phenanthroline-9-yl group, 1,7-phenanthroline-10-yl group, 1,8-phenanthroline-2-yl group, 1,8-phenanthroline-3-yl group, 1,8-phenanthroline-4-yl group, 1,8-phenanthroline-5-yl group, 1,8-phenanthroline-6-yl group, 1,8-phenanthroline-7-yl group, 1,8-phenanthroline-9-yl group, 1,8-phenanthroline-10-yl group, 1,9-phenanthroline-2-yl group, 1,9-phenanthroline-3-yl group, 1,9-phenanthroline-4-yl group, 1,9-phenanthroline-5-yl group, 1,9-phenanthroline-6-yl group, 1,9-phenanthroline-7-yl group, 1,9-phenanthroline-8-yl group, 1,9-phenanthroline-10-yl group, 1,10-phenanthroline-2-yl group, 1,10-phenanthroline-3-yl group, 1,10-phenanthroline-4-yl group, 1,10-phenanthroline-5-yl group, 2,9-phenanthroline-1-yl group, 2,9-phenanthroline-3-yl group, 2,9-phenanthroline-4-yl group, 2,9-phenanthroline-5-yl group, 2,9-phenanthroline-6-yl group, 2,9-phenanthroline-7-yl group, 2,9-phenanthroline-8-yl group, 2,9-phenanthroline-10-yl group, 2,8-phenanthroline-1-yl group, 2,8-phenanthroline-3-yl group, 2,8-phenanthroline-4-yl group, 2,8-phenanthroline-5-yl group, 2,8-phenanthroline-6-yl group, 2,8-phenanthroline-7-yl group, 2,8-phenanthroline-9-yl group, 2,8-phenanthroline-10-yl group, 2,7-phenanthroline-1-yl group, 2,7-phenanthroline-3-yl group, 2,7-phenanthroline-4-yl group, 2,7-phenanthroline-5-yl group, 2,7-phenanthroline-6-yl group, 2,7-phenanthroline-8-yl group, 2,7-phenanthroline-9-yl group, 2,7-phenanthroline-10-yl group, 1-phenazinyl group, 2-phenazinyl group, 1-phenothiazinyl group, 2-phenothiazinyl group, 3-phenothiazinyl group, 4-phenothiazinyl group, 10-phenothiazinyl group, 1-phenoxazinyl group, 2-phenoxazinyl group, 3-phenoxazinyl group, 4-phenoxazinyl group, 10-phenoxazinyl group, 2-oxazolyl group, 4-oxazolyl group, 5-oxazolyl group, 2-oxadiazolyl group, 5-oxadiazolyl group, 3-furazanyl group, 2-thienyl group, 3-thienyl group, 2-methylpyrrole-1-yl group, 2-methylpyrrole-3-yl group, 2-methylpyrrole-4-yl group, 2-methylpyrrole-5-yl group, 3-methylpyrrole-1-yl group, 3-methylpyrrole-2-yl group, 3-methylpyrrole-4-yl group, 3-methylpyrrole-5-yl group, 2-t-butylpyrrole-4-yl group, 3-(2-phenylpropyl)pyrrole-1-yl group, 2-methyl-1-indolyl group, 4-methyl-1-indolyl group, 2-methyl-3-indolyl group, 4-methyl-3-indolyl group, 2-t-butyl-1-indolyl group, 4-t-butyl-1-indolyl group, 2-t-butyl-3-indolyl group, 4-t-butyl-3-indolyl group, etc.

Preferable examples of the arylene group represented by $L_1$ include phenylene group, biphenylene group, terphenylene group, quarterphenylene group, naphthylene group, anthracenylene group, phenanthrylene group, chrycenylene group, pyrenylene group, perilenylene group, fluorenylene group, etc. Preferable examples are phenylene group, biphenylene group, terphenylene group, fluorenylene group, naphthylene group, phenanthrylene group. Further preferable examples are phenylene group, biphenylene group, terphenylene group, naphthylene, group, phenanthrylene group or fluorenylene group.

Preferable heteroarylene groups are divalent groups of thiophenylyl group, 1-phenylthiophenylyl group, 1,4-diphenylthiophenylyl group, benzthiophenylyl group, 1-phenylbenzothiophenylyl group, 1,8-diphenylbenzothiophenylyl group, furyl group, 1-phenyldibenzothiophenylyl group, 1,8-diphenylthiophenylyl group, dibenzofuranyl group, 1-phenyldibenzofuranyl group, 1,8-diphenyldibenzofuranyl group, benzothiazolyl group, etc. Further preferable heteroarylene groups are divalent groups of 1-phenylthiophenylyl group, 1-phenylbenzothiophenylyl group, 1-phenyldibenzofuranyl group, benzothiazolyl group, etc.

In the general formula (1), $Ar_1$ and $Ar_2$ each independently represents a substituted or unsubstituted aryl group having 6 to 60 (preferably 6 to 18) carbon atoms forming the aromatic ring or a substituted or unsubstituted heteroaryl group having 5 to 60 (preferably 5 to 20) atoms forming a ring; with the proviso that neither $Ar_1$ nor $Ar_2$ contains a fluorene structure.

Examples of the aryl group represented by $Ar_1$ or $Ar_2$ include phenyl group, 1-naphthyl group, 2-naphthyl group, 1-anthracenyl group, 2-anthracenyl group, 9-anthracenyl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, etc.

Examples of the heteroaryl group represented by $Ar_1$ or $Ar_2$ include monovalent group or so of the hetero arylene group represented by the above $L_1$.

In a general formula (1), $R_1$ represents a substituted or unsubstituted aryl group having 6 to 60 (preferably 6 to 18) carbon atoms forming the aromatic ring.

Examples of the aryl group represented by the above $R_1$ include phenyl group, 1-naphthyl group, 2-naphthyl group, 1-anthracenyl group, 2-anthracenyl group, 9-anthracenyl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4"-t-butyl-p-terphenyl-4-yl group, etc. Preferable examples are phenyl group, 1-naphthyl group, 2-naphthyl group, 4-biphenylyl group, p-terphenyl-4-yl group and more preferable examples are phenyl group, biphenylyl group, terphenylyl group, α-naphthyl, group, β-naphthyl group and phenanthryl group.

In the general formula (1), $R_2$ represents a hydrogen atom, a substituted or unsubstituted aryl group having 6 to 60 (preferably 6 to 30) carbon atoms forming the aromatic ring, a substituted or unsubstituted alkyl group having 1 to 50 (preferably 1 to 20) carbon atoms, a substituted or unsubstituted alkoxy group having 1 to 50 (preferably 1 to 20) carbon atoms, a substituted or unsubstituted aryloxy group having 6 to 50 (preferably 6 to 20) atoms forming a ring, a substituted or unsubstituted arylthio group having 5 to 50 (preferably 6 to 20) atoms forming a ring, a substituted or unsubstituted alkoxycarbonyl group having 2 to 50 (preferably 2 to 20) carbon atoms, an amino group substituted by a substituted or unsubstituted aryl group having 6 to 50 (preferably 6 to 20) carbon atoms forming the aromatic ring, a halogen atom, a cyano group, a nitro group, a hydroxyl group or a carboxyl group.

In the general formula (1), it is preferable that $R_2$ corresponds to a substituted or unsubstituted aryl group having 6 to 60 carbon atoms forming the aromatic ring bonded to 3- or 6-position of a carbazole skeleton.

Examples of the aryl group represented by $R_2$ include phenyl group, 1-naphthyl group, 2-naphthyl group, 1-anthracenyl group, 2-anthracenyl group, 9-anthracenyl group, 1-phenanthryl group, 2-phenanthryl group, 3-phenanthryl group, 4-phenanthryl group, 9-phenanthryl group, 1-naphthacenyl group, 2-naphthacenyl group, 9-naphthacenyl group, 1-pyrenyl group, 2-pyrenyl group, 4-pyrenyl group, 2-biphenylyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 3-methyl-2-naphthyl group, 4-methyl-1-naphthyl group, 4-methyl-1-anthryl group, 4'-methylbiphenyl-yl group, 4''-t-butyl-p-terphenyl-4-yl group, fluorenyl group, etc. Preferable examples are phenyl group, 1-naphthyl group, 2-naphthyl group, 4-biphenylyl group, p-terphenyl-4-yl, group, p-tolyl group and fluorenyl group.

Examples of the alkyl group represented by $R_2$ include methyl group, ethyl group, iso-propyl group, tert-butyl group, n-octyl group, n-decyl group, n-hexadecyl group, cyclopropyl group, cyclopentyl group, cyclohexyl group, vinyl group, allyl group, 2-butenyl group, 3-pentenyl group, propargyl group, 3-pentynyl group, etc. Preferable examples are methyl group, ethyl group, iso-propyl group, tert-butyl, group, cyclopentyl group and cyclohexyl group.

Examples of the alkoxy group represented by $R_2$ include methoxy group, ethoxy group, n-propoxy group, iso-propoxy group, n-butoxy group, tert-butoxy group, etc. Preferable examples are methoxy group, ethoxy group and tert-butoxy group.

Examples of the aryloxy group represented by $R_2$ include phenyloxy group, 1-naphthyloxy group, 2-naphthyloxy group, 4-biphenylyloxy group, p-terphenyl-4-yloxy group, p-tolyloxy group, etc. Preferable examples are phenyloxy group and 2-naphthyloxy group.

Examples of the arylthio group represented by $R_2$ include phenylthio group, 1-naphthylthio group, 2-naphthylthio group, 4-biphenylylthio group, p-terphenyl-4-ylthio group, p-tolylthio group, etc. Preferable examples are phenylthio group and 2-naphthylthio group.

Examples of the alkoxycarbonyl group represented by $R_2$ include methoxycarbonyl group, ethoxycarbonyl group, n-propoxycarbonyl group, iso-propoxycarbonyl group, n-butoxycarbonyl group, tert-butoxycarbonyl group, etc. Preferable examples are methoxycarbonyl group and ethoxycarbonyl group.

Examples of the amino group substituted by the aryl group represented by $R_2$ include an amino group substituted by the aryl group represented by $R_1$, etc.

Examples of the amino group represented by $R_2$ include amino group, methylamino group, dimethylamino group, diethylamino group, dibenzylamino group, etc. Preferable examples are dimethylamino group and diethylamino group.

Examples of the halogen atom represented by $R_2$ include fluorine atom, chlorine atom, bromine atom, iodine atom, etc.

Further, $R_2$ is preferably a hydrogen atom, a phenyl group, a biphenylyl group, a terphenylyl group, an α-naphthyl group, a β-naphthyl group, a methyl group, an ethyl group, a propyl group, an isopropyl group, an arylamino group, etc.

Each these groups may be further substituted, and when there are two or more groups, they may be the same with or different from each other. Moreover, in a case where it is possible, they may couple each other to form a ring.

Examples of substituents for each groups of $Ar_1$, $Ar_2$, $R_1$ and $R_2$ include, alkyl group (alkyl group preferably having 1 to 20 carbon atoms, more preferably having 1 to 12 carbon atoms and particularly preferably having 1 to 8 carbon atoms; examples include methyl, ethyl, iso-propyl, tert-butyl, n-octyl, n-decyl, n-hexadecyl, cyclopropyl, cyclopentyl, cyclohexyl, etc.); alkenyl group (alkenyl group preferably having 2 to 20 carbon atoms, more preferably having 2 to 12 carbon atoms and particularly preferably having 2 to 8 carbon atoms; examples include vinyl, allyl, 2-butenyl, 3-pentenyl, etc.); alkynyl group (alkynyl group preferably having 2 to 20 carbon atoms, more preferably having 2 to 12 carbon atoms and particularly preferably having 2 to 8 carbon atoms; examples include propargyl, 3-pentynyl, etc.); amino group (amino group preferably having 0 to 20 carbon atoms, more preferably having 0 to 12 carbon atoms and particularly preferably having 0 to 6 carbon atoms; examples include amino, methylamino, dimethylamino, diethylamino, diphenylamino, dibenzylamino, etc.); alkoxy group (alkoxy group preferably having 1 to 20 carbon atoms, more preferably having 1 to 12 carbon atoms and particularly preferably having 1 to 8 carbon atoms; examples include methoxy, ethoxy, butoxy, etc.); aryloxy group (aryloxy group preferably having 6 to 20 carbon atoms, more preferably having 6 to 16 carbon atoms and particularly preferably having 6 to 12 carbon atoms; examples include phenyloxy, 2-naphthyloxy, etc.); acyl group (acyl group preferably having 1 to 20 carbon atoms, more preferably having 1 to 16 carbon atoms and particularly preferably having 1 to 12 carbon atoms; examples include acetyl, benzoyl, formyl, pivaloyl, etc.); alkoxycarbonyl group (alkoxycarbonyl group preferably having 2 to 20 carbon atoms, more preferably having 2 to 16 carbon atoms and particularly preferably having 2 to 12 carbon atoms; examples include methoxycarbonyl, ethoxycarbonyl, etc.); aryloxycarbonyl group (aryloxycarbonyl group preferably having 7 to 20 carbon atoms, more preferably having 7 to 16 carbon atoms and particularly preferably having 7 to 10 carbon atoms; examples include phenyloxycarbonyl, etc.); acyloxy group (acyloxy group preferably having 2 to 20 carbon atoms, more preferably having 2 to 16 carbon atoms and particularly preferably having 2 to 10 carbon atoms; examples include acetoxy, benzoyloxy, etc.); acylamino group (acylamino group preferably having 2 to 20 carbon atoms, more preferably having 2 to 16 carbon atoms and particularly preferably having 2 to 10 carbon atoms; examples include acetylamino, benzoylamino, etc.); alkoxycarbonylamino group (alkoxycarbonylamino group preferably having 2 to 20 carbon atoms, more preferably having 2 to 16 carbon atoms and particularly preferably having 2 to 12 carbon atoms; examples include methoxycarbonylamino, etc.); aryloxycarbonylamino group (aryloxycarbonylamino group preferably having 7 to 20 carbon atoms, more preferably having 7 to 16 carbon atoms and particularly preferably having 7 to 12 carbon atoms; examples include phenyloxycarbonylamino, etc.); sulfonylamino group (sulfonylamino group preferably having 1 to 20 carbon atoms, more preferably having 1 to 16 carbon atoms and particularly preferably having 1 to 12 carbon atoms; examples include methanesulfonylamino, benzensulfonylamino, etc.); sulfamoyl group (sulfamoyl group preferably having 0 to 20 carbon atoms, more preferably having 0 to 16 carbon atoms and particularly preferably having 0 to 12 carbon atoms; examples include sulfamoyl, methylsulfamoyl, dimethylsulfamoyl, phenylsulfamoyl, etc.); carbamoyl group (carbamoyl group preferably having 1 to 20 carbon atoms, more preferably having 1 to 16 carbon atoms and particularly preferably having 1 to 12 carbon atoms; examples include carbamoyl, methylcarbamoyl, diethylcarbamoyl, phenylcarbamoyl, etc.); alkylthio group (alkylthio group preferably having 1 to 20 carbon atoms, more preferably having 1 to 16 carbon atoms and particularly preferably having 1 to 12 carbon atoms; examples include methylthio, ethylthio, etc.); arylthio group (arylthio group preferably having 6 to 20 carbon atoms, more preferably having 6 to 16 carbon atoms and particularly preferably having 6 to 12 carbon atoms; examples include phenylthio, etc.); sulfonyl group (sulfonyl group preferably having 1 to 20 carbon atoms, more preferably having 1 to 16 carbon atoms and particularly preferably having 1 to 12 carbon atoms; examples include mesyl, tosyl, etc.); sulfinyl group (sulfinyl group preferably having 1 to 20 carbon atoms, more preferably having 1 to 16 carbon atoms and particularly preferably having 1 to 12 carbon atoms; examples include methanesulfinyl, benzenesulfinyl, etc.); ureide group (ureide group preferably having 1 to 20 carbon atoms, more preferably having 1 to 16 carbon atoms and particularly preferably having 1 to 12 carbon atoms; examples include ureide, methylureide, phenylureide, etc.); phosphoricamide group (phosphoricamide group preferably having 1 to 20 carbon atoms, more preferably having 1 to 16 carbon atoms and particularly preferably having 1 to 12 carbon atoms; examples include diethylphosphoricamide, phenylphosphateamide, etc.); hydroxy group; mercapto group; halogen atom (for example, fluorine atom, chlorine atom, bromine atom and iodine atom); cyano group; sulfo group; carboxyl group; nitro group; hydroxamic acid group; sulfino group; hydrazino group; imino group; heterocyclic group (heterocyclic group preferably having 1 to 30 carbon atoms, more preferably having 1 to 12 carbon atoms; examples of the hetero atom include nitrogen atom, oxygen atom, sulfur atom; specific examples of the heterocyclic group include imidazolyl, pyridyl, quinolyl, furyl, thienyl, piperidyl, morpholino, benzoxazolyl, benzimidazolyl, benzothiazolyl, carbazolyl, etc.); silyl group (silyl group preferably having 3 to 40 carbon atoms, more preferably having 3 to 30 carbon atoms and particularly preferably having 3 to 24 carbon atoms; examples include trimethylsilyl, triphenylsilyl, etc.); etc. Those substituents may be further substituted. Furthermore, when there are two or more substituents, the substituents may be the same with or different from each other. Moreover, in a case where it is possible, they may bond each other to form a ring.

It is preferable for the aromatic amine derivative represented by the general formula (1) of the present invention has a structure represented by the following general formulae (1-a), (1-b), (1-c), (1-d), (1-e) and (1-f).

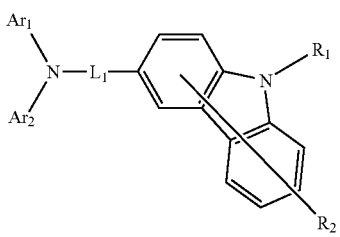
(1-a)

In the general formula (1-a), $L_1$, $Ar_1$, $Ar_2$, $R_1$ and $R_2$ are the same as those defined in the general formula (1) respectively, and specific examples, preferable examples and substituents are almost the same as described above. Further, $Ar_1$ and $Ar_2$ may be the same with or different from each other.

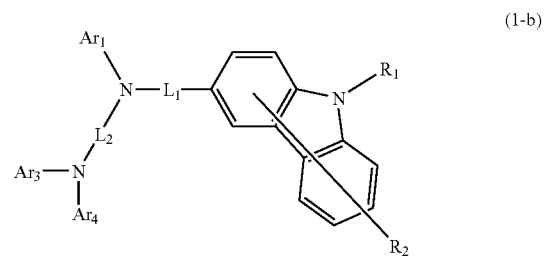
(1-b)

In the general formula (1-b), $L_1$, $Ar_1$, $R_1$ and $R_2$ are the same as those defined in the general formula (1) respectively, and specific examples, preferable examples and substituents are almost the same as described above.

$L_2$ represents a substituted or unsubstituted arylene group having 6 to 60 carbon atoms forming the aromatic ring, or a substituted or unsubstituted heteroarylene group having 5 to 60 atoms forming a ring; and specific examples, preferable examples and substituents are almost the same as those described about the above $L_1$.

$Ar_3$ and $Ar_4$ each independently represents a substituted or unsubstituted aryl group having 6 to 60 carbon atoms forming the aromatic ring; and specific examples, preferable examples and substituents of the aryl group are almost the same as those described about the above $Ar_1$; with the proviso that neither $Ar_3$ nor $Ar_4$ contains a fluorene structure.

$Ar_1$, $Ar_3$ and $Ar_4$ may be the same with or different from each other.

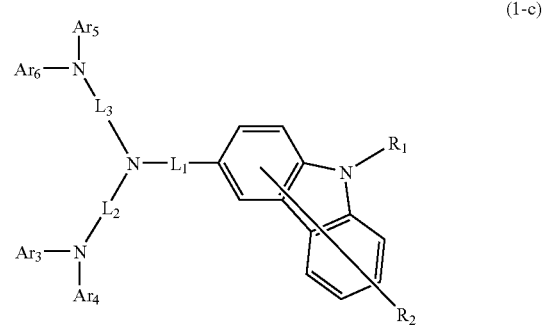
(1-c)

In the general formula (1-c), $L_1$, $R_1$ and $R_2$ are the same as those defined in the general formula (1) respectively, and specific examples, preferable examples and substituents are almost the same as described above.

$L_2$ and $L_3$ each independently represents a substituted or unsubstituted arylene group having 6 to 60 carbon atoms forming the aromatic ring, or a substituted or unsubstituted heteroarylene group having 5 to 60 atoms forming a ring; and specific examples, preferable examples and substituents are almost the same as those described about the above $L_1$.

$Ar_3$ to $Ar_6$ each independently represents a substituted or unsubstituted aryl group having 6 to 60 ring carbon atom; and specific examples, preferable examples and substituents of the aryl group are almost the same as those described about the above $Ar_1$; with the proviso that none of $Ar_3$ to $Ar_6$ contains a fluorene structure.

Further, $Ar_3$ to $Ar_6$ may be the same with or different from each other.

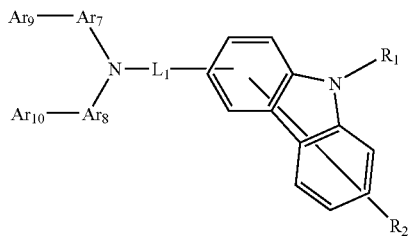
(1-d)

In the general formula (1-d), $L_1$, $R_1$ and $R_2$ are the same as those defined in the general formula (1) respectively, and specific examples, preferable examples and substituents are almost the same as described above.

$Ar_7$ and $Ar_8$ each independently represents a substituted or unsubstituted arylene group having 6 to 60 carbon atoms forming the aromatic ring or a substituted or unsubstituted heteroarylene group having 5 to 60 atoms forming a ring; specific examples and preferable examples include divalent groups of almost the same as those described about the above $Ar_1$, and examples of the substituents also include the same as described above.

$Ar_9$ and $Ar_{10}$ each independently represents a substituted or unsubstituted aryl group having 6 to 60 carbon atoms forming the aromatic ring, or a substituted or unsubstituted heteroaryl group having 5 to 60 atoms forming a ring; and specific examples, preferable examples and substituents are almost the same as those described about the above $Ar_1$; with the proviso that none of $Ar_7$ to $Ar_{10}$ contains a fluorene structure.

Further, $Ar_7$ to $Ar_{10}$ may be the same with or different from each other.

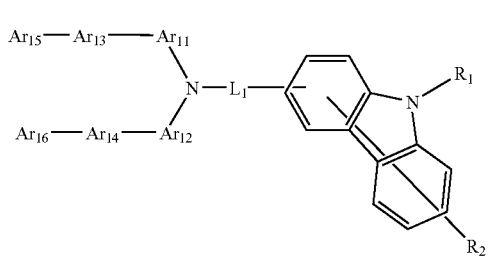
(1-e)

In the general formula (1-e), $L_1$, $R_1$ and $R_2$ are the same as those defined in the general formula (1) respectively, and specific examples, preferable examples and substituents are almost the same as described above.

$Ar_{11}$ to $Ar_{14}$ each independently represents a substituted or unsubstituted arylene group having 6 to 60 carbon atoms forming the aromatic ring or a substituted or unsubstituted heteroarylene group having 5 to 60 atoms forming a ring; specific examples and preferable examples include divalent groups of almost the same as those described about the above $Ar_1$, and examples of the substituents also include the same as described above.

$Ar_{15}$ and $Ar_{16}$ each independently represents a substituted or unsubstituted aryl group having 6 to 60 carbon atoms forming the aromatic ring, or a substituted or unsubstituted heteroaryl group having 5 to 60 atoms forming a ring; and specific examples, preferable examples and substituents are almost the same as those described about the above $Ar_1$; with the proviso that none of $Ar_{11}$ to $Ar_{16}$ contains a fluorene structure.

Further, $Ar_{11}$ to $Ar_{16}$ may be the same with or different from each other.

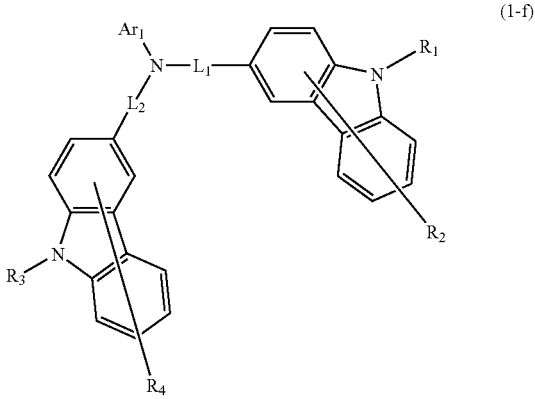
(1-f)

In the general formula (1-f), $L_1$, $Ar_1$, $R_1$ and $R_2$ are the same as those defined in the general formula (1) respectively; $L_2$ represents a substituted or unsubstituted arylene group having 6 to 60 carbon atoms forming the aromatic ring or a substituted or unsubstituted heteroarylene group having 5 to 60 atoms forming a ring; $R_3$ represents a substituted or unsubstituted aryl group having 6 to 60 carbon atoms forming the aromatic ring; $R_4$ represents a hydrogen atom, a substituted or unsubstituted aryl group having 6 to 60 carbon atoms forming the aromatic ring, a substituted or unsubstituted alkyl group having 1 to 50 carbon atoms, a substituted or unsubstituted alkoxy group having 1 to 50 carbon atoms, a substituted or unsubstituted aryloxy group having 6 to 50 atoms forming a ring, a substituted or unsubstituted arylthio group having 5 to 50 atoms forming a ring, a substituted or unsubstituted alkoxycarbonyl group having 2 to 50 carbon atoms, an amino group substituted by a substituted or unsubstituted aryl group having 6 to 50 carbon atoms forming the aromatic ring, a halogen atom, a cyano group, a nitro group, a hydroxyl group or a carboxyl group.

In the general formulae (1), (1-a), (1-b), (1-c), (1-d), (1-e) and (1-f), $L_1$ represents an unsubstituted arylene group having 6 to 60 carbon atoms forming the aromatic ring, an unsubstituted fluorenylene group or an unsubstituted heteroarylene group having 5 to 60 atoms forming a ring; $Ar_1$ and $Ar_2$ each independently represents an unsubstituted aryl group having 6 to 60 carbon atoms forming the aromatic ring or an unsubstituted heteroaryl group having 5 to 60 atoms forming a ring; $R_1$ represents an unsubstituted aryl group having 6 to 60 carbon atoms forming the aromatic ring; $R_2$ represents a hydrogen atom, an unsubstituted aryl group having 6 to 60 carbon atoms forming the aromatic ring or an unsubstituted alkyl group having 1 to 50 carbon atoms; and neither $Ar_1$ nor $Ar_2$ contains a fluorene structure. Further, it is preferable that the aromatic amine derivative represented by the general formula (1), (1-a), (1-b), (1-c), (1-d), (1-e) or (1-f) has 1 or 2 carbazole structures.

Moreover, in the general formulae (1), (1-a), (1-b), (1-c), (1-d), (1-e) and (1-f), it is preferable that $Ar_1$ to $Ar_6$, $Ar_9$, $Ar_{10}$ and $Ar_{15}$ to $Ar_{16}$ each independently represents a substituted or unsubstituted phenyl group, a biphenylyl group, a terphenylyl group, an α-naphthyl group, a β-naphthyl group or a phenanthryl group; and that $Ar_7$, $Ar_8$ and $Ar_{11}$ to $Ar_{14}$ each independently represents a substituted or unsubstituted phenylene group, a biphenylylene group, a terphenylylene group, a naphthylene group or a phenanthrylene groups.

Specific examples of the aromatic amine derivative represented by the general formula (1) of the present invention include the following compounds, though not limited thereto.

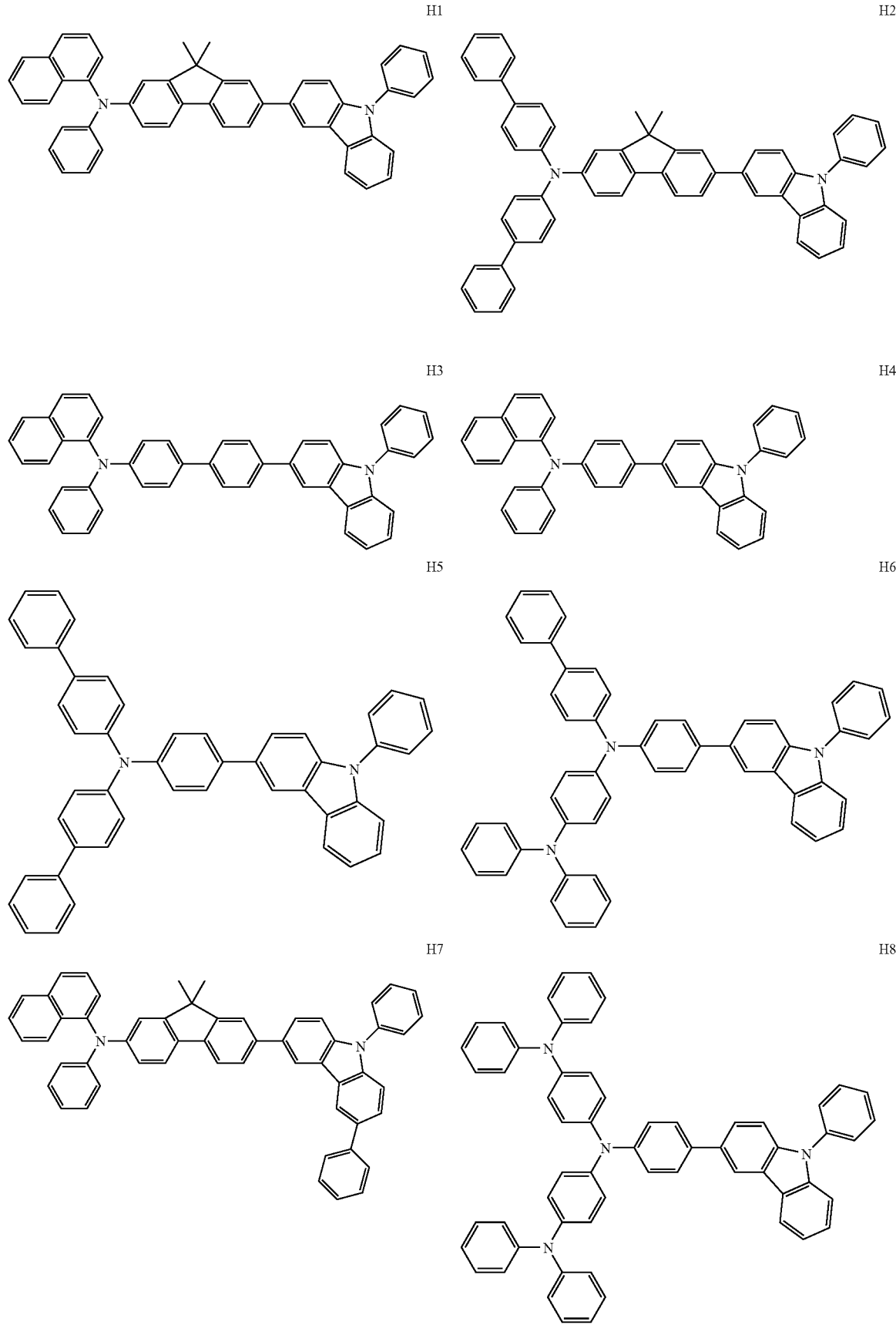

-continued
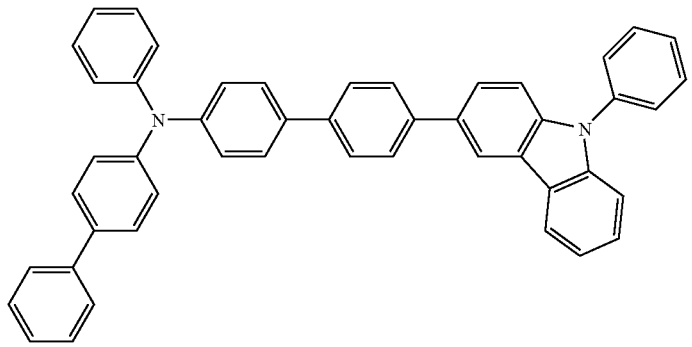
H9
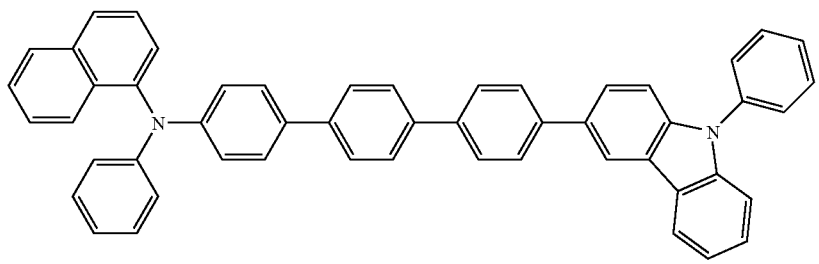
H10
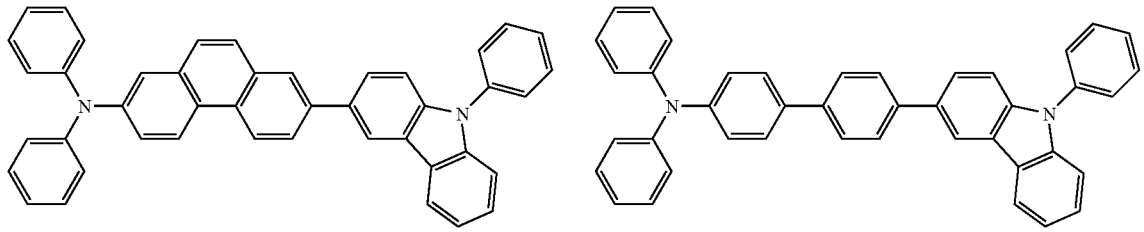
H11   H12
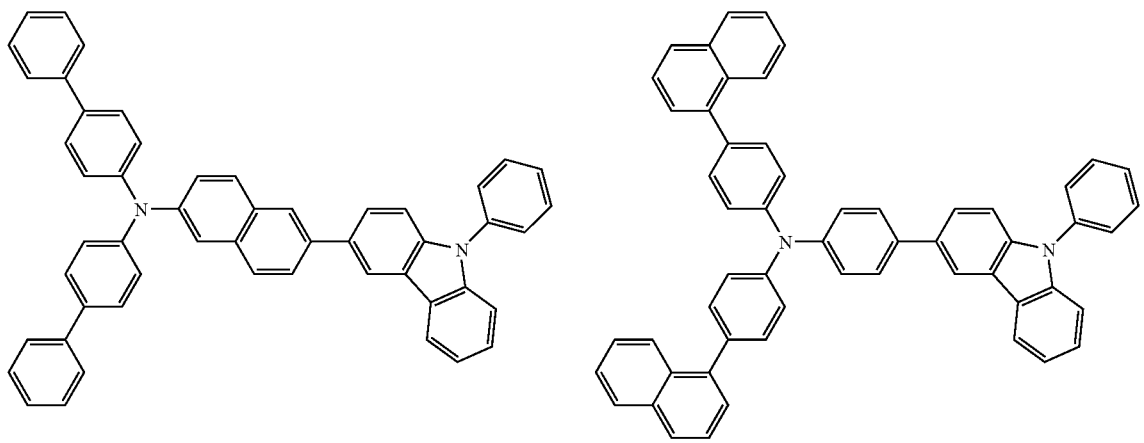
H13   H14

-continued
H15
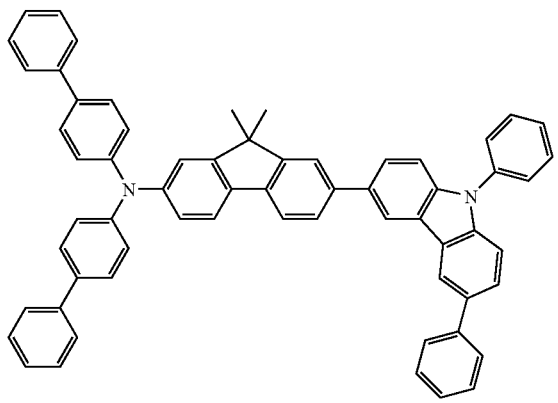
H16
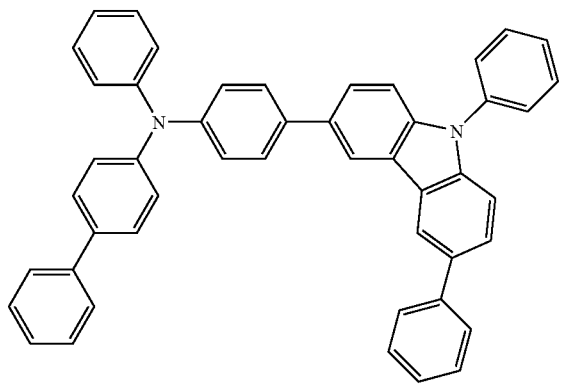
H17
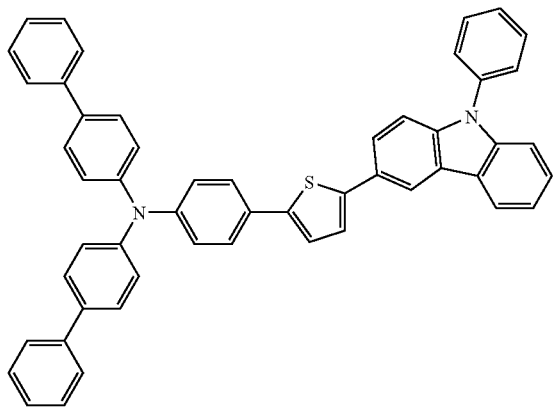
H18
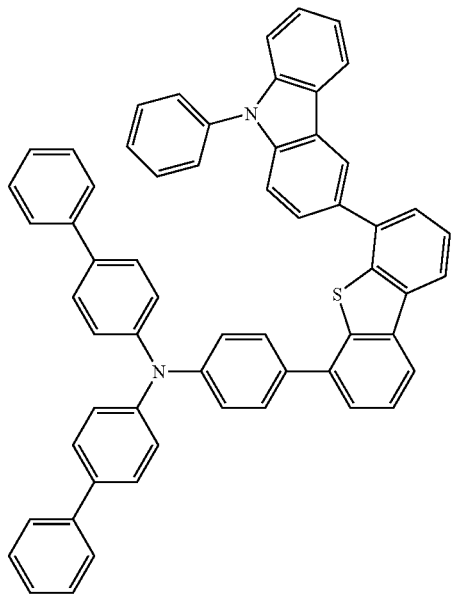
H19
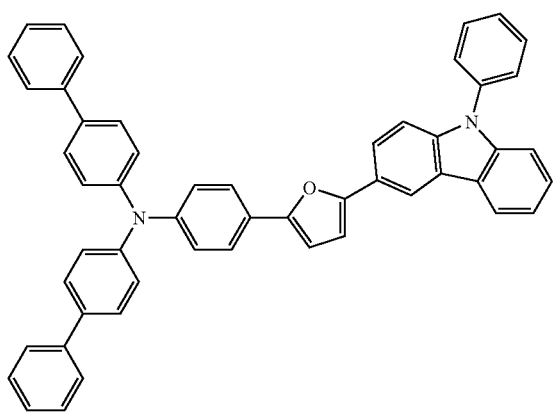
H20
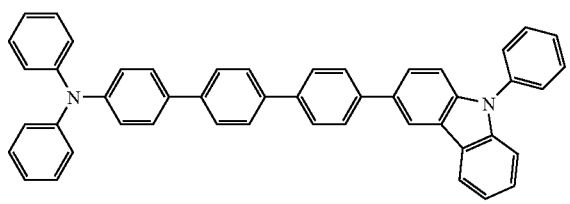

-continued
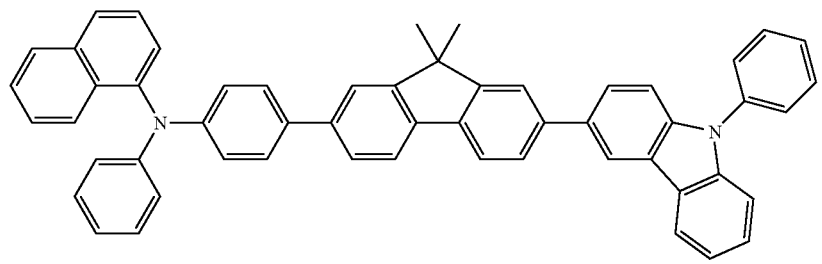
H21
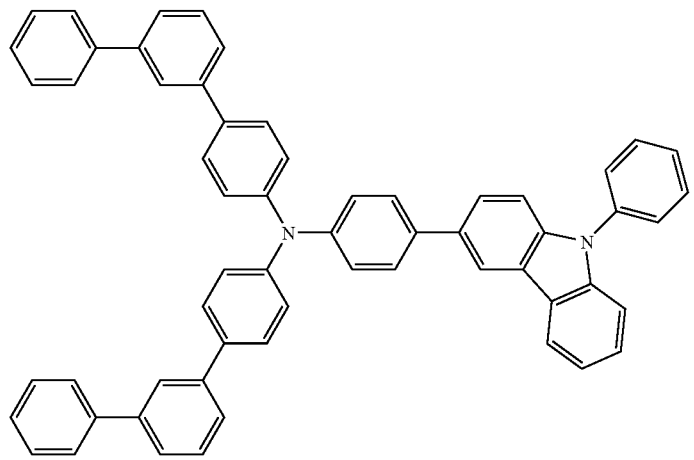
H22
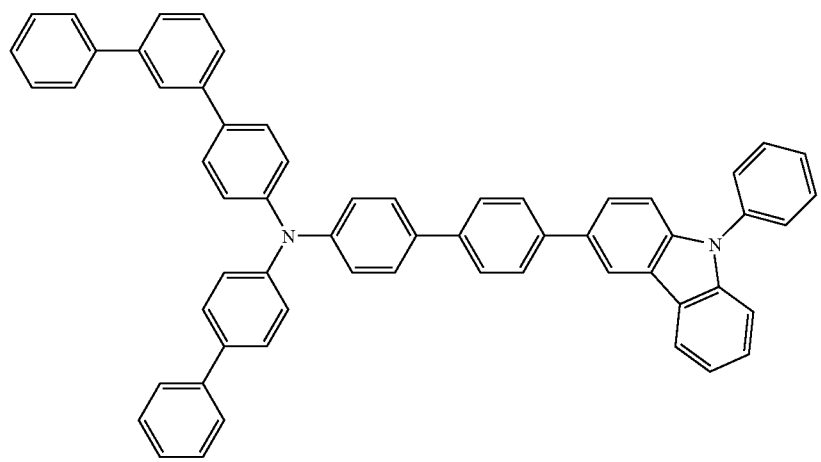
H23

-continued
H24
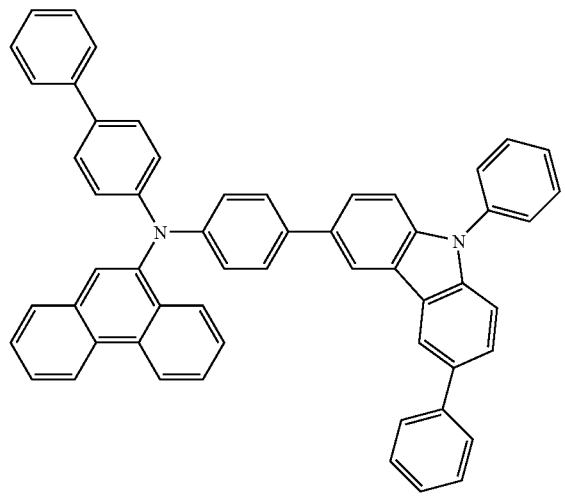
H25
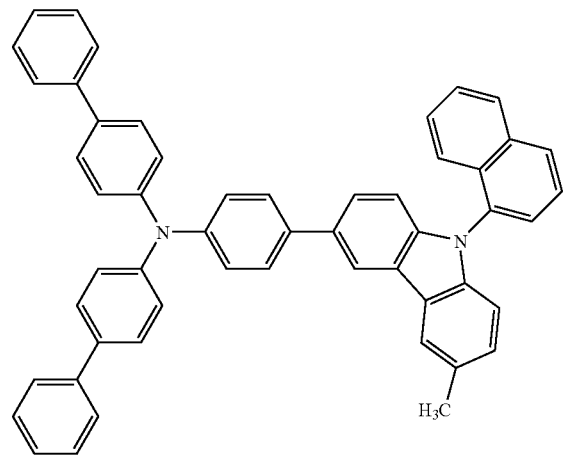
H26
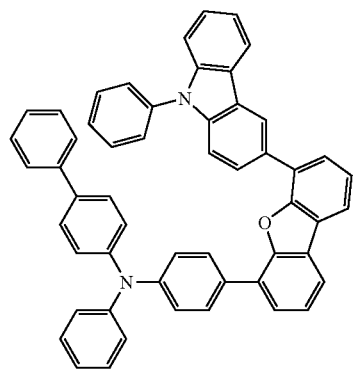
H27
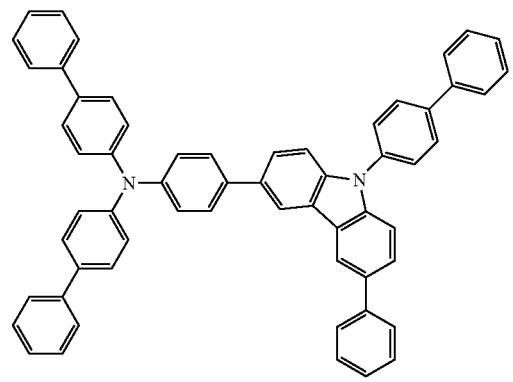
H28
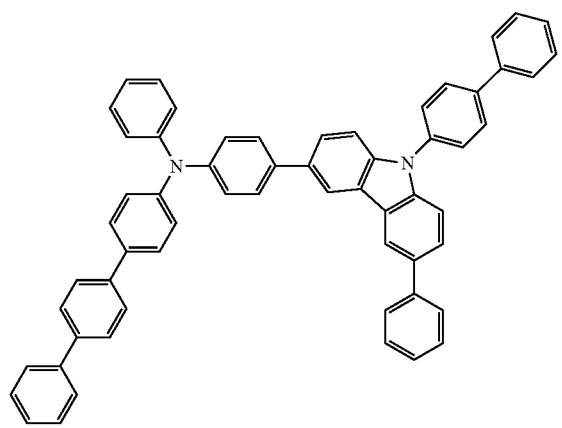
H29
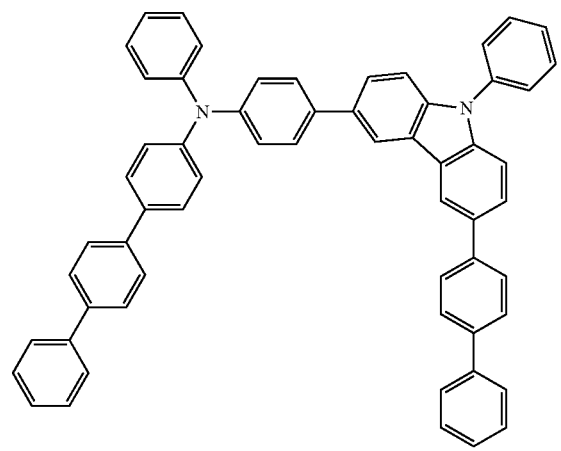

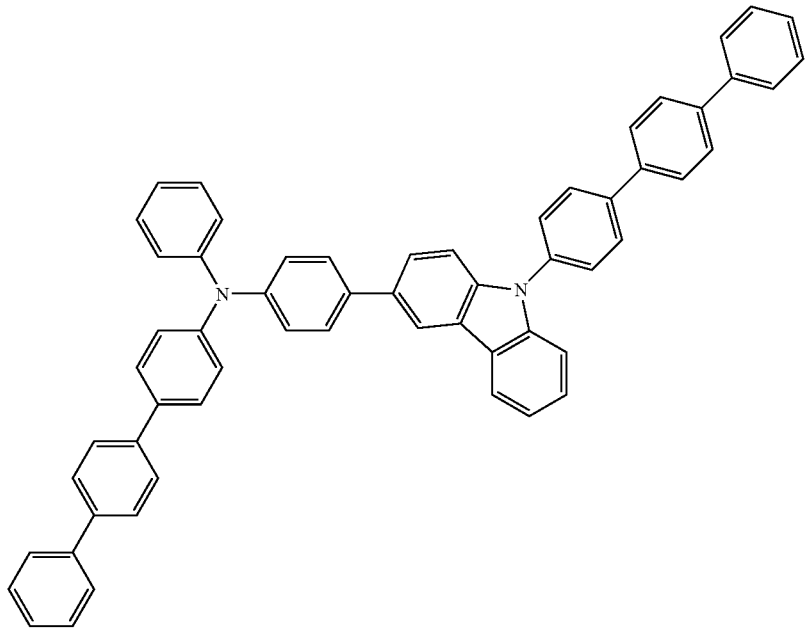
H30
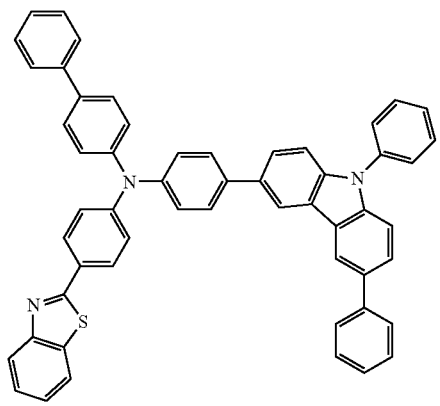
H31
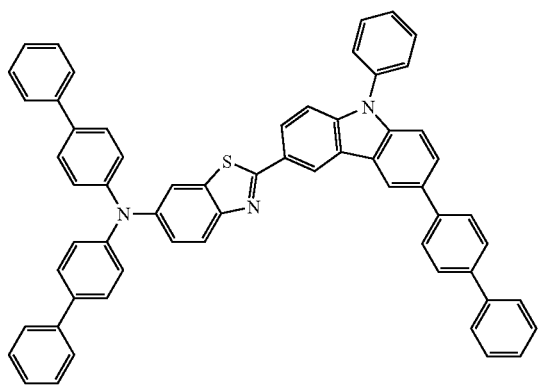
H32
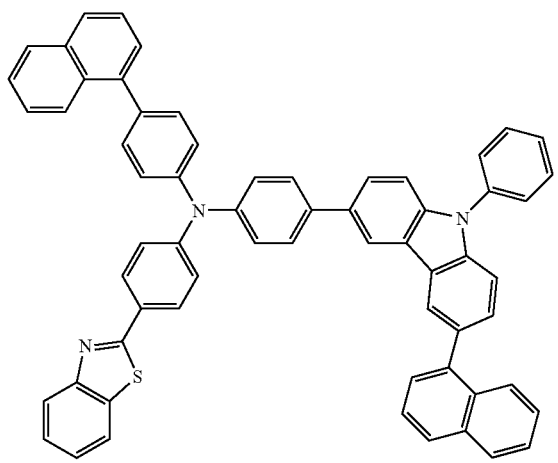
H33
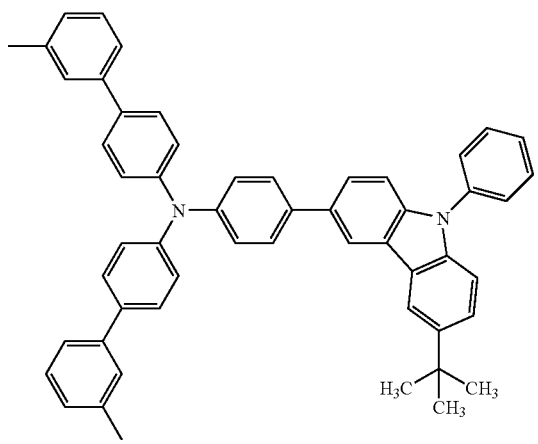
H34

-continued
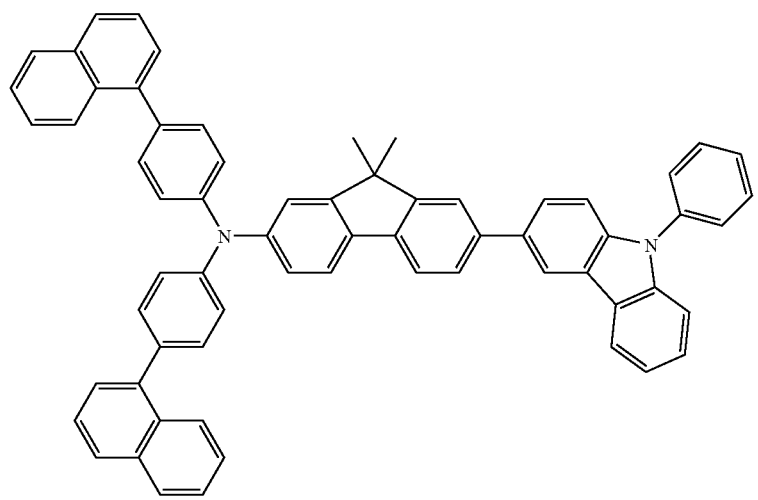
H35
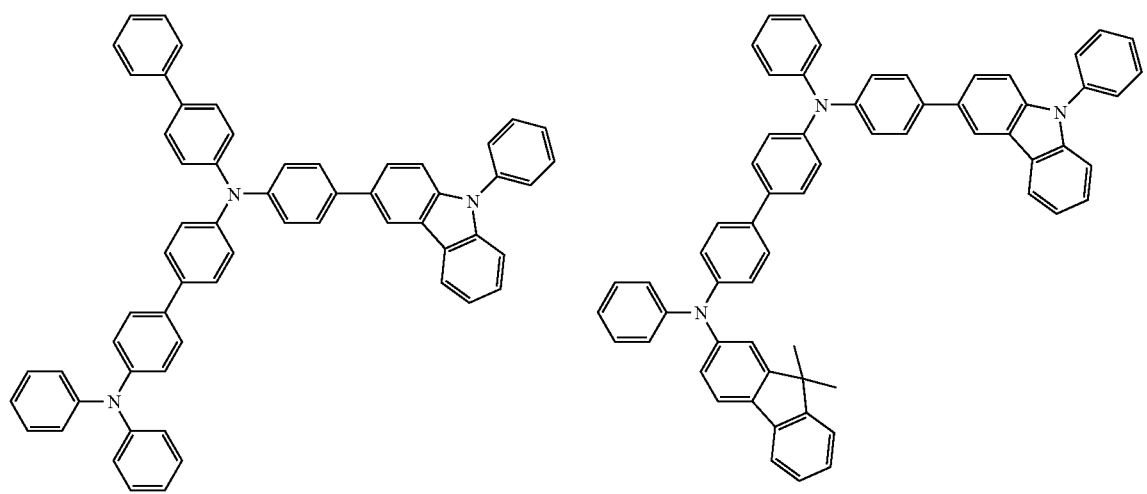
H36 H37
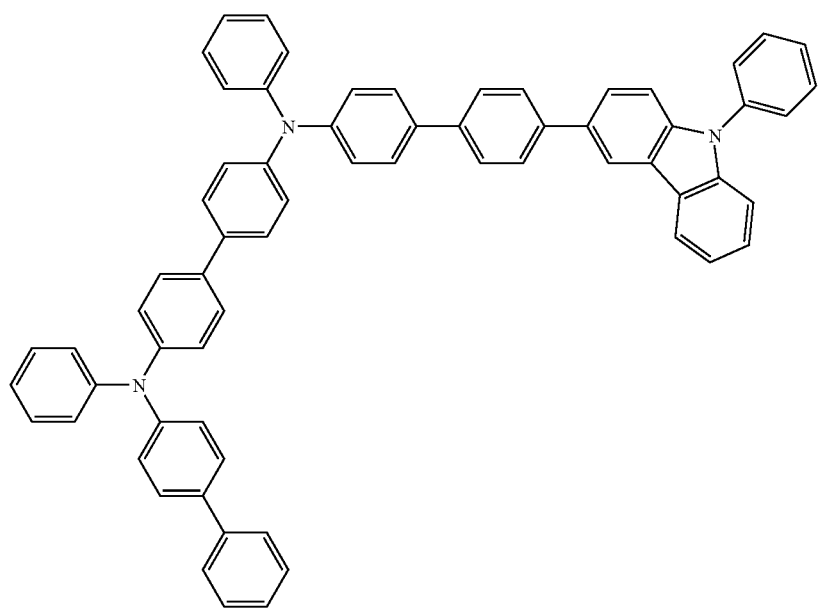
H38

-continued
H39
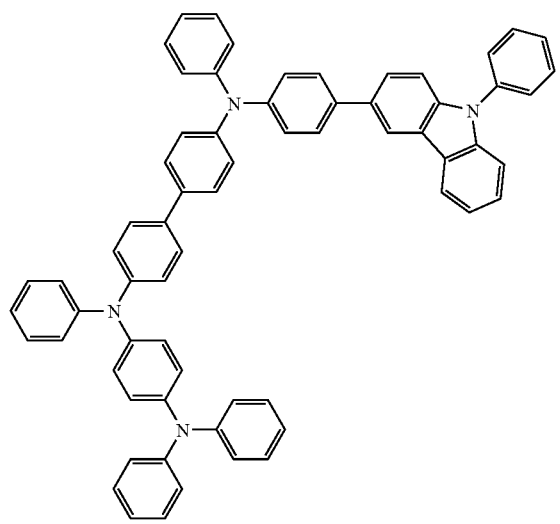
H40
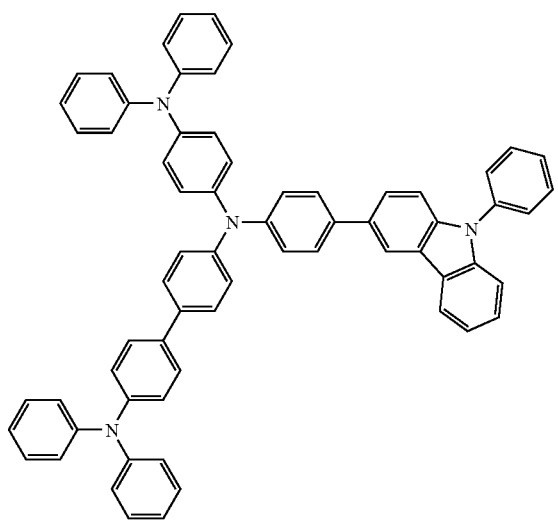
H41
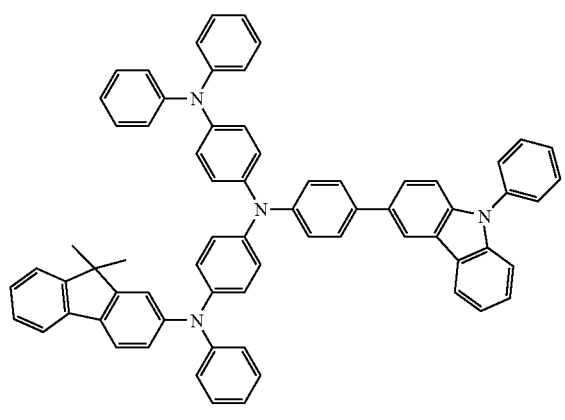
H42
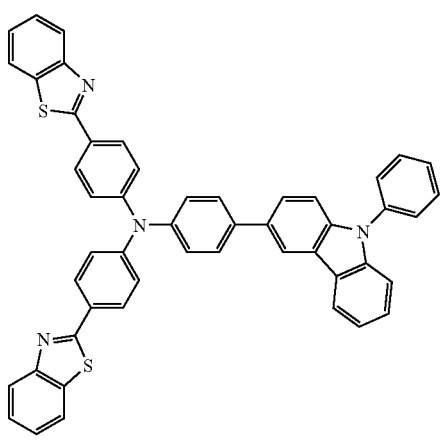
H43
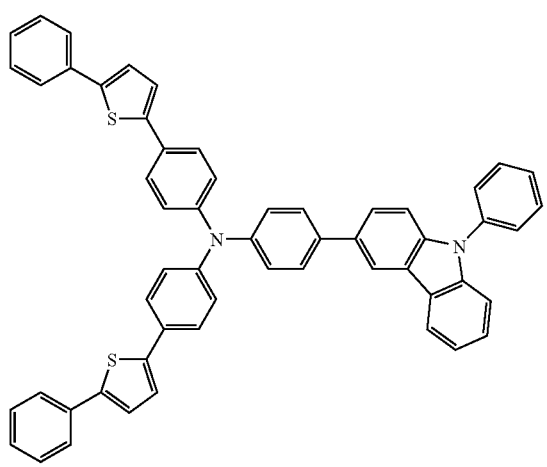
H44
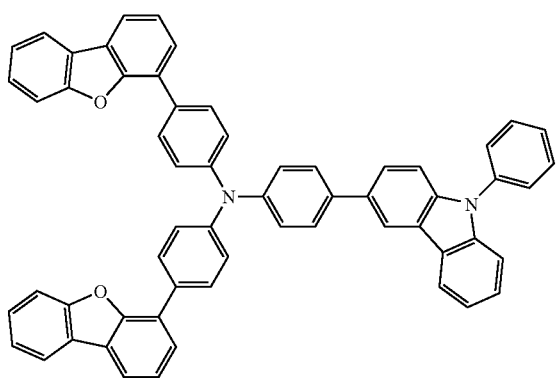

-continued
H45
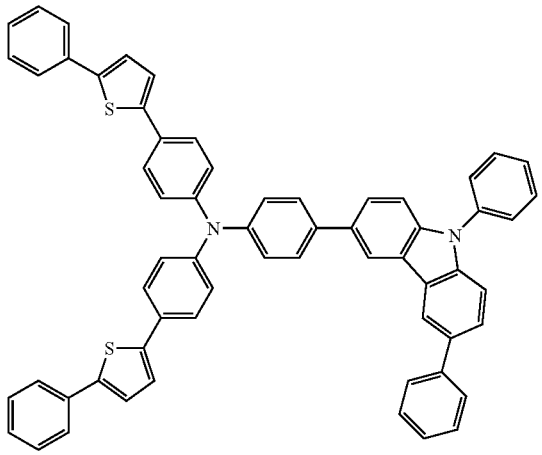
H46
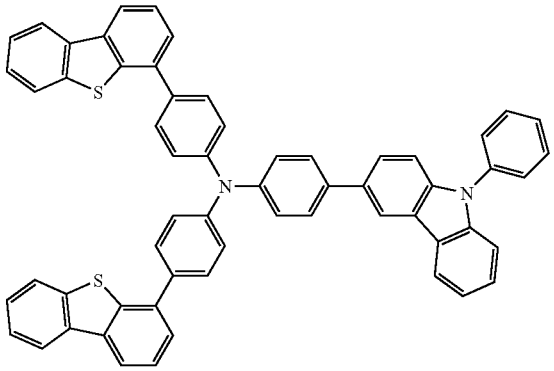
H47
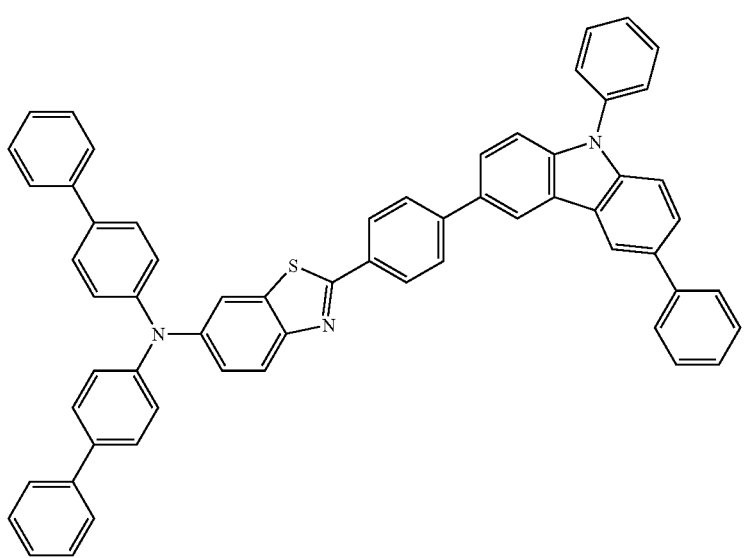
H48
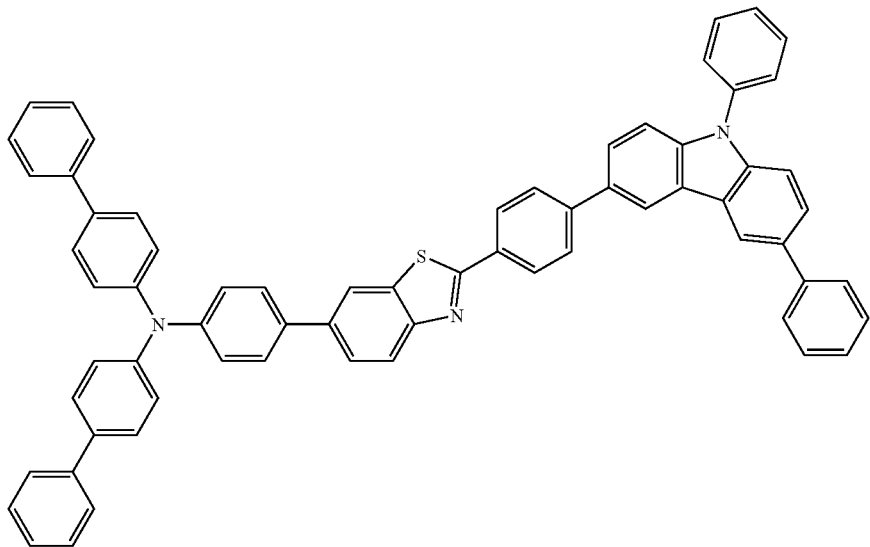

-continued
H49
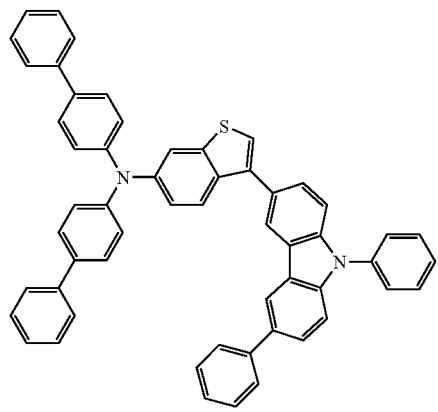
H50
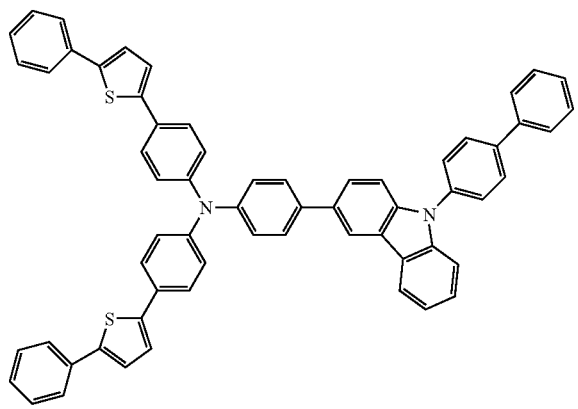
H51
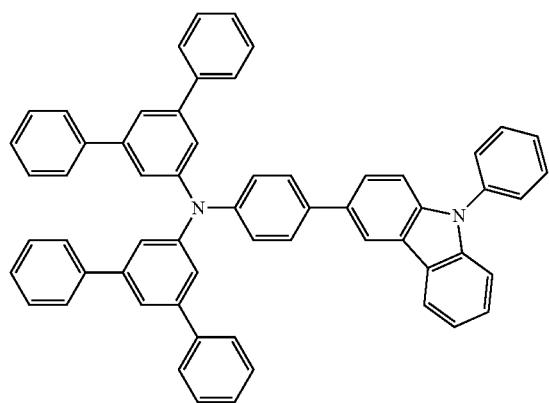
H52
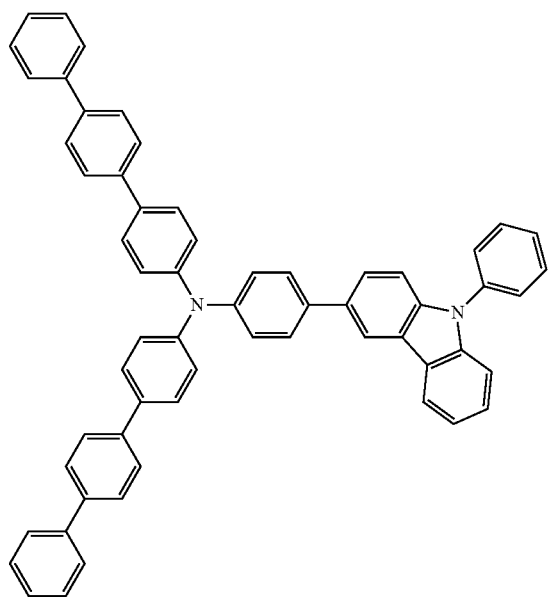
H53
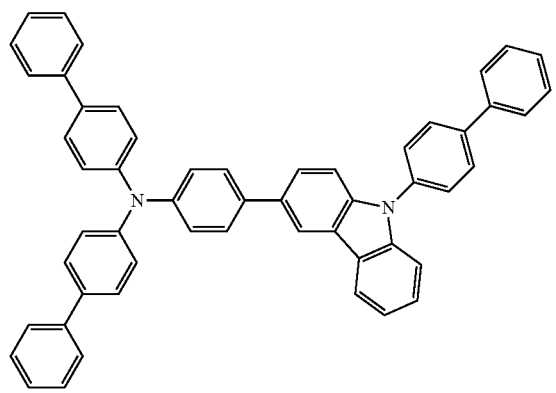
H54
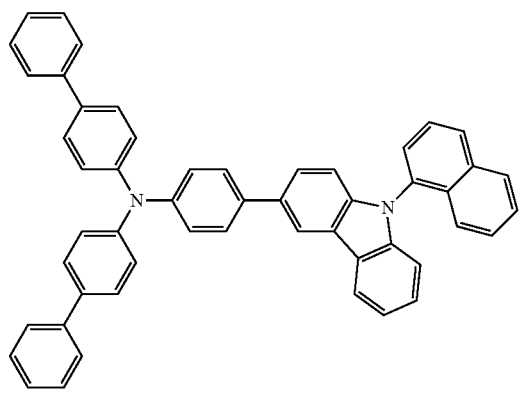

-continued
H55
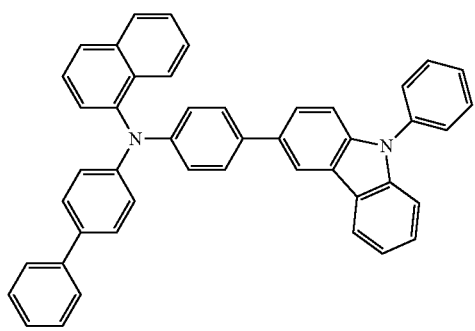
H56
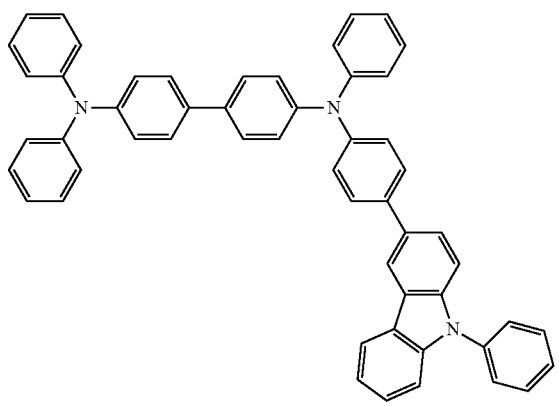
H57
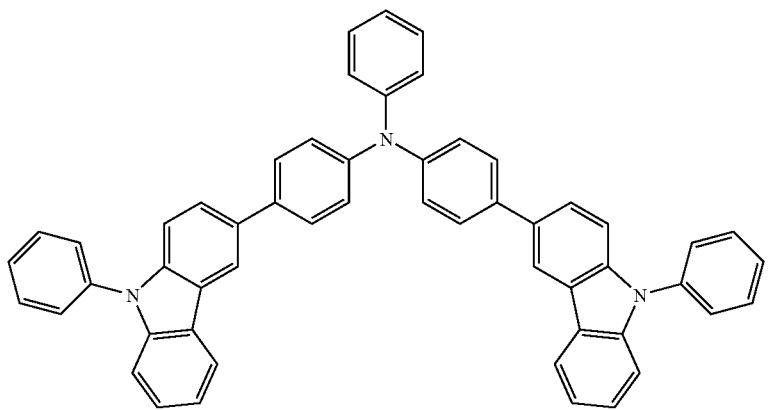
H58
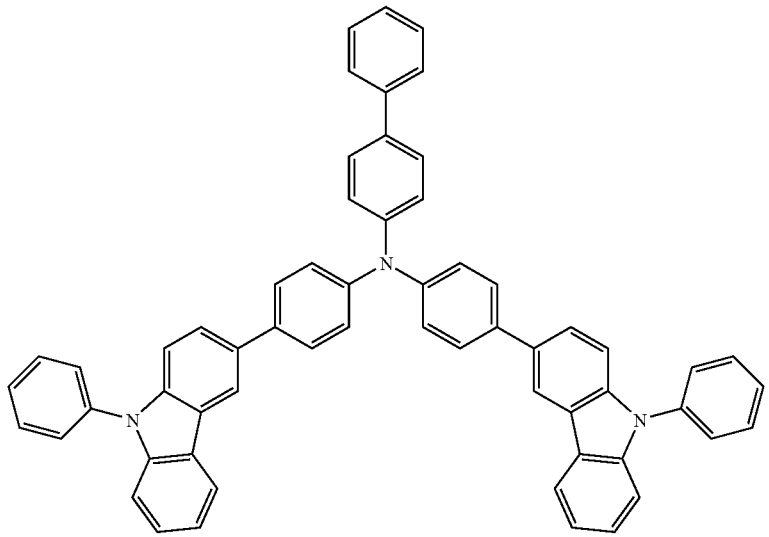

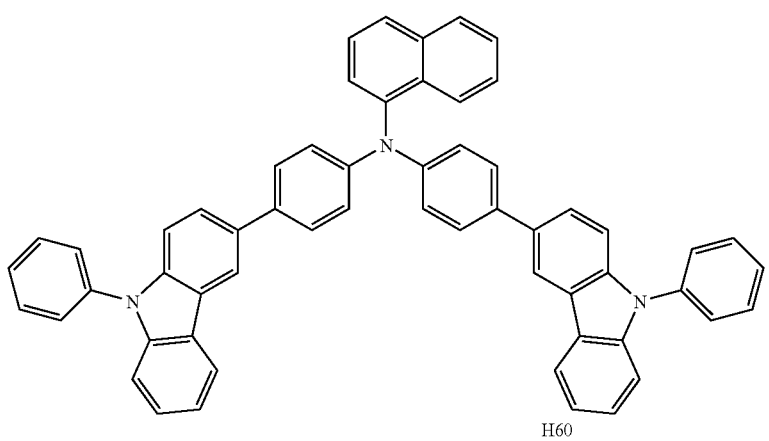

H59

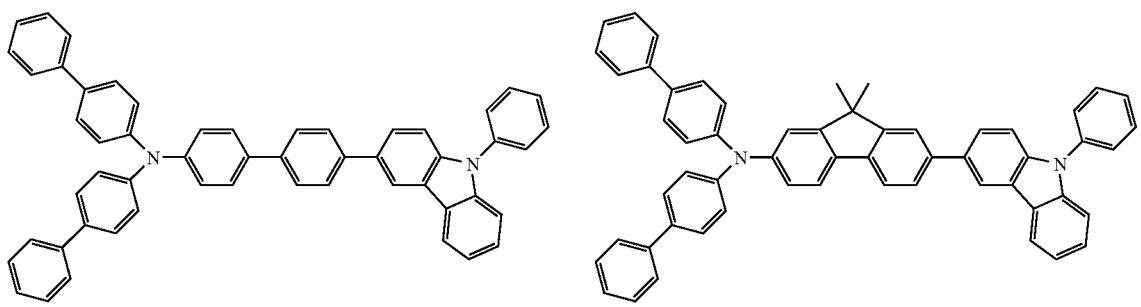

H60  H61

It is preferable that a number of the ring carbon atoms forming rings contained in the aromatic amine derivative of the present invention are 48 to 70.

It is preferable that the aromatic amine derivative of the present invention is a material for the organic EL devices, further preferable to be a hole transporting material for the organic EL devices.

It is preferable that the aromatic amine derivatives of the present invention are employed especially as materials for the organic EL devices that emit bluish light.

The organic EL device of the present invention is composed of one or more organic thin film layers including at least one light emitting layer and sandwiched between a cathode and an anode, wherein at least one of the organic thin film layers contains the aromatic amine derivative singly or in combination of two or more.

The above aromatic amine derivative includes preferable embodiments in the aromatic amine derivative of the present invention explained in the foregoing description.

It is preferable that the organic thin film layer in the organic EL device of the present invention includes a hole transporting layer and the hole transporting layer contains the aromatic amine derivative of the present invention. Moreover, it is also preferable that the organic thin film layer has a hole injecting layer and that the aromatic amine derivative of the present invention is contained in the hole injecting layer.

Moreover, it is preferable for the organic EL device of the present invention, that the above organic thin film layers have a hole transporting layer and/or a hole injecting layer, and it is further preferable that the aromatic amine derivative of the present invention is employed in the hole transporting layer or a hole injecting layer as a main component.

Furthermore, it is preferable that the light emitting layer in the organic EL device of the present invention contains an arylamine compound and/or a styrylamine compound.

It is preferable that the fluorescent dopant is a compound selected adjusting to a color of light emission from a group consisting of an amine-based compound, an aromatic compound, a chelate complex of tris(8-quinolinolat)aluminum complex or so, coumarin derivatives, tetraphenylbutadiene derivatives, bisstyrylarylene derivatives, oxadiazole derivatives, etc. Specific examples include an arylamine compound and an aryldiamine compound; among these, a styrylamine compound, a styryldiamine compound, an aromatic amine compound and an aromatic diamine compound are more preferable. Moreover, fused polycyclic aromatic compounds (except amine compound) are furthermore preferable. Those fluorescent dopants may be employable singly or in combination of two or more.

Preferred styrylamine compounds and styryldiamine compounds are represented by the following general formula (A):

(A)

(In the formula, $Ar_3$ represents a group selected from phenyl group, naphthyl group, biphenyl group, terphenyl group, stilbene group and distyrylaryl group; $Ar_4$ and $Ar_5$ each independently represents an aromatic hydrocarbon group having 6 to 20 carbon atoms; and $Ar_3$, $Ar_4$ and $Ar_5$ may be substituted. p represents an integer of 1 to 4, and preferably an integer of 1 or 2. Anyone of $Ar_3$ to $Ar_5$ is a group containing a styryl group. It is further preferable that the styryl group substitutes at least one of $Ar_4$ and $Ar_5$.)

Examples of the aromatic hydrocarbon group having 6 to 20 carbon atoms include phenyl group, naphthyl group, anthranyl group, phenanthryl group, terphenyl group, etc.

Preferred aromatic amine compounds and aromatic diamine compounds are represented by the following general formula (B):

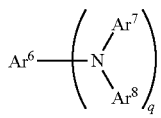

(In the formula, $Ar_6$ to $Ar_8$ each independently represents a substituted or unsubstituted aryl group having 5 to 40 carbon atoms forming the aromatic ring. q represents an integer of 1 to 4, and preferably an integer of 1 or 2.)

Examples of the aryl group having 5 to 40 carbon atoms forming the aromatic ring include phenyl group, naphthyl group, anthranyl group, phenanthryl group, pyrenyl group, coronyl group, biphenyl group, terphenyl group, pyrrolyl group, furanyl group, thiophenyl group, benzthiophenyl group, oxadiazolyl group, diphenylanthranyl group, indolyl group, carbazolyl group, pyridyl group, benzquinolyl group, fluoranthenyl group, acenaphthofluoranthenyl group, stilbene group, perilenyl group, crycenyl group, picenyl group, triphenylenyl group, rubicenyl group, benzanthracenyl group, phenylanthranyl group, bisanthracenyl group, or an aryl group represented by the following general formula (C) or (D); and preferably, naphthyl group, anthranyl group, crycenyl group, pyrenyl group, or an aryl group represented by the general formula (D).

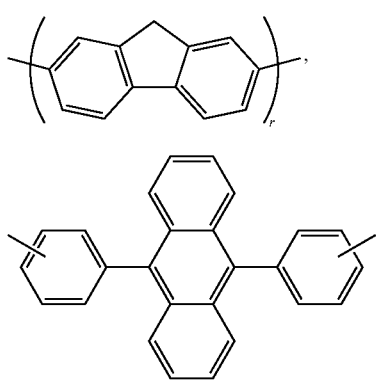

(In the general formula (C), r represents an integer of 1 to 3.)

Additionally, preferable examples of the substituent for the above aryl group include an alkyl group having 1 to 6 carbon atoms (an ethyl group, a methyl group, an i-propyl group, a n-propyl group, a s-butyl group, a t-butyl group, a pentyl group, a hexyl group, a cyclopentyl group, a cyclohexyl group, etc.); an alkoxy group having 1 to 6 carbon atoms (an ethoxy group, a methoxy group, an i-propoxy group, a n-propoxy group, a s-butoxy group, a t-butoxy group, a pentoxy group, a hexyloxy group, a cyclo pentoxy group, a cyclohexyl oxy group, etc.); an aryl group having 5 to 40 carbon atoms forming the aromatic ring; an amino group substituted with an aryl group having 5 to 40 carbon atoms forming the aromatic ring; an ester group which has an aryl group having 5 to 40 carbon atoms forming the aromatic ring; an ester group which has an alkyl group having 1 to 6 carbon atoms; a cyano group; a nitro group; and a halogen atom, etc.

Preferable fused polycyclic aromatic compounds (except amine compound) include fused polycyclic aromatic compounds such as naphthalene, anthracene, phenanthrene, pyrene, coronene, biphenyl, terphenyl, pyrrole, furan, thiophene, benzothiophene, oxadiazole, indole, carbazole, pyridine, benzoquinoline, fluoranthene, benzofluoranthene, acenaphthofluoranthene, stilbene, perylene, chrysene, picene, triphenylene, rubicene, benzoanthracene, etc., and those derivatives.

Following is a description regarding a device structure about the organic EL device of the present invention.

(I) Construction of the Organic EL Device

Typical examples of the construction in the organic EL device of the present invention are shown below.

(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an acceptor containing layer/a hole injecting layer/a hole transporting layer/a light emitting layer/an electron transporting layer/an electron injecting layer/a cathode;
(10) An anode/an insulating layer/a light emitting layer/an insulating layer/a cathode;
(11) An anode/an inorganic semiconductor layer/an insulating layer/a light emitting layer/an insulating layer/a cathode;
(12) An anode/an organic semiconductor layer/an insulating layer/a light emitting layer/an insulating layer/a cathode;
(13) An anode/an insulating layer/a hole injecting layer/a hole transporting layer/a light emitting layer/an insulating layer/a cathode; and
(14) An anode/an insulating layer/a hole injecting layer/a hole transporting layer/a light emitting layer/an electron injecting layer/a cathode.

Among the above constructions, construction (8) is usually preferable though not limited to.

Although the aromatic amine derivative of the present invention may be used to any organic thin film layer in the organic EL device, it is employable in the light emitting region or the hole transporting region, and a preferable embodiment of employing it into the hole transporting region, or a particularly preferable embodiment of employing it into a hole transporting layer will make crystallization of molecules hard to cause thereby enhancing yield of producing the organic EL device.

In the organic EL device of the present invention, the organic thin film layer preferably contains the aromatic amine derivative of the present invention in an amount of 30 to 100% by mole.

(II) Substrate which Transmits Light

In general, the organic EL device is fabricated on a substrate which transmits light. The substrate which transmits light is a substrate for supporting the organic EL device and preferably a flat and smooth substrate having a light transmittance of 50% or greater to visible light of 400 to 700 nm.

As the substrate which transmits light, for example, glass plate and synthetic resin plate are advantageously employed. Specific examples of the glass plate include soda ash glass, glass containing barium and strontium, lead glass, aluminosilicate glass, borosilicate glass, barium borosilicate glass and quartz. Specific examples of the synthetic resin plate include plate made of polycarbonate resins, acrylic resins, polyethylene telephthalate resins, polyether sulfide resins and polysulfone resins.

(III) Anode

The anode in the organic EL device of the present invention has a function of injecting holes into a hole transporting layer or a light emitting layer, and it is effective that the anode has a work function of 4.5 eV or greater. Specific examples of the material for the anode include indium tin oxide alloy (ITO), tin oxide (NESA), indium-zinc oxide alloy (IZO), gold, silver, platinum, copper, etc.

The anode can be prepared by forming a thin film of the electrode material described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundreds $\Omega/\square$ or smaller. The thickness of the anode is, in general, selected usually in the range of from 10 nm to 1 µm and preferably in the range of from 10 to 200 nm.

(IV) Light Emitting Layer

In the organic EL device of the present invention, the light emitting layer combines the following functions (1) to (3):
(1) The injecting function: the function of injecting holes from the anode or the hole injecting layer and injecting electrons from the cathode or the electron injecting layer when an electric field is applied;
(2) The transporting function: the function of transporting the injected charges (electrons and holes) by the force of the electric field; and
(3) The light emitting function: the function of providing the field for recombination of electrons and holes and promote the recombination to emit light.

Although there may be a difference between the capability of the holes being injected and the capability of the electrons being injected, and although there may be a difference between the transporting functions expressed by mobilities of the holes and the electrons, either one of the charges is preferable to be transferred.

As the process for forming the light emitting layer, a well-known process such as the vapor deposition process, the spin coating process and the LB process can be employed. It is particularly preferable for the light emitting layer to be a molecular deposit film. The molecular deposit film is a thin film formed by the deposition of a material compound in the gas phase or a thin film formed by the solidification of a material compound in a solution or liquid phase. In general, the molecular deposit film can be distinguished from the thin film formed in accordance with the LB process (the molecular accumulation film) based on the differences in the aggregation structure and higher order structures and functional differences caused by these structural differences.

In addition, as disclosed in JP 57-51781A, the light emitting layer can also be formed by dissolving a binder such as a resin and the material compounds into a solvent to prepare a solution, followed by forming a thin film from the prepared solution in accordance with the spin coating process or the like.

In the present invention, any well-known light emitting material other than the aromatic amine derivative of the present invention may be contained in the light emitting layer, or a light emitting layer containing any other well-known light emitting material may be laminated with the light emitting layer containing the aromatic amine derivative of the present invention, as long as the object of the present invention is not adversely affected.

Light emitting materials to be used for the light emitting layer together with the aromatic amine derivatives of the present invention includes, for example, anthracene, naphthalene, phenanthrene, pyrene, tetracene, coronene, chrysene, fluorescein, perylene, phthaloperylene, naphthaloperylene, perinone, phthaloperinone, naphthaloperinone, diphenylbutadiene, tetraphenylbutadiene, coumarin, oxadiazole, aldazine, bisbenzooxazoline, bisstyryl, pyrazine, cyclopentadiene, quinoline metal complex, aminoquinoline metal complex, benzoquinoline metal complex, imine, diphenylethylene, vinylanthracene, diaminecarbazol, pyran, thiopyran, polymethyne, merocyanine, imidazol chelate oxinoid compound, quinacridone, rubrene and fluorescent dye, but not limited thereto.

Preferable host materials to be used for the light emitting layer together with the aromatic amine derivatives of the present invention include compounds represented by following general formulae (i) to (xi).

An asymmetric anthracene represented by the following general formula (i):

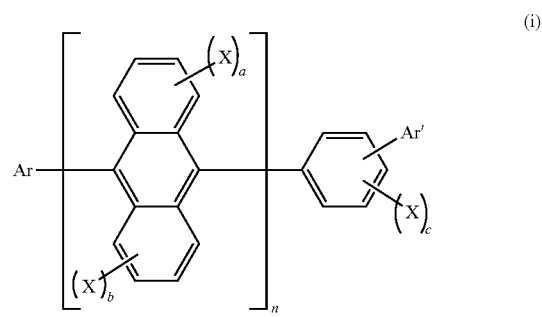

(In the above formula, Ar represents a substituted or unsubstituted fused aromatic group having 10 to 50 carbon atoms forming the aromatic ring; Ar' represents a substituted or unsubstituted aromatic group having 6 to 50 carbon atoms forming the aromatic ring; X represents a substituted or unsubstituted aromatic group having 6 to 50 carbon atoms forming the aromatic ring, a substituted or unsubstituted aromatic heterocyclic group having 5 to 50 atoms forming a ring, a substituted or unsubstituted alkyl group having 1 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a carboxyl group, a halogen atom, a cyano group, a nitro group or a hydroxyl group; a, b and c each represents an integer of 0 to 4; n represents an integer of 1 to 3; with the proviso that when n is an integer of 2 or greater, the plural groups within square brackets ([ ]) may be the same with or different from each other.)

An asymmetric monoanthracene derivative represented by the following general formula (ii):

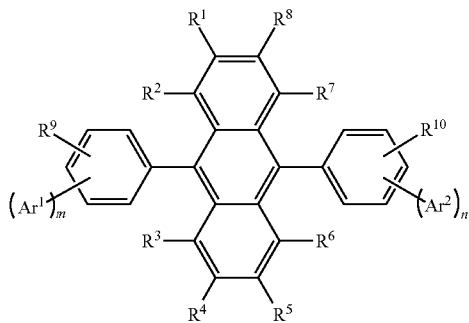

(In the formula, $Ar_1$ and $Ar_2$ each independently represents a substituted or unsubstituted aromatic ring group having 6 to 50 carbon atoms forming the aromatic ring; m and n each represents an integer of 1 to 4; with the proviso that in a case where m=n=1 and each bonding position of $Ar^1$ and $Ar^2$ to a benzene ring is bilaterally symmetric to each other, $Ar^1$ is different from $Ar^2$; and in a case where m or n represents an integer of 2 to 4, m is different from n; $R^1$ to $R^{10}$ each independently represents a hydrogen atom, a substituted or unsubstituted aromatic group having 6 to 50 carbon atoms forming the aromatic ring, a substituted or unsubstituted aromatic heterocyclic group having 5 to 50 atoms forming a ring, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxyl group, a halogen atom, a cyano group, a nitro group and a hydroxyl group.)

An asymmetric pyrene derivative represented by the following general formula (iii):

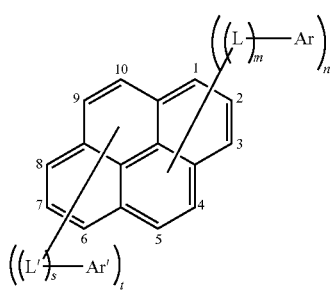

[In the formula, Ar and Ar' each represents a substituted or unsubstituted aromatic group having 6 to 50 carbon atoms forming the aromatic ring; L and L' each represents a substituted or unsubstituted phenylene group, a substituted or unsubstituted naphthalenylene group, a substituted or unsubstituted fluorenylene group or a substituted or unsubstituted dibenzosilolylene group; m represents an integer of 0 to 2, n represents an integer of 1 to 4, s represents an integer of 0 to 2 and t represents an integer of 0 to 4; L or Ar is bonded to any one of 1- to 5-positions of pyrene ring; and L' or Ar' is bonded to any one of 6- to 10-positions of pyrene ring;

with the proviso that when n+t represents an even number, Ar, Ar', L and L' satisfy the following conditions (1) or (2):

(1) Ar≠Ar' and/or L≠L' (wherein ≠ means that each group has a different structure)

(2) when Ar=Ar' and L=L'

(2-1) m≠s, and/or n≠t, or (2-2) when m=s and n=t, (2-2-1) L and L', or the pyrene ring, are respectively bonded to different positions of Ar and Ar', or (2-2-2) in the case where L and L', or the pyrene ring, are respectively bonded to the same position of Ar and Ar', the case where L and L', or Ar and Ar' are bonded to the 1- and 6-positions or 2- and 7-positions of the pyrene ring is excluded.]

An asymmetric anthracene derivative represented by the following general formula (iv):

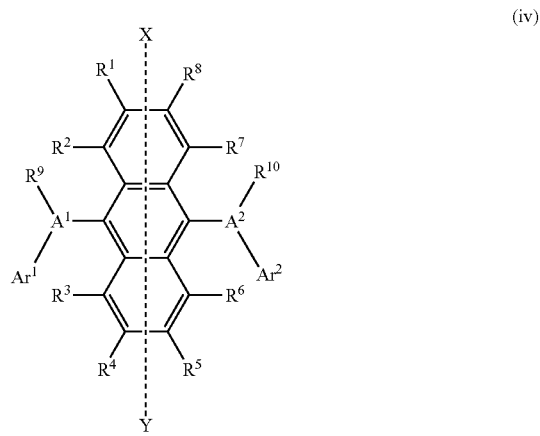

(In the formula, $A^1$ and $A^2$ each independently represents a substituted or unsubstituted fused aromatic ring group having 10 to 20 carbon atoms forming the aromatic ring; $Ar^1$ and $Ar^2$ each independently represents a hydrogen atom, or a substituted or unsubstituted aromatic ring group having 6 to 50 carbon atoms forming the aromatic ring.

$R^1$ to $R^{10}$ each independently represents a hydrogen atom, a substituted or unsubstituted aromatic group having 6 to 50 carbon atoms forming the aromatic ring, a substituted or unsubstituted aromatic heterocyclic group having 5 to 50 atoms forming a ring, a substituted or unsubstituted alkyl group having 1 to 50 carbon atoms, a substituted or unsubstituted cycloalkyl group, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxyl group, a halogen atom, a cyano group, a nitro group and a hydroxyl group.

The number of each of $Ar^1$, $Ar^2$, $R^9$ and $R^{10}$ may be two or more, and two neighboring groups thereof may form a saturated or unsaturated ring structure; with the proviso that the groups at 9- and 10-positions of the central anthracene are not symmetrical with respect to the X-Y axis.)

An anthracene derivative represented by the following general formula (v):

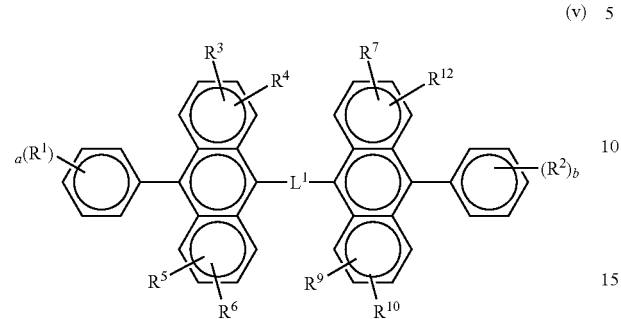

(In the formula, $R^1$ to $R^{10}$ each independently represents a hydrogen atom, an alkyl group, a cycloalkyl group, an aryl group which may be substituted, an alkoxyl group, an aryloxy group, an alkylamino group, an alkenyl group, an arylamino group or a heterocyclic group which may be substituted; and b each represents an integer of 1 to 5, and when each of a and b is 2 or greater, $R^1$'s or $R^2$'s may be the same or different, and $R^1$'s or $R^2$'s may bond each other to form a ring; each pair of $R^3$ and $R^4$, $R^5$ and $R^6$, $R^7$ and $R^8$, and $R^9$ and $R^{10}$ may bond each other to form a ring; $L^1$ represents a single bond, —O—, —S—, —N(R)—, an alkylene group or an arylene group wherein R represents an alkyl group or an aryl group which may be substituted.)

An anthracene derivative represented by the following general formula (vi):

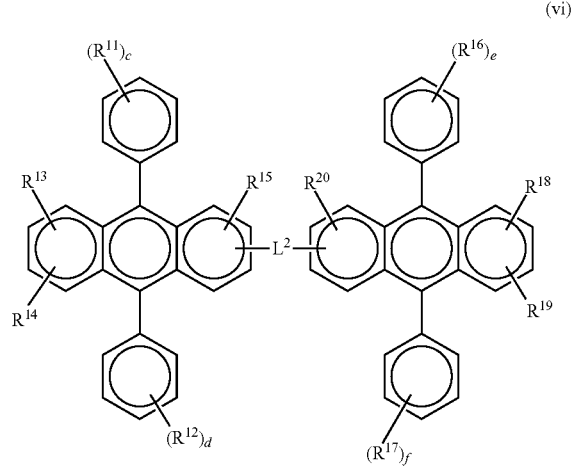

(In the formula, $R^{11}$ to $R^{20}$ each independently represents a hydrogen atom, an alkyl group, a cycloalkyl group, an aryl group, an alkoxyl group, an aryloxy group, an alkylamino group, an arylamino group or a heterocyclic group which may be substituted; c, d, e and f each represents an integer of 1 to 5, and when each of c, d, e and f is 2 or greater, $R^{11}$'s, $R^{12}$'s, $R^{16}$'s or $R^{17}$'s may be the same or different, and $R^{11}$'s, $R^{12}$'s, $R^{16}$'s or $R^{17}$'s may bond each other to form a ring; each pair of $R^{13}$ and $R^{14}$, and $R^{18}$ and $R^{19}$ may bond each other to form a ring; $L^2$ represents a single bond, —O—, —S—, —N(R)—, an alkylene group or an arylene group wherein R represents an alkyl group or an aryl group which may be substituted.)

A spirofluorene derivative represented by the following general formula (vii):

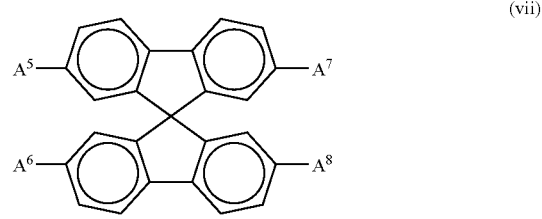

(In the formula, $A^5$ to $A^8$ each independently represents a substituted or unsubstituted biphenylyl group or a substituted or unsubstituted naphthyl group.)

A compound containing a fused ring represented by a following general formula (viii):

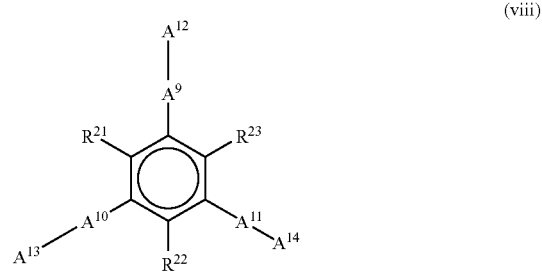

(In the formula, $A^9$ to $A^{14}$ are the same as described above, and $R^{21}$ to $R^{23}$ each independently represents a hydrogen atom, an alkyl group having 1 to 6 carbon atoms, a cycloalkyl group having 3 to 6 carbon atoms, an alkoxyl group having 1 to 6 carbon atoms, an aryloxy group having 5 to 18 carbon atoms, an aralkyloxy group having 7 to 18 carbon atoms, an arylamino group having 5 to 16 carbon atoms, a nitro group, a cyano group, an ester group having 1 to 6 carbon atoms or a halogen atom; and at least one of $A^9$ to $A^{14}$ represents a fused aromatic ring having 3 or more rings.)

A fluorene compound represented by the following general formula (ix):

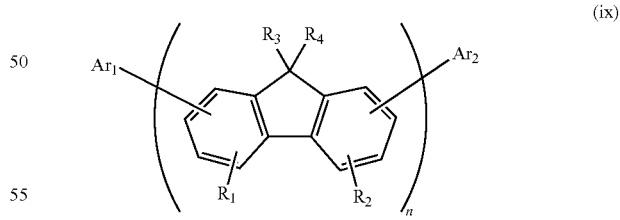

(In the formula, $R_1$ and $R_2$ each independently represents a hydrogen atom, a substituted or unsubstituted alkyl group, a substituted or unsubstituted aralkyl group, a substituted or unsubstituted aryl group, a substituted or unsubstituted heterocyclic group, a substituted amino group, a cyano group or a halogen atom; $R_1$'s and $R_2$'s bonding to different fluorene groups may be respectively the same or different, and $R_1$ and $R_2$ bonding to the same fluorene group may be the same or different; $R_3$ and $R_4$ each independently represents a hydrogen atom, a substituted or unsubstituted alkyl group, a substituted or unsubstituted aralkyl group, a substituted or unsubstituted aryl group, or a substituted or unsubstituted heterocyclic group, and $R_3$'s and $R_4$'s bonding to different fluorene groups may be respectively the same or different, and $R_3$ and $R_4$ bonding to the same fluorene group may be the same or different; $Ar_1$ and $Ar_2$ each independently represents a substituted or unsubstituted fused polycyclic aromatic group consisting of benzene rings of 3 or more or a substituted or unsubstituted fused polycyclic heterocyclic group consisting of benzene rings and hetero rings of 3 or more in total; and further, $Ar_1$ and $Ar_2$ may be the same with, or different from each other; and n represents an integer of 1 to 10.)

A compound having anthracene central skeleton represented by the following general formula (x):

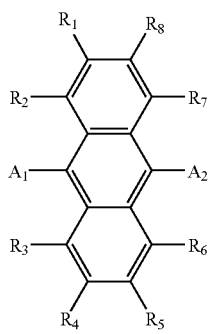

(x)

(In the formula (x), $A_1$ and $A_2$ each independently represents a group derived from a substituted or unsubstituted aromatic ring having 6 to 20 carbon atoms. One or more substituents may substitute the aromatic ring.

The substituent is selected among a substituted or unsubstituted aryl group having 6 to 50 carbon atoms forming the aromatic ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxyl group, a halogen atom, a cyano group, a nitro group and a hydroxyl group.

When two or more substituents substitute the aromatic ring, the substituents may be the same with or different from each other, and adjacent substituents may bond each other to form a saturated or unsaturated cyclic structure.

$R_1$ to $R_8$ each independently selectively represents a hydrogen atom, a substituted or unsubstituted aryl group having 6 to 50 carbon atoms forming the aromatic ring, a substituted or unsubstituted heteroaryl group having 5 to 50 atoms forming a ring, a substituted or unsubstituted alkyl group having 1 to 50 carbon atoms, a substituted or unsubstituted cycloalkyl group having 3 to 50 carbon atoms, a substituted or unsubstituted alkoxy group having 1 to 50 carbon atoms, a substituted or unsubstituted aralkyl group having 6 to 50 carbon atoms, a substituted or unsubstituted aryloxy group having 5 to 50 atoms forming a ring, a substituted or unsubstituted arylthio group having 5 to 50 atoms forming a ring, a substituted or unsubstituted alkoxycarbonyl group having 1 to 50 carbon atoms, a substituted or unsubstituted silyl group, a carboxyl group, a halogen atom, a cyano group, a nitro group and a hydroxyl group.)

A compound represented by the following general formula (xi) in which $A_1$ and $A_2$ are groups different from each other defined in the above general formula (x).

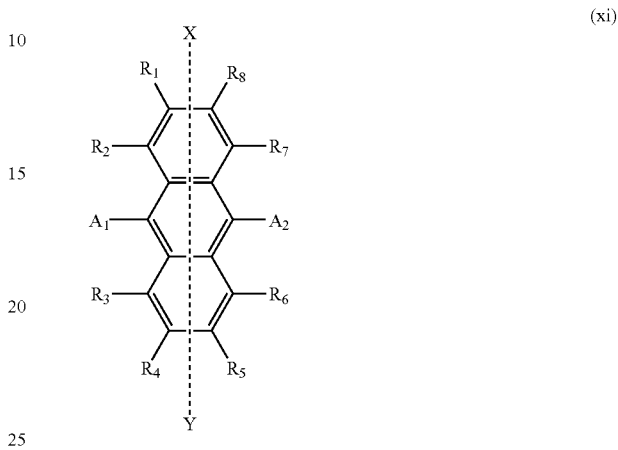

(xi)

(In the formula (xi), $A_1$, $A_2$ and $R_1$ to $R_8$ each independently represents the same as defined in the general formula (x) respectively; with the proviso that the groups at 9- and 10-positions of the central anthracene are not symmetrical with respect to the X-Y axis.)

Among the above host materials, an anthracene derivative is preferable and a monoanthracene derivative is more preferable, further an asymmetric anthracene is particularly preferable.

In addition, a phosphorescent compound may be employed as a light emitting material for dopant. A compound containing a carbazole ring for a host material is preferable as the phosphorescent compound. The dopant is not limited as long as it is a compound capable of emitting light from triplet exciton, and preferably a metal complex containing at least one metal selected from the group consisting of Ir, Ru, Pd, Pt, Os and Re, more preferably a porphyrin metal complex or an ortho-metallated complex. A suitable host for phosphorescence composed of a compound containing a carbazole ring is a compound having a function of making the phosphorescent compound to emit light by the energy transfer from its excitation state to the phosphorescent compound. The host compound is not limited as long as capable of transferring the exciton energy to the phosphorescent compound and may be appropriately selected according to the purpose. The host compound may have any group such as a hetero ring in addition to the carbazole ring.

Specific examples of the host compound include a carbazole derivative, a triazole derivative, an oxazole derivative, an oxadiazole derivative, an imidazole derivative, a polyarylalkane derivative, a pyrazoline derivative, a pyrazlone derivative, a phenylenediamine derivative, an arylamine derivative, a calcone derivative substituted by amino group, a styrylanthracene derivative, a fluorenone derivative, a hydrazone derivative, a stilbene derivative, a silazane derivative, an aromatic tertiary amine compound, a styrylamine compound, an aromatic dimethylidene compound, a porphyrin-based compound, an anthraquinodimethane derivative, an anthrone derivative, a diphenylquinone derivative, a thiopyrandioxide derivative, a carbodimide derivative, a fluorenylidene methane derivative, a distyrylpyrazine derivative, heterocyclic tetracarboxylic anhydride such as a naphthaleneperylene, a phthalocyanine derivative, various metal complex polysilane compound such as a metal complex of 8-quinolinol derivative and a metal complex having a ligand of metallophthalocyanine, benzoxazole or benzothiazole, an electrically conductive polymeric oligomer such as a poly(N-vinylcarbazole) derivative, an aniline copolymer, a thiophene oligomer and a polythiophene, polymer compound such as a polythiophene derivative, a polyphenylene derivative, a polyphenylenevinylene derivative and a polyfluorene derivative. The host compound may be used alone or in combination of two or more.

More specific examples include the following:

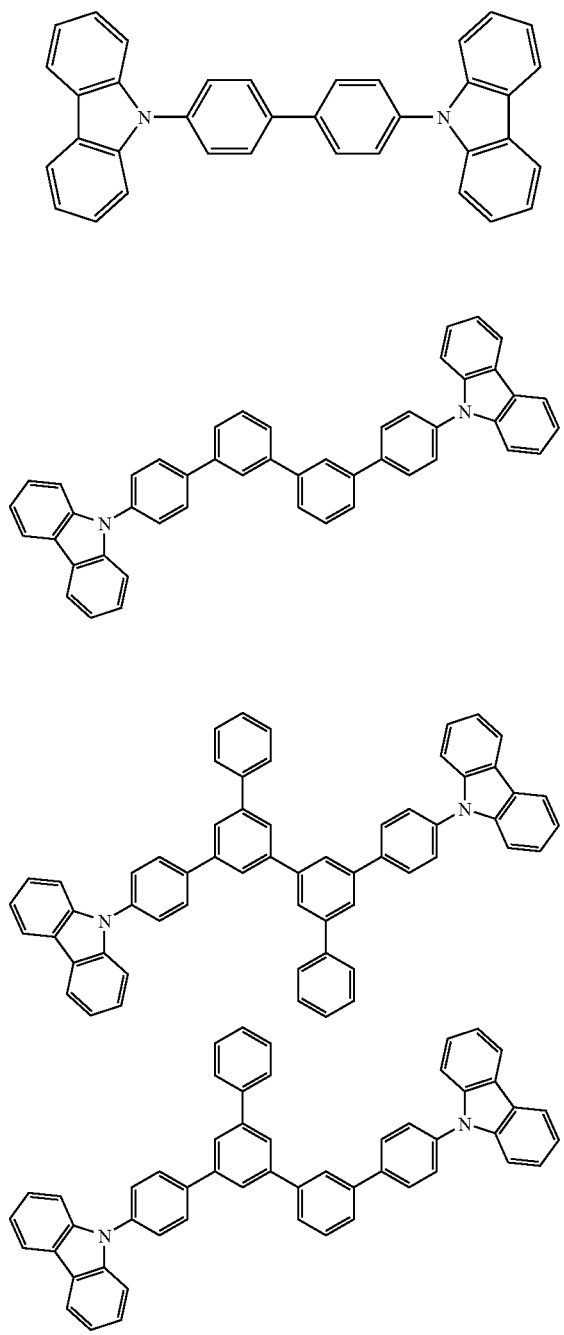

-continued

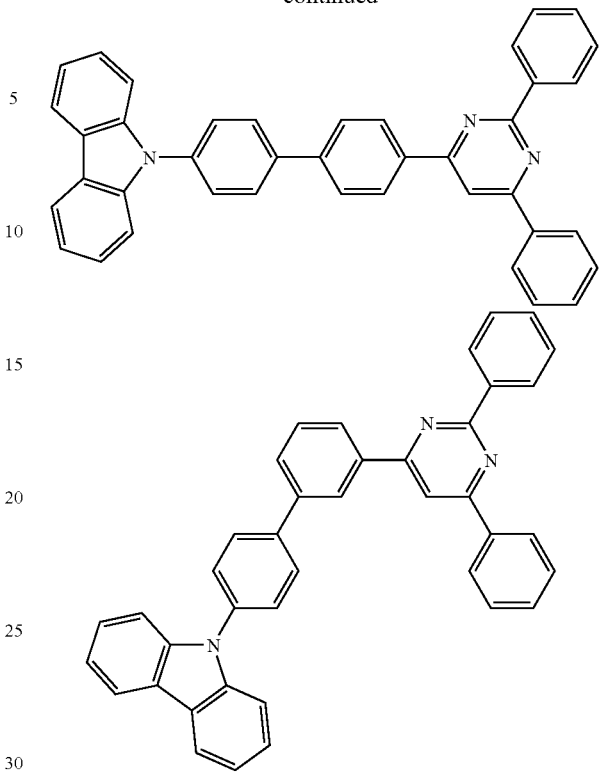

The phosphorescent dopant is a compound capable of emitting light from the triplet exciton. The phosphorescent dopant is not restricted as long as it emits light from the triplet exciton, and preferably a metal complex containing at least one metal selected from the group consisting of Ir, Ru, Pd, Pt, Os and Re, more preferably a porphyrin metal complex or an ortho-metallated metal complex. As the porphyrin metal complex, a porphyrin platinum complex is preferable. The phosphorescent compound may be used alone or in combination of two or more.

There are various ligands to form the ortho-metallated metal complex, and preferred are 2-phenylpyridine derivatives, 7,8-benzoquinoline derivatives, 2-(2-thienyl)pyridine derivatives, 2-(1-naphthyl)pyridine derivatives, and 2-phenylquinoline derivatives, etc. The derivatives may have a substituent as occasion demands. In particular, a dopant introduced with a fluorine atom or a trifluoromethyl group is preferable for the blue light emission. In addition, a ligand other than the above ligands such as acetylacetonate and picric acid may be introduced as a co-ligand.

The amount of the phosphorescent dopant in the light emitting layer may be selected for the objective as appropriate without particularly restricted, and for example, it may be selected in the range of from 0.1 to 70% by mass, preferably in the range of from 1 to 30% by mass. The emission is faint and the advantage is not demonstrated when the amount is less than 0.1% by mass. The concentration quenching becomes noticeable so that the device performance is deteriorated when the amount exceeds 70% by mass.

Further, the light emitting layer may contain a hole transporting material, a electron transporting material or a polymer binder, if necessary.

The thickness of the light emitting layer is, in general, selected in the range of from 5 to 50 nm, preferably in the range of from 7 to 50 nm and the most preferably in the range of from 10 to 50 nm. It is resulted in difficult to form the light emitting layer and to control chromaticity thereof when the thickness is thinner than 5 nm, and it may be resulted in possibility of elevating driving voltage when it exceeds 50 nm, (V) Hole Injecting and Transporting Layer (Hole Transporting Region)

The hole injecting and transporting layer is a layer which helps the injection of holes into the light emitting layer and transports the holes to the light emitting region. The layer exhibits a great mobility of holes and, in general, has an ionization energy as small as 5.6 eV or smaller. For the hole injecting and transporting layer, a material which transports holes to the light emitting layer at a small strength of the electric field is preferable. A material which exhibits, for example, a mobility of holes of at least $10^{-4}$ cm$^2$/V·sec under an electric field of from $10^4$ to $10^6$ V/cm is preferable.

When the aromatic amine derivative of the present invention is employed in the hole transporting region, the hole injecting and transporting layer may be composed of the aromatic amine derivative of the present invention alone or in combination with another material.

When the aromatic amine derivative of the present invention is employed in the hole transporting layer, other materials may be employed in the hole injecting layer, and when the aromatic amine derivative of the present invention is employed in the hole injecting layer, other materials may be employed in the hole transporting layer.

With regard to the material which may be employed for forming the hole injecting and transporting layer in combination with the aromatic amine derivative of the present invention, any material having the foregoing preferable properties is employed without particularly restricted, which is selected from compounds commonly used as a hole transporting material of photoconductive materials and compounds used for forming the hole injecting and transporting layer of EL devices. In the present invention, a material capable of transporting holes and being employable in a transporting region is defined as a hole transporting material.

Specific examples include triazole derivatives (refer to U.S. Pat. No. 3,112,197, etc.), oxadiazole derivatives (refer to U.S. Pat. No. 3,189,447, etc.), imidazole derivatives (refer to JP-B 37-16096, etc.), polyarylalkane derivatives (refer to U.S. Pat. Nos. 3,615,402; 3,820,989; 3,542,544, JP-B 45-555, JP-B 51-10983, JP 51-93224A, JP 55-17105A, JP 56-4148A, JP 55-108667A, JP 55-156953A, JP 56-36656A, etc.), pyrazoline derivatives and pyrazolone derivatives (refer to U.S. Pat. Nos. 3,180,729; 4,278,746; JP 55-88064A, JP 55-88065A, JP 49-105537A, JP 55-51086A, JP 56-80051A, JP 56-88141A, JP 57-45545A, JP 54-112637A, JP 55-74546A, etc.), phenylenediamine derivatives (refer to U.S. Pat. No. 3,615,404; JP-B 51-10105, JP-B 46-3712, JP-B 47-25336, JP 54-119925A, etc.), arylamine derivatives (refer to U.S. Pat. Nos. 3,567,450; 3,240,597; 3,658,520; 4,232, 103; 4,175,961; 4,012,376; JP-B 49-35702, JP-B 39-27577, JP 55-144250A, JP 56-119132A, JP 56-22437A, German Patent No. 1,110,518, etc.), amino-substituted chalcone derivatives (refer to U.S. Pat. No. 3,526,501, etc.), oxazole derivatives (disclosed in U.S. Pat. No. 3,257,203, etc.), styrylanthracene derivatives (refer to JP 56-46234A, etc.), fluorenone derivatives (refer to JP 54-110837A, etc.), hydrazone derivatives (refer to U.S. Pat. No. 3,717,462, JP 54-59143A, JP 55-52063A, JP 55-52064A, JP 55-46760A, JP 57-11350A, JP 57-148749A, JP 2-311591A, etc.), stilbene derivatives (refer to JP 61-210363A, JP 61-228451A, JP 61-14642A, JP 61-72255A, JP 62-47646A, JP 62-36674A, JP 62-10652A, JP 62-30255A, JP 60-93455A, JP 60-94462A, JP 60-174749A, JP 60-175052A, etc.), silazane derivatives (U.S. Pat. No. 4,950,950), polysilane-based polymer (JP 2-204996A), aniline-based copolymer (JP 2-282263A), etc.

With regard to the material for the hole injecting and transporting layer, the above materials are also employable, and porphyrin compounds (disclosed in JP 63-2956965A), aromatic tertiary amine compounds and styryl amine compounds (refer to U.S. Pat. No. 4,127,412, JP 53-27033A, JP 54-58445A, JP 55-79450A, JP 55-144250A, JP 56-119132A, JP 61-295558A, JP 61-98353A, JP 63-295695A, etc.) are preferable and the aromatic tertiary amine compounds are particularly preferable.

Further examples include, 4,4'-bis(N-(1-naphthyl)-N-phenylamino)biphenyl (NPD) which has 2 fused aromatic rings in its molecule described in U.S. Pat. Nos. 5,061,569 and 4,4',4"-tris(N-(3-methylphenyl)-N-phenylamino)triphenylamine (MTDATA) described in JP 4-308688A which includes three triphenylamine units connected in a star burst configuration.

Besides, a compound with heterocyclic derivative structure having a nitrogen atom expressed with a following general formula disclosed in Japanese Registered Patent No. 03571977 is also employable.

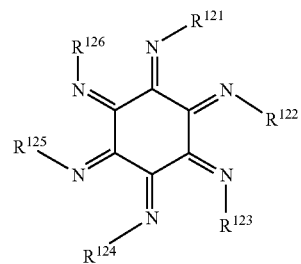

In the formula, $R^{121}$ to $R^{126}$ each independently represents any one of a substituted or unsubstituted alkyl group, a substituted or unsubstituted aryl group, a substituted or unsubstituted aralkyl group or a substituted or unsubstituted heterocyclic group. However, $R^{121}$ to $R^{126}$ may be the same with or different from each other. Further, both $R^{121}$ and $R^{122}$, both $R^{123}$ and $R^{124}$, both $R^{125}$ and $R^{126}$, both $R^{121}$ and $R^{126}$, both $R^{122}$ and $R^{123}$ or both $R^{124}$ and $R^{125}$ may form a fused ring).

Still further, a compound expressed with a following general formula disclosed in US Patent Application Publication No. 2004/0113547 is also employable.

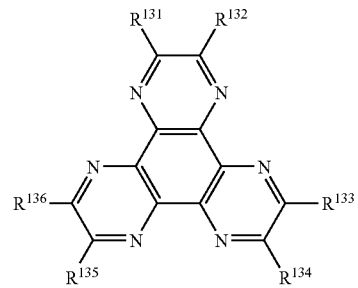

(In the formula, $R^{131}$ to $R^{136}$ are substituents, and preferably, they each independently represents an electron withdrawing group such as a cyano group, a nitro group, a sulfonyl group, a carbonyl group, a trifluoromethyl group, a halogen atom, etc.)

Typically exemplified as those materials, a material having an acceptor property is also employable as a hole injecting material. Specific examples of those are the same as described above.

In addition to the above-mentioned aromatic dimethylidene compound described as a material for the light emitting layer, inorganic compound such as p-type Si and p-type SiC may be used as the material for the hole injecting and transporting layer.

To form the hole injecting and transporting layer, a thin film may be formed from the aromatic amine derivative of the present invention in accordance with a well-known process such as the vacuum vapor deposition process, the spin coating process, the casting process and the LB process. Although the thickness of the hole injecting and transporting layer is not particularly limited, the thickness is usually from 5 nm to 5 μm. The hole injecting and transporting layer may be a single layer made of one or more kinds of materials mentioned above or may be laminated with another hole injecting and transporting layer made of a different material, as long as the hole injecting and transporting layer contains the aromatic amine derivative of the present invention in its hole transporting region.

An organic semiconductor layer which preferably has an electric conductance of $10^{-10}$ S/cm or greater may be provided to assist the injection of holes or electrons into the light emitting layer. Examples of the materials for the organic semiconductor layer include electrically conductive oligomers such as an oligomer having thiophene and an oligomer having arylamine disclosed in JP 8-193191A; and electrically conductive dendrimers such as a dendrimer having an arylamine dendrimer.

(VI) Electron Injecting and Transporting Layer

The electron injecting and transporting layer is a layer having a great electron mobility, which assists the injection of electrons into the light emitting layer and transports them to a light emitting region. Among the electron injecting layers, the adhesion improving layer is a layer made of a material exhibiting excellent adhesion to the cathode.

Further, it is known that because the emitted light reflects on the electrode (cathode in this case) in the organic EL device, the light taken out directly through the anode and the light taken out after the reflection on the electrode interferes each other. To utilize the interference effect effectively, the thickness of the electron transporting layer is appropriately selected from several nm to several μm. When the film is thicker, the hole mobility is preferably at least $10^{-5}$ cm$^2$/V·s under an electric field of from $10^4$ to $10^6$ V/cm for avoiding the elevation of driving voltage.

As the material for the electron injecting layer, metal complexes of 8-hydroxyquinoline or derivatives thereof and oxadiazole derivatives are preferable. Examples of the metal complexes of 8-hydroxyquinoline and derivatives thereof include metal chelate oxinoid compounds including chelates of oxine (in general, 8-quinolinol or 8-hydroxyquinoline), for example, tris(8-quinolinol)aluminum.

Examples of the oxadiazole derivatives include an electron transfer compound represented by the following general formulae:

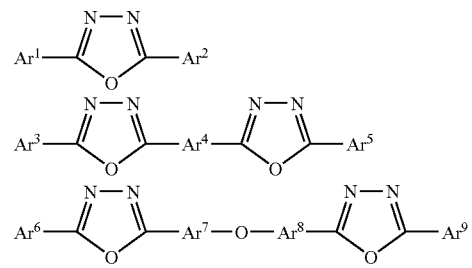

(In the formula, Ar$^1$, Ar$^2$, Ar$^3$, Ar$^5$, Ar$^6$ and Ar$^9$ may be the same or different and each independently represents a substituted or unsubstituted aryl group; Ar$^4$, Ar$^7$ and Ar$^8$ may be the same or different and each independently represents a substituted or unsubstituted arylene group.)

Examples of aryl group include a phenyl group, a biphenyl group, an anthryl group, a perilenyl group and a pyrenyl group. Examples of the arylene group include a phenylene group, a naphthylene group, a biphenylene group, an anthrylene group, a perilenylene group, a pyrenylene group, etc. Examples of the substituent include an alkyl group having 1 to 10 carbon atoms, an alkoxy group having 1 to 10 carbon atoms and a cyano group. The electron transfer compound is preferably a thin-film forming compound.

Specific examples of the electron transfer compounds are shown below:

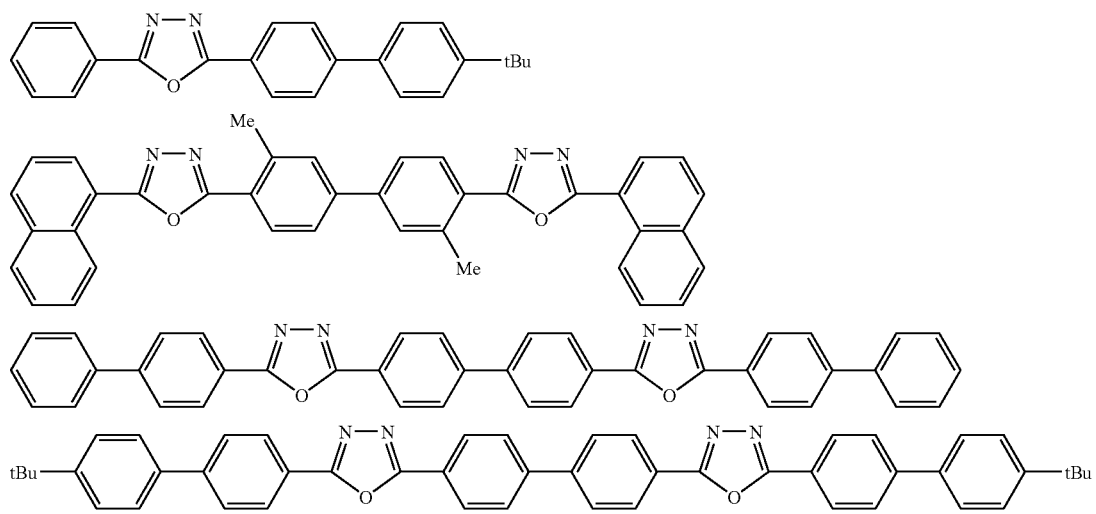

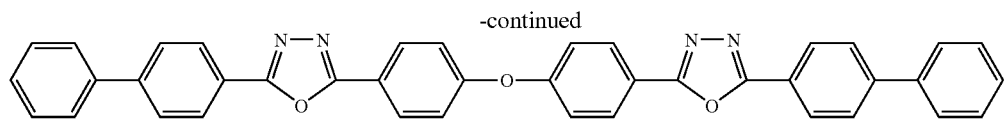

Further, materials shown by following general formulae (A) to (F) are employable for the electron injecting layer and the electron transporting layer.

A nitrogen-containing heterocyclic derivative represented by the following general formula (A) or (B):

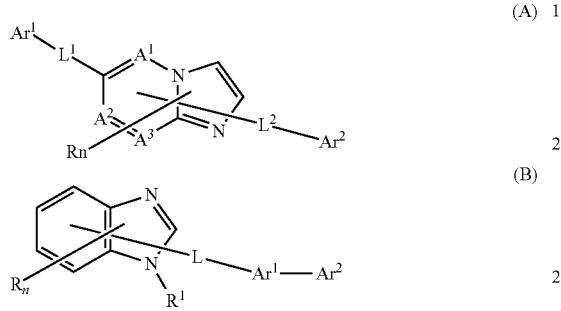

(In the general formulae (A) and (B), $A^1$ to $A^3$ each independently represents a nitrogen atom or a carbon atom; $Ar^1$ in the general formula (A) represents a substituted or unsubstituted aryl group having 6 to 60 carbon atoms forming the aromatic ring or a substituted or unsubstituted heteroaryl group having 3 to 60 atoms forming a ring; $Ar^1$ in the general formula (B) represents a divalent group of $Ar^1$ in the general formula (A); $Ar^2$ represents a hydrogen atom, a substituted or unsubstituted aryl group having 6 to 60 carbon atoms forming the aromatic ring, a substituted or unsubstituted heteroaryl group having 3 to 60 atoms forming a ring, a substituted or unsubstituted alkyl group having 1 to 20 carbon atoms, a substituted or unsubstituted alkoxy group having 1 to 20 carbon atoms or those divalent groups. At least one of $Ar^1$ and $Ar^2$ represents a substituted or unsubstituted fused ring group having 10 to 60 ring carbon atoms, a substituted or unsubstituted monohetero fused ring group having 3 to 60 ring carbon atoms, or those divalent groups.

$L^1$, $L^2$ and L each independently represents a single bond, a substituted or unsubstituted arylene group having 6 to 60 carbon atoms forming the aromatic ring, a substituted or unsubstituted heteroarylene group having 3 to 60 atoms forming a ring or a substituted or unsubstituted fluorenylene group.

R represents a hydrogen atom, a substituted or unsubstituted aryl group having 6 to 60 carbon atoms forming the aromatic ring, a substituted or unsubstituted heteroaryl group having 3 to 60 atoms forming a ring, a substituted or unsubstituted alkyl group having 1 to 20 carbon atoms, or a substituted or unsubstituted alkoxy group having 1 to 20 carbon atoms; n represents an integer of 0 to 5; when n is 2 or greater, Rs may be the same or different and adjacent couple of Rs may bond to form a carbocyclic aliphatic ring or a carbocyclic aromatic ring.

$R^1$ represents a hydrogen atom, a substituted or unsubstituted aryl group having 6 to 60 carbon atoms forming the aromatic ring, a substituted or unsubstituted heteroaryl group having 3 to 60 atoms forming a ring, a substituted or unsubstituted alkyl group having 1 to 20 carbon atoms, or a substituted or unsubstituted alkoxy group having 1 to 20 carbon atoms or -L-$Ar^1$—$Ar^2$.)

A nitrogen-containing heterocyclic derivative represented by a following general formula (C):

$$\text{HAr-L-Ar}^1\text{—Ar}^2 \quad (C)$$

(In the formula, HAr represents a nitrogen-containing heterocyclic group having 3 to 40 carbon atoms which may have a substituent; L represents a single bond, an arylene group having 6 to 60 carbon atoms which may have a substituent, a heteroarylene group having 3 to 60 carbon atoms which may have a substituent; $Ar^1$ represents a divalent aromatic hydrocarbon group having 6 to 60 carbon atoms which may have a substituent; and $Ar_2$ represents an aryl group having 6 to 60 carbon atoms which may have a substituent or a heteroaryl group having 3 to 60 carbon atoms which may have a substituent.)

A silacyclopentadiene derivative represented by a following general formula (D):

(In the formula, X and Y each independently represents a saturated or unsaturated hydrocarbon group having 1 to 6 carbon atoms, an alkoxy group, an alkenyloxy group, an alkynyloxy group, a hydroxy group, a substituted or unsubstituted aryl group, or a substituted or unsubstituted hetero ring, or X and Y represents a saturated or unsaturated ring by bonding to each other; $R_1$ to $R_4$ each independently represents a hydrogen atom, a halogen atom, a substituted or unsubstituted alkyl group having 1 to 6 carbon atoms, an alkoxy group, an aryloxy group, a perfluoroalkyl group, a perfluoroalkoxy group, an amino group, an alkylcarbonyl group, an arylcarbonyl group, an alkoxycarbonyl group, an aryloxycarbonyl group, an azo group, an alkylcarbonyloxy group, an arylcarbonyloxy group, an alkoxycarbonyloxy group, an aryloxycarbonyloxy group, a sulfinyl group, a sulfonyl group, a sulfanyl group, a silyl group, a carbamoyl group, an aryl group, a hetero ring group, an alkenyl group, an alkynyl group, a nitro group, a formyl group, a nitroso group, a formyloxy group, an isocyano group, a cyanate group, an isocyanate group, a thiocyanate group, an isothiocyanate group, or a cyano group, or an adjacent pair of $R_1$ to $R_4$ represents a substituted or unsubstituted fused ring.)

A borane derivative represented by the following general formula (E):

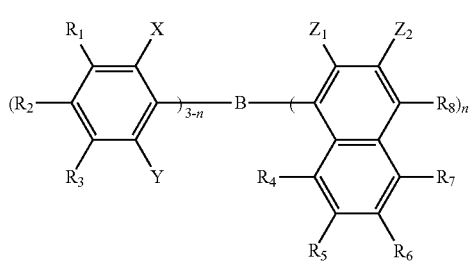
(E)

(In the formula, $R_1$ to $R_8$ and $Z_2$ each independently represents a hydrogen atom, a saturated or unsaturated hydrocarbon group, an aromatic group, a hetero ring group, substituted amino group, a substituted boryl group, an alkoxy group or an aryloxy group; X, Y and $Z_1$ each independently represents a saturated or unsaturated hydrocarbon group, an aromatic group, a hetero ring group, substituted amino group, an alkoxy group or an aryloxy group; substituents of $Z_1$ and $Z_2$ may bonds to each other to form a fused ring; n represents an integer of 1 to 3; and when n is 2 or greater, $Z_1$'s may be different from each other; with the proviso that a case where n is 1, X, Y and $R_2$ are methyl groups and $R_8$ is a hydrogen atom or a substituted boryl group and a case where n is 3 and $Z_1$ is a methyl group are excluded.)

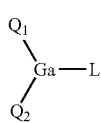
(F)

[In the formula, $Q^1$ and $Q^2$ each independently represents a ligand represented by the following general formula (G), L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ wherein $R^1$ represents a hydrogen atom, a substituted or unsubstituted alkyl group, a substituted or unsubstituted cycloalkyl group, a substituted or unsubstituted aryl group and a substituted or unsubstituted heterocyclic group; or a ligand represented by —O—Ga-$Q^3(Q^4)$ wherein $Q^3$ and $Q^4$ are the same as $Q^1$ and $Q^2$.]

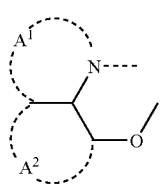
(G)

[In the formula, rings $A^1$ and $A^2$ each represents a fused six-membered aryl ring structure which may be substituted.]

The metal complex strongly characterizes n-type semiconductor and has a large capability of the electron injection. Since the generation energy for forming the metal complex is small, the bonding between the metal and the ligand is strong, to increase the fluorescence quantum efficiency of light emitting materials.

Specific examples of the substituents of rings $A^1$ and $A^2$ each forming the ligand in the general formula (G) include halogen atom such as chlorine atom, bromine atom, iodine atom and fluorine atom; substituted or unsubstituted alkyl group such as methyl group, ethyl group, propyl group, butyl group, s-butyl group, t-butyl group, pentyl group, hexyl group, heptyl group, octyl group, stearyl group, trichloromethyl group, etc.; substituted or unsubstituted aryl group such as phenyl group, naphthyl group, 3-methylphenyl group, 3-methoxyphenyl group, 3-fluorophenyl group, 3-trichloromethylphenyl group, 3-trifluoromethylphenyl group, 3-nitrophenyl group, etc.; substituted or unsubstituted alkoxy group such as methoxy group, n-butoxy group, t-butoxy group, trichloromethoxy group, trifluoroethoxy group, pentafluoropropoxy group, 2,2,3,3-tetrafluoropropoxy group, 1,1,1,3,3,3-hexafluoro-2-propoxy group, 6-(perfluoroethyl) hexyloxy group, etc.; substituted or unsubstituted aryloxy group such as phenoxy group, p-nitrophenoxy group, p-t-butylphenoxy group, 3-fluorophenoxy group, pentafluorophenyl group, 3-trifluoromethylphenoxy group, etc.; substituted or unsubstituted alkylthio group such as methylthio group, ethylthio group, t-butylthio group, hexylthio group, octylthio group, trifluoromethylthio group, etc.; substituted or unsubstituted arylthio group such as phenylthio group, p-nitrophenylthio group, p-t-butylphenylthio group, 3-fluorophenylthio group, pentafluorophenylthio group, 3-trifluoromethylphenylthio group, etc.; cyano group; nitro group; amino group; mono- or di-substituted amino groups such as methylamino group, diethylamino group, ethylamino group, diethylamino group, dipropylamino group, dibutyl amino group, diphenylamino group, etc.; acylamino groups such as bis(acetoxymethyl)amino group, bis(acetoxyethyl)amino group, bis(acetoxypropyl)amino group, bis(acetoxybutyl) amino group, etc.; hydroxy group; siloxy group; acyl group; carbamoyl group such as methylcarbamoyl group, dimethylcarbamoyl group, ethylcarbamoyl group, diethylcarbamoyl group, a propylcarbamoyl group, butyl carbamoyl group, a phenylcarbamoyl group, etc.; carboxylic acid group; sulfonic acid group; imido group; cycloalkyl group such as cyclopentyl group, cyclohexyl group, etc.; aryl group such as phenyl group, naphthyl group, biphenyl group, anthryl group, phenanthryl group, fluorenyl group, pyrenyl group, etc.; heterocyclic group such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triazinyl group, carbazolyl group, furanyl group, thiophenyl group, oxazolyl group, an oxadiazolyl group, a benzoxazolyl group, a thiazolyl group, a thiadiazolyl group, benzothiazolyl group, triazolyl group, imidazolyl group, benzimidazolyl group, pyranyl group, etc. The above substituents may bond each other to form a six-membered aryl ring or hetero ring.

A preferred embodiment of the organic EL device of the present invention contains a reductive dopant in an electron transporting region or an interfacial region between a cathode and an organic compound layer. The reductive dopant is defined as the substance capable of reducing an electron transporting compound. Accordingly, various compounds having a specified reducing property may be employable and examples of the reductive dopant include at least one compound selected from alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals, and organic complexes of rare earth metals.

Examples of the preferable reductive dopant include at least one alkali metal selected from a group consisting of Na (the work function: 2.36 eV), K (the work function: 2.28 eV), Rb (the work function: 2.16 eV) and Cs (the work function: 1.95 eV) or at least one alkaline earth metals selected from a group consisting of Ca (the work function: 2.9 eV), Sr (the work function: 2.0 to 2.5 eV) and Ba (the work function: 2.52 eV). whose work function of 2.9 eV or smaller is particularly preferable. Among those, more preferable reductive dopants include at least one kind or more alkali metal selected from the group consisting of K, Rb and Cs, the latter Rb or Cs being further more preferable and the last Cs being the most preferable. Since those alkali metals have a particularly high reducing capability, the luminance is improved and the lifetime is prolonged by the addition thereof into an electron injection region in a relatively small amount. A combination of two or more alkali metals is also preferably used as the reductive dopant having a work function of 2.9 eV or smaller. A combination containing Cs such as Cs and Na, Cs and K, Cs and Rb and Cs, Na and K is particularly preferred. By combinedly containing Cs, the reducing capability is effectively performed, and the luminance is enhanced and the lifetime is prolonged in the organic EL device by the addition into the electron injection region.

In the present invention, an electron injecting layer made of an electrically insulating material or a semiconductor may be further disposed between the cathode and the organic layer. The electron injecting layer enables to effectively prevent a leak of electric current and to improve the electron injection property. As the electrically insulating material, at least one metal compound selected from the group consisting of chalcogenides of alkali metals, chalcogenides of alkaline earth metals, halides of alkali metals and halides of alkaline earth metals is preferable. It is preferable that the electron injecting layer is constituted with the above metal compound since the electron injecting property can be further improved. Preferable examples of the alkali metal chalcogenide include $Li_2O$, $K_2O$, $Na_2S$, $Na_2Se$ and $NA_2O$. Preferable examples of the alkaline earth metal chalcogenide include CaO, BaO, SrO, BeO, BaS and CaSe. Preferable examples of the alkali metal halide include LiF, NaF, KF, LiCl, KCl and NaCl. Preferable examples of the alkaline earth metal halide include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides containing at least one element selected from Ba, Ca, Sr, Yb, Al, Ga, In, Li, Na, Cd, Mg, Si, Ta, Sb and Zn, which are used singly or in combination of two or more. It is preferable that the inorganic compound for constituting the electron transporting layer is in the form of a crystallite or amorphous insulating thin film. When the electron transporting layer is constituted with the above insulating thin film, a more uniform thin film can be formed and defective pixels such as dark spots can be decreased. Examples of the inorganic compound include chalcogenides of alkali metals, chalcogenides of alkaline earth metals, halides of alkali metals and halides of alkaline earth metals, which are described above.

(VII) Cathode

The cathode is formed from an electrode substance such as metal, alloy, electrically conductive compound or a mixture thereof each having a small work function (4 eV or smaller) to ensure the electron injection into the electron injecting or transporting layer or a light emitting layer. Examples of the electrode substance include sodium, sodium-potassium alloy, magnesium, lithium, magnesium-silver alloy, aluminum/aluminum oxide, -lithium alloy, indium, rare earth metal, etc.

The cathode is prepared by forming a thin film of the electrode material described above in accordance with a process such as the vapor deposition process and the sputtering process.

When the light emitted from the light emitting layer is taken out of the cathode, it is preferable that the cathode has a transmittance of greater than 10% to the emitted light.

It is also preferable that the sheet resistivity of the cathode is several hundreds $\Omega/\square$ or smaller and the thickness of the cathode is, in general, selected from 10 nm to 1 μm and preferably from 50 to 200 nm, (VIII) Insulating Layer In general, an organic EL device tends to form defects in pixels due to leak and short circuit since an electric field is applied to ultra-thin films. To prevent the defects, a layer of an insulating thin film may be inserted between the pair of electrodes.

Examples of the material employed for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be employed.

(IX) Fabrication Process of the Organic EL Device

The organic EL device of the present invention is fabricated, for example, by forming an anode, a light emitting layer, an optional hole injecting and transporting layer, an optional electron injecting and transporting layer, and a cathode in accordance with the process using the materials each being described above. Alternatively, each layer may be formed in a reverse order from the cathode to the anode.

An embodiment of the fabrication of an organic EL device having a construction of anode/hole injecting layer/light emitting layer/electron injecting layer/cathode in this order on a light-transmitting substrate will be described in the following.

First, on a suitable light-emitting substrate, a thin film of an anode substance is formed so as to have a film thickness of 1 μm or thinner, preferably from 10 nm to 200 nm in accordance with a vapor deposition process, a sputtering process, etc. Then, a hole injecting layer is formed on the anode. The hole injecting layer can be formed in accordance with the vacuum vapor deposition process, the spin coating process, the casting process or the LB process, as described above. The vacuum vapor deposition process is preferable because a uniform film can be easily obtained and pinhole is little formed. When the hole injecting layer is formed in accordance with the vacuum vapor deposition process, the conditions are preferably selected from the following ranges: temperature of deposition source: 50 to 450° C.; degree of vacuum: $10^{-7}$ to $10^{-3}$ Torr; vapor deposition rate: 0.01 to 50 nm/s; temperature of substrate: 50 to 300° C.; and film thickness: 5 nm to 5 μm; although depending on the employed compound (material for hole injecting layer), the crystal structure and the recombination structure.

Subsequently, the light emitting layer is formed on the hole injecting layer by depositing a thin film of the organic light emitting material in accordance with the vacuum vapor deposition process, the sputtering process, the spin coating process or the casting process. The vacuum vapor deposition process is preferable because a uniform film can be easily obtained and pinhole is little formed. When the light emitting layer is formed in accordance with the vacuum vapor deposition process, the conditions of the vacuum vapor deposition can be selected in the same ranges as in the deposition of the hole injecting layer, although depending on the compound to be used.

Next, the electron injecting layer is formed on the light emitting layer formed above. Similarly to the formation of the hole injecting layer and light emitting layer, the electron injecting layer is preferably formed in accordance with the vacuum vapor deposition process, because a uniform film is required. The conditions of the vacuum vapor deposition can be selected from the same ranges as in the formation of the hole injecting layer and light emitting layer.

Although the aromatic amine derivatives of the present invention depend on that they are contained in any layer among a light emitting region or a hole transporting region, it may be commonly vapor deposited together with other materials. In addition, when the spin coating process is employed, it may be contained therein by blending it with other materials.

Finally, the cathode is formed on the electron injecting layer, to obtain an organic EL device.

The cathode is made of a metal and can be formed in accordance with the vacuum vapor deposition process or the sputtering process. However, the vacuum vapor deposition process is preferably employed in order to prevent the underlying organic layers from being damaged during the formation of the film.

In the above fabrication of the organic EL device, the layers from the anode to the cathode are successively formed preferably in a single evacuation operation.

The process for forming the layers in the organic EL device of the present invention is not particularly limited. A conventional process such as the vacuum vapor deposition process and the spin coating process or so can be employed. The organic thin film layer containing the compound of the formula (1) included in the organic EL device of the present invention can be formed in accordance with the vacuum vapor deposition process, the molecular beam epitaxy process (the MBE process) or a known method of coating a solution of the compound such as the dipping process, the spin coating process, the casting process, the bar coating process and the roller coating process.

The thickness of each layer in the organic thin film layer in the organic EL device of the present invention is not particularly limited. In general, an excessively thin layer tends to have defects such as pinholes, and an excessively thick layer requires a high applied voltage and results in decreasing the efficiency. Therefore, the thickness is preferably from several nm to 1 μm.

The organic EL device emits light when a direct voltage of 5 to 40 V is applied with the anode being + terminal and the cathode being − terminal. In the reverse polarity, no electric current flows and no light is emitted upon the application of voltage. When an alternating voltage is applied, the uniform light emission is observed only in the polarity where the anode is + and the cathode is −. The wave shape of alternating voltage is not limited.

EXAMPLES

The present invention will be described in further detail with reference to Examples, which does not limit the scope of the present invention unless it goes beyond the gist of the invention.

Constitutional formulae of Intermediates 1 to 22 to be prepared in Syntheses 1 to 22 are as follows.

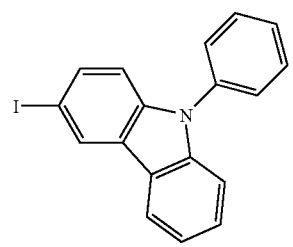

Intermediate 1

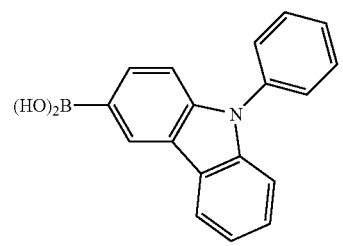

Intermediate 2

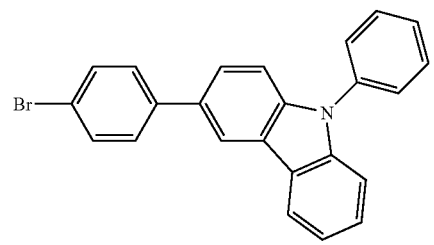

Intermediate 3

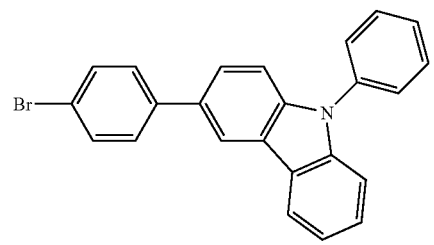

Intermediate 4

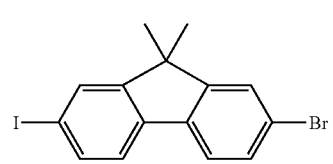

Intermediate 5

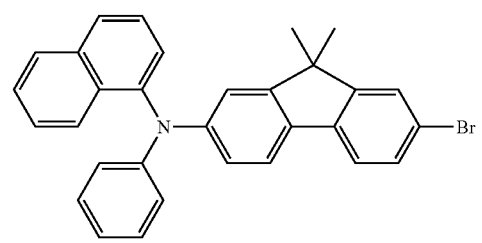

Intermediate 6

Intermediate 7
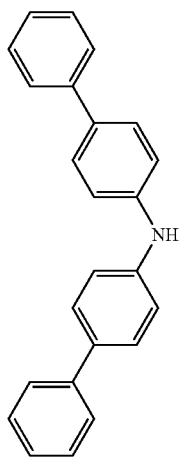
Intermediate 8
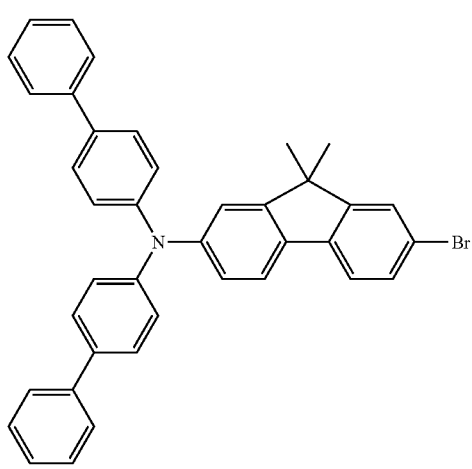
Intermediate 9
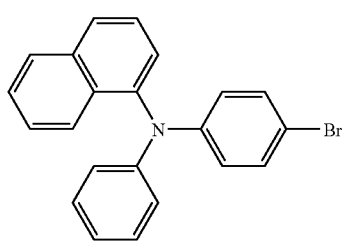
Intermediate 10
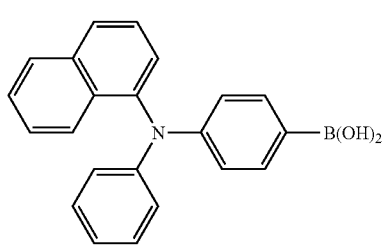
Intermediate 11
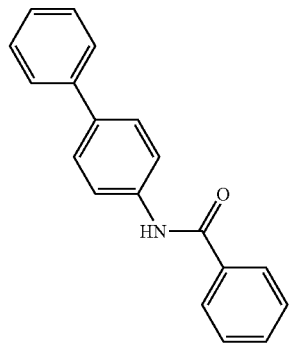
Intermediate 12
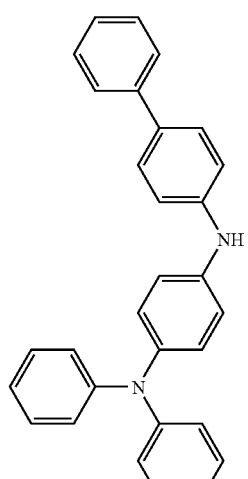
Intermediate 13
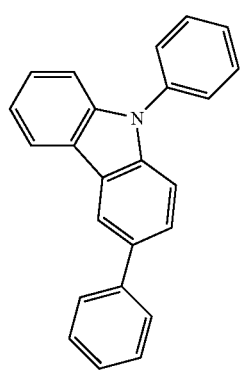
Intermediate 14
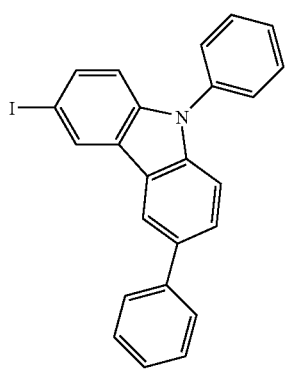

Intermediate 15

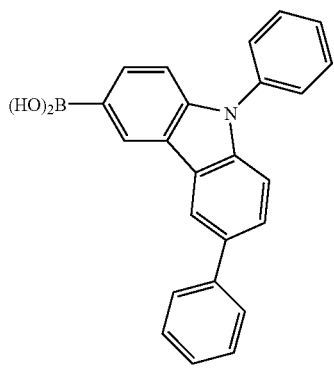

Intermediate 19

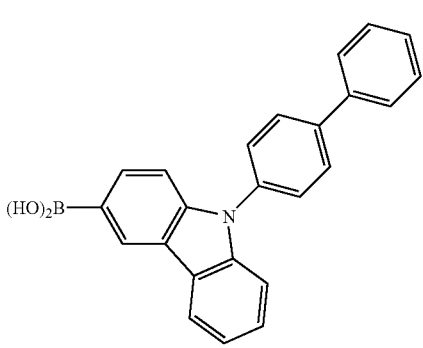

Intermediate 20

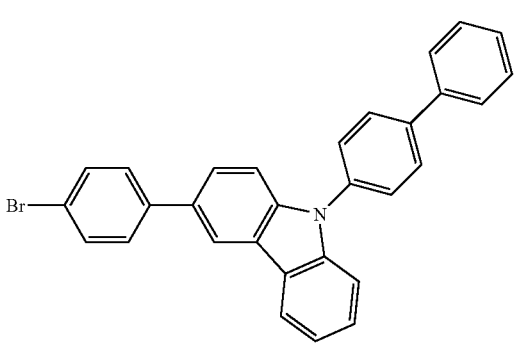

Intermediate 16

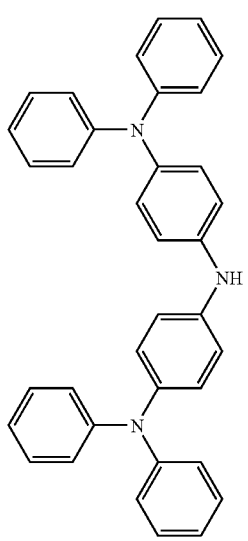

Intermediate 21

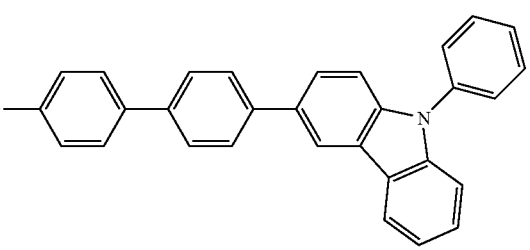

Intermediate 22

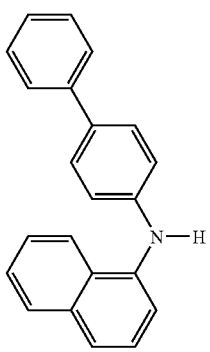

Intermediate 17

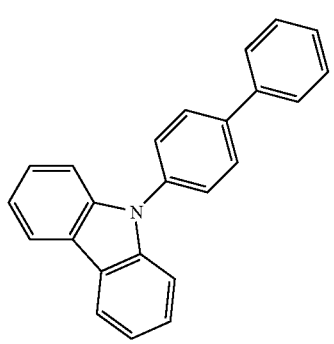

Intermediate 18

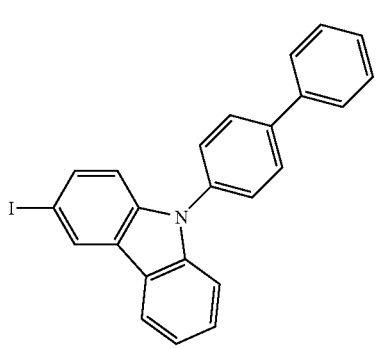

Synthesis 1 (Synthesis of Intermediate 1)

Blending 17.7 g of 9-phenyl carbazole, 6.03 g of potassium iodide, 7.78 g of potassium iodate, 5.90 ml of sulfuric acid and ethanol, the reaction was allowed to proceed at 75° C. for 2 h.

The resultant solution was cooled, and adding tap water and ethyl acetate, it was separated and extracted. Subsequently, an organic layer was washed with sodium bicarbonate water and tap water and then, it was condensed. Purifying the resultant crude product by means of a silicagel chromatography (toluene), vacuum dried the resultant solid to obtain 21.8 g of white solid, which was analyzed by FD-MS (Field Desorption Mass Spectrum) and identified as Intermediate 1.

Synthesis 2 (Synthesis of Intermediate 2)

Under an atmospheric argon gas flow, dehydrated toluene and dehydrated ether were added to 13.1 g of Intermediate 1, and the resultant solution was cooled down to −45° C. Dripping 25 ml of n-butyllithium hexane solution (1.58 M), elevated the temperature up to −5° C. while stirring for 1 h. Cooling down to −45° C. again, after slowly dripping 25 ml of boronic acid triisopropyl ester, the reaction was allowed to proceed for 2 h.

Returning to a room temperature, a 10% dilute hydrochloric acid solution was added and stirred, and an organic layer was extracted. After washing with a saturated sodium chloride solution, it was dried over unhydrated sulfur trioxide magnesium, separated by filtration and condensed. Purifying the resultant solid by means of a silicagel chromatography (toluene), the solid was washed with n-hexane and vacuum dried to obtain 7.10 g of solid, which was analyzed by FD-MS and identified as Intermediate 2.

Synthesis 3 (Synthesis of Intermediate 3)

Blending 21.8 g of Intermediate 1, 11.8 g of 4-bromophenyl boronic acid, 1.38 g of Pd(PPh$_3$)$_4$, 21.9 g of sodium carbonate, tap water and dimethoxyethane, the reaction was allowed to proceed under refluxing for 8 h.

The resultant solution was cooled down and the reacted solution was filtered, and a water layer prepared by separating the filtered residue through acetone was extracted with dichloromethane. The collected filtrate was separated and adding acetone and dichloromethane, the resultant solution was further separated. A water layer prepared by separating the filtered residue through acetone was extracted with dichloromethane, and a collected organic layer was washed with water and condensed. Purifying the resultant crude product by means of a silicagel chromatography (hexane:dichloromethane=9:1), re-crystallized the resultant solid through toluene and methanol, vacuum dried to obtain 4.18 g of white solid, which was analyzed by FD-MS and identified as Intermediate 3.

Synthesis 4 (Synthesis of Intermediate 4)

Under an atmospheric argon gas flow, dissolving 12.5 g of 2-bromofluorene into 50 ml of acetic acid, 0.9 ml of sulfuric acid was dripped and stirred at a room temperature for 10 min. Subsequently, 6.5 g of iodine and 2.33 g of periodic acid were added and the reaction was allowed to proceed at 80° C. for 6 h.

The resultant solution was cooled down, extracted through toluene and tap water. Subsequently, a toluene layer was washed with sodium bicarbonate water, saturated sodium chloride solution and tap water, and then dried over sodium sulfate. After the sodium sulfate was separated by filtration, purifying the resultant solid by means of a silicagel chromatography (toluene), the solid was washed with n-hexane and vacuum dried to obtain 9.00 g of solid, which was analyzed by FD-MS and identified as Intermediate 4.

Synthesis 5 (Synthesis of Intermediate 5)

Under an atmospheric argon gas flow, 9.00 g of Intermediate 4 and 0.35 g of benzyltriethylammonium chloride were placed into 25 ml of DMSO (dimethylsulfoxide) and 8 ml of 50 wt % NaOH aqueous solution and stirred at a room temperature for 10 min, and dripping 2.6 ml of methyl iodide, the reaction was allowed to proceed at a room temperature for 3 h.

The resultant solution was extracted through toluene and tap water, washed with saturated sodium chloride solution and tap water, and condensed. Purifying by means of silicagel chromatography (n-hexane), vacuum dried to obtain 8.50 g of solid, which was analyzed by FD-MS and identified as Intermediate 5.

Synthesis 6 (Synthesis of Intermediate 6)

Under an atmospheric argon gas flow, placing 20.0 g of Intermediate 5, 11.5 g of N-phenyl-1-naphthylamine, 447 mg of copper iodide, 0.532 ml of N,N'-dimethylethylenediamine, 7.22 g of t-butoxy sodium and dehydrated xylene, the reaction was allowed to proceed at 130° C. for 8 h.

The resultant solution was cooled down and after extracting the reacted solution through 100 ml of toluene it was filtered through sellite, and was condensed. Purifying the resultant crude product by means of a silicagel chromatography (hexane:toluene=9:1), the resultant pale yellow solid was washed with methanol, vacuum dried to obtain 16.0 g of white solid, which was analyzed by FD-MS and identified as Intermediate 6.

Synthesis 7 (Synthesis of Intermediate 7)

Under an atmospheric argon gas flow, blending 17.0 g of benzamide, 68.8 g of 4-bromobiphenyl, 2.70 g of copper iodide, 40.8 g of potassium carbonate and diethylbenzene, the reaction was allowed to proceed at 175° C. for 19 h.

The resultant solution was cooled down and adding tap water, the residue was washed with acetone, methanol and tap water 3 times to obtain 55.0 g of benzamide compound of Intermediate 7.

Blending 55.0 g of benzamide compound of Intermediate 7, 26.3 g of potassium hydroxide, 25 ml of tap water and diethylbenzene, the reaction was allowed to proceed at 175° C. for 5.5 h.

The resultant solution was cooled down and after adding tap water, it was filtered, washed with acetone, methanol and tap water 3 times. Purifying the resultant mixture by means of a short column (toluene), the resultant solid was washed with n-hexane and vacuum dried to obtain 25.0 g of white solid, which was analyzed by FD-MS and identified as Intermediate 7.

Synthesis 8 (Synthesis of Intermediate 8)

Intermediate 8 was synthesized in the same manner as Intermediate 6 except that Intermediate 7 was employed instead of N-phenyl-1-naphthylamine. The resultant solid was analyzed by FD-MS and identified as Intermediate 8.

Synthesis 9 (Synthesis of Intermediate 9)

Intermediate 9 was synthesized in the same manner as Intermediate 6 except that 1-bromo-4-iodobenzene was employed instead of Intermediate 5. The resultant solid was analyzed by FD-MS and identified as Intermediate 9.

Synthesis 10 (Synthesis of Intermediate 10)

Intermediate 10 was synthesized in the same manner as Intermediate 2 except that Intermediate 9 was employed instead of Intermediate 1. The resultant solid was analyzed by FD-MS and identified as Intermediate 10.

Synthesis 11 (Synthesis of Intermediate 11)

Under an atmospheric argon gas flow, blending 5.70 g of benzamide, 11.5 g of 4-bromobiphenyl, 450 mg of copper iodide, 6.80 g of potassium carbonate and diethylbenzene, the reaction was allowed to proceed at 175° C. for 10 h.

The resultant solution was cooled down and after adding tap water, it was filtered and the residue was washed with acetone, methanol and tap water 3 times to obtain 11.8 g of Intermediate 11.

Synthesis 12 (Synthesis of Intermediate 12)

Under an atmospheric argon gas flow, blending 11.8 g of Intermediate 11, 16.8 g of 4-bromotriphenylamine, 414 mg of copper iodide, 6.2 g of potassium carbonate and diethylbenzene, the reaction was allowed to proceed at 175° C. for 15 h.

The resultant solution was cooled down and adding tap water, the residue was washed with acetone, methanol and tap water 3 times to obtain 20.4 g of benzamide compound of Intermediate 12.

Blending 20.4 g of benzamide compound of Intermediate 12, 7.89 g of potassium hydroxide, 7.5 ml of tap water and diethylbenzene, the reaction was allowed to proceed at 175° C. for 5.5 h.

The resultant solution was cooled down and after adding tap water, it was filtered, washed with acetone, methanol and tap water 3 times. Purifying the resultant mixture by means of a short column (toluene), the resultant solid was washed with n-hexane and vacuum dried to obtain 9.65 g of yellowish white solid, which was analyzed by FD-MS and identified as Intermediate 12.

Synthesis 13 (Synthesis of Intermediate 13)

Intermediate 13 was synthesized in the same manner as Intermediate 3 except that phenyl boronic acid was employed instead of 4-bromophenyl boronic acids. The resultant solid was analyzed by FD-MS and identified as Intermediate 13.

Synthesis 14 (Synthesis of Intermediate 14)

Intermediate 14 was synthesized in the same manner as Intermediate 1 except that Intermediate 13 was employed instead of 9-phenyl carbazole. The resultant solid was analyzed by FD-MS and identified as Intermediate 14.

Synthesis 15 (Synthesis of Intermediate 15)

Intermediate 15 was synthesized in the same manner as Intermediate 2 except that Intermediate 14 was employed instead of Intermediate 1. The resultant solid was analyzed by FD-MS and identified as Intermediate 15.

Synthesis 16 (Synthesis of Intermediate 16)

Intermediate 16 was synthesized in the same manner as Intermediate 7 except that 4-bromotriphenylamine was employed instead of 4-bromobiphenyl. The resultant solid was analyzed by FD-MS and identified as Intermediate 16.

Synthesis 17 (Synthesis of Intermediate 17)

Under an atmospheric argon gas flow, blending 3.3 g of carbazole, 5.1 g of 4-bromo biphenyl, 231 mg of $Pd_2(dba)_3$, 325 mg of $P(t-Bu)_3$, 2.9 g of t-butoxysodium and toluene, the reaction was allowed to proceed at 80° C. for 4 h.

The resultant solution was cooled down and after adding toluene; it was filtered through sellite and was condensed. Purifying the resultant mixture by means of a silicagel chromatography (hexane:dichloromethane=6:1), the resultant solid was washed with n-hexane, vacuum dried to obtain 4.1 g of white solid, which was analyzed by FD-MS and identified as Intermediate 17.

Synthesis 18 (Synthesis of Intermediate 18)

Intermediate 18 was synthesized in the same manner as Intermediate 1 except that Intermediate 17 was employed instead of 9-phenylcarbazole. The resultant solid was analyzed by FD-MS and identified as Intermediate 18.

Synthesis 19 (Synthesis of Intermediate 19)

Intermediate 19 was synthesized in the same manner as Intermediate 2 except that Intermediate 18 was employed instead of Intermediate 1. The resultant solid was analyzed by FD-MS and identified as Intermediate 19.

Synthesis 20 (Synthesis of Intermediate 20)

Intermediate 20 was synthesized in the same manner as Intermediate 3 except that Intermediate 18 was employed instead of Intermediate 1. The resultant solid was analyzed by FD-MS and identified as Intermediate 20.

Synthesis 21 (Synthesis of Intermediate 21)

Intermediate 21 was synthesized in the same manner as Intermediate 3 except that 4-bromo-4'-iodobiphenyl was employed instead of Intermediate 1 and that Intermediate 19 was employed instead of 4-bromophenyl boronic acids. The resultant solid was analyzed by FD-MS and identified as Intermediate 21.

Synthesis 22 (Synthesis of Intermediate 22)

Intermediate 22 was synthesized in the same manner as Intermediate 12 except that 1-bromonaphthalene was employed instead of 4-bromotriphenylamine. The resultant solid was analyzed by FD-MS and identified as Intermediate 22.

Synthesis Example 1 (Synthesis of Compound H1)

Under an atmospheric argon gas flow, 6.0 g of Intermediate 2, 8.6 g of Intermediate 6, 404 mg of $Pd(PPh_3)_4$ was placed into 26 ml of 2M sodium carbonate aqueous solution and toluene, the reaction was allowed to proceed under refluxing for 4 h.

The resultant solution was cooled down and was filtered through sellite, and the filtrate was separated. An organic layer was washed with tap water, purifying by means of a silicagel chromatography (toluene), re-precipitated (hexane, dichloromethane) the resultant solid three times. Washing the solid with n-hexane, vacuum dried to obtain 6.93 g of yellowish white solid, which was analyzed by FD-MS and identified as Compound H1.

Synthesis Example 2 (Synthesis of Compound H2)

Compound H2 was synthesized in the same manner as Synthesis of Compound H1 in Synthesis Example 1 except that Intermediate 8 was employed instead of Intermediate 6. The resultant solid was analyzed by FD-MS and identified as Compound H2.

Synthesis Example 3 (Synthesis of Compound H3)

Compound H3 was synthesized in the same manner as Synthesis of Compound H1 in Synthesis Example 1 except that Intermediate 10 was employed instead of Intermediate 2 and that Intermediate 3 was employed instead of Intermediate 6. The resultant solid was analyzed by FD-MS and identified as Compound H3.

Synthesis Example 4 (Synthesis of Compound H4)

Under an atmospheric argon gas flow, blending 4.8 g of N-phenyl-1-naphthylamine, 8.0 g of Intermediate 3, 231 mg of $Pd_2(dba)_3$, 325 mg of $P(t-Bu)_3$, 2.9 g of tertialbutoxysodium and toluene, the reaction was allowed to proceed at 80° C. for 4 h.

The resultant solution was cooled down and after adding toluene, it was filtered through sellite and was condensed. Purifying the resultant mixture by means of a silicagel chromatography (hexane:dichloromethane=6:1), the resultant solid was washed with n-hexane, vacuum dried to obtain 8.96 g of yellowish white solid, which was analyzed by FD-MS and identified as Compound H4.

Synthesis Example 5 (Synthesis of Compound H5)

Compound H5 was synthesized in the same manner as Synthesis of Compound H4 in Synthesis Example 4 except that Intermediate 7 was employed instead of N-phenyl-1-naphthylamine. The resultant solid was analyzed by FD-MS and identified as Compound H5.

Synthesis Example 6 (Synthesis of Compound H6)

Compound H6 was synthesized in the same manner as Synthesis of Compound H4 in Synthesis Example 4 except that Intermediate 12 was employed instead of N-phenyl-1-naphthylamine. The resultant solid was analyzed by FD-MS and identified as Compound H6.

Synthesis Example 7 (Synthesis of Compound H7)

Compound H7 was synthesized in the same manner as Synthesis of Compound H1 in Synthesis Example 1 except that Intermediate 15 was employed instead of Intermediate 2. The resultant solid was analyzed by FD-MS and identified as Compound H7.

Synthesis Example 8 (Synthesis of Compound H8)

Compound H8 was synthesized in the same manner as Synthesis of Compound H4 in Synthesis Example 4 except that Intermediate 16 was employed instead of N-phenyl-1-naphthylamine. The resultant solid was analyzed by FD-MS and identified as Compound H8.

Synthesis Example 9 (Synthesis of Compound H53)

Compound H53 was synthesized in the same manner as Synthesis of Compound H4 in Synthesis Example 4 except that Intermediate 7 was employed instead of N-phenyl-1-naphthylamine and that Intermediate 20 was employed instead of Intermediate 3. The resultant solid was analyzed by FD-MS and identified as Compound H53.

Synthesis Example 10 (Synthesis of Compound H55)

Compound H55 was synthesized in the same manner as Synthesis of Compound H4 in Synthesis Example 4 except that Intermediate 22 was employed instead of N-phenyl-1-naphthylamine. The resultant solid was analyzed by FD-MS and identified as Compound H55.

Synthesis Example 11 (Synthesis of Compound H57)

Compound H57 was synthesized in the same manner as Synthesis of Compound H4 in Synthesis Example 4 except that aniline was employed instead of N-phenyl-1-naphthylamine. The resultant solid was analyzed by FD-MS and identified as Compound H57.

Synthesis Example 12 (Synthesis of Compound H60)

Compound H60 was synthesized in the same manner as Synthesis of Compound H4 in Synthesis Example 4 except that Intermediate 7 was employed instead of N-phenyl-1-naphthylamine and that Intermediate 21 was employed instead of Intermediate 3. The resultant solid was analyzed by FD-MS and identified as Compound H60.

Example 1

A glass substrate (manufactured by GEOMATEC Company) of 25 mm×75 mm×1.1 mm thickness having an ITO transparent electrode was cleaned by application of ultrasonic wave in isopropyl alcohol for 5 min and then by exposure to ozone generated by ultraviolet light for 30 min. The cleaned glass substrate having the transparent electrode lines was attached to a substrate holder of a vacuum vapor deposition apparatus. On the surface of the cleaned substrate at the side having the transparent electrode, a film of Compound H232 below having a thickness of 60 nm was formed so as to cover the transparent electrode. The formed film of H232 worked as the hole injecting layer. A layer of the Compound H1 as a hole transporting material having a thickness of 20 nm was formed over the film of H232. The formed film worked as the hole transporting layer. Further, Compound EM1 below was vapor deposited thereby forming a film having a thickness of 40 nm. At the same time, the following amine compound D1 having styryl group below as a light emitting molecule was deposited with a weight ratio of EM1:D1=40:2. The formed film worked as a light emitting layer. On the film formed above, a film of Alq having a thickness 10 nm was formed. The formed film worked as an electron injecting layer. Thereafter, Li (the source of lithium: manufactured by SAES GETTERS Company) as a reductive dopant and Alq were binary vapor deposited and an Alq:Li film (film thickness: 10 nm) was formed as the electron injecting layer (or the cathode). On the Alq:Li film, aluminum was vapor deposited to form a metal cathode and an organic EL device was fabricated.

About the resultant organic EL device, luminescent color was observed and current efficiency of light emission was measured at initial luminance of 5000 $cd/m^2$ under a room temperature and DC constant current driving. The results are shown in Table 1.

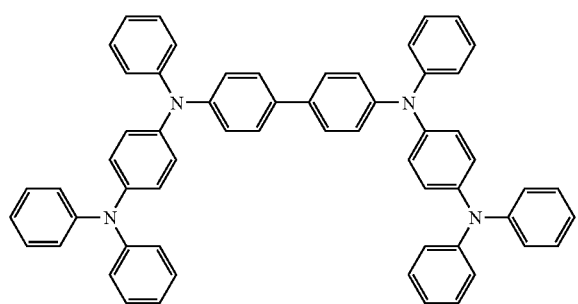

H232

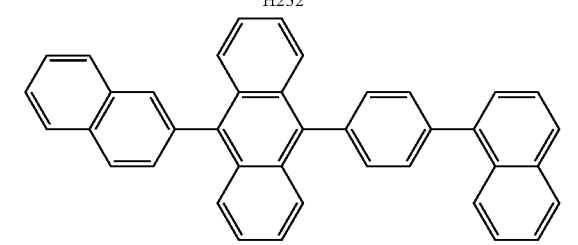

EM1

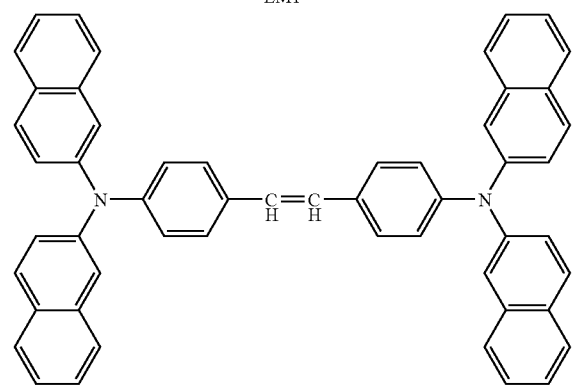

D1

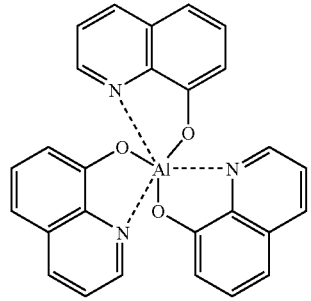

Alq

Examples 2 to 12

Organic EL devices were fabricated in similar procedures as Example 1 except that compounds described in Table 1 were employed as the hole transporting material instead of Compound H1.

About the resultant organic EL devices, luminescent colors were observed and current efficiencies of light emission were measured at initial luminance of 5000 cd/m² under a room temperature and DC constant current driving. The results are shown in Table 1.

Comparative Examples 1 to 5

Organic EL devices were fabricated in similar procedures as Example 1 except that Comparative Compounds 1 to 5 below and described in Table 1 were employed as the hole transporting material instead of Compound H1.

About the resultant organic EL device, luminescent colors were observed and current efficiencies of light emission were measured at initial luminance of 5000 cd/m² under a room temperature and DC constant current driving. The results are shown in Table 1.

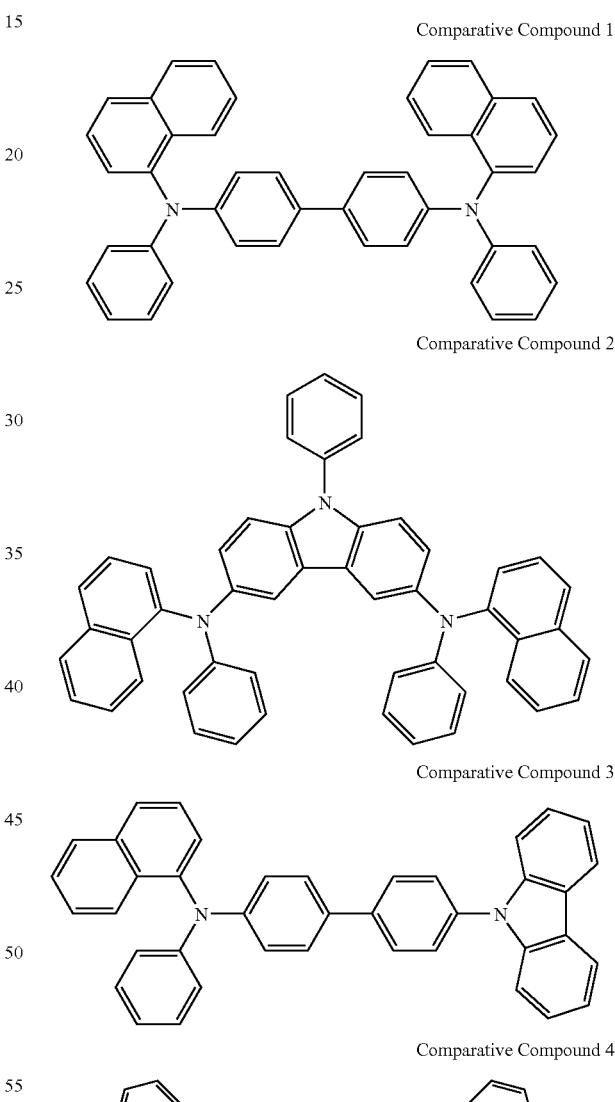

Comparative Compound 1

Comparative Compound 2

Comparative Compound 3

Comparative Compound 4

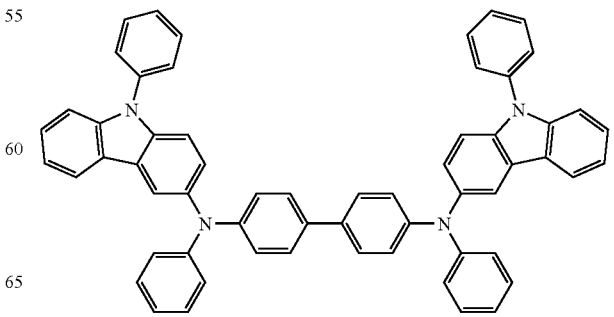

Comparative Compound 5

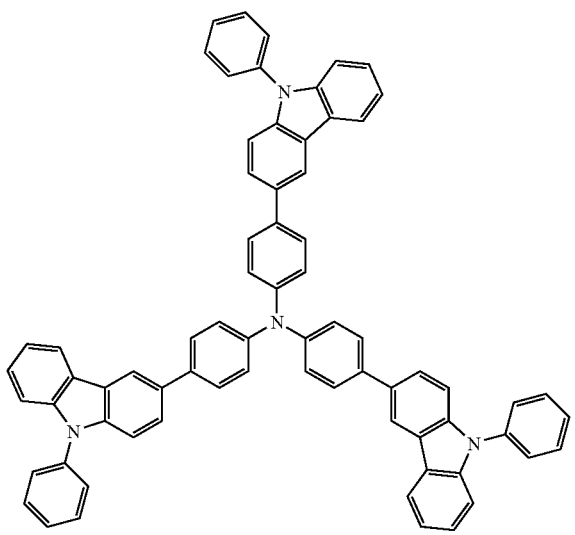

Example 13

An organic EL device was fabricated in a similar procedure as Example 1 except that arylamine compound D2 below was employed instead of the amine compound D1 having styryl groups. Me represents a methyl group.

About the resultant organic EL device, luminescent color was observed and current efficiency of light emission was measured at initial luminance of 5000 cd/m² under a room temperature and DC constant current driving. The results are shown in Table 1.

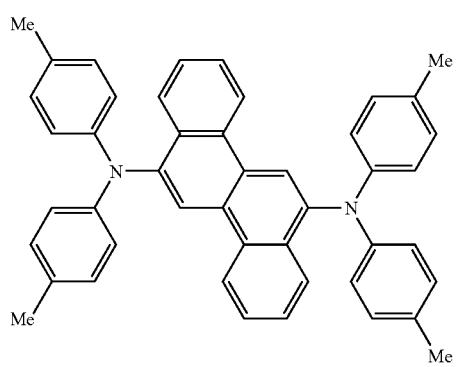

D2

Comparative Example 6

Organic EL device was fabricated in a similar procedure as Example 12 except that the above Comparative Compound 1 was employed as the hole transporting material instead of Compound H1.

About the resultant organic EL device, luminescent color was observed and current efficiency of light emission was measured at initial luminance of 5000 cd/m² under a room temperature and DC constant current driving. The results are shown in Table 1.

TABLE 1

|  | Comparative Compounds | Emission efficiency (cd/A) | Luminescent color |
|---|---|---|---|
| Examples |  |  |  |
| 1 | H1 | 6.8 | Blue |
| 2 | H2 | 6.9 | Blue |
| 3 | H3 | 6.4 | Blue |
| 4 | H4 | 5.9 | Blue |
| 5 | H5 | 6.1 | Blue |
| 6 | H6 | 6.0 | Blue |
| 7 | H7 | 7.1 | Blue |
| 8 | H8 | 5.9 | Blue |
| 9 | H53 | 6.7 | Blue |
| 10 | H55 | 6.5 | Blue |
| 11 | H57 | 6.3 | Blue |
| 12 | H60 | 6.8 | Blue |
| 13 | H1 | 6.1 | Blue |
| Comparative Examples |  |  |  |
| 1 | 1 | 5.1 | Blue |
| 2 | 2 | 4.0 | Blue |
| 3 | 3 | 4.3 | Blue |
| 4 | 4 | 4.8 | Blue |
| 5 | 5 | 3.9 | Blue |
| 6 | 1 | 5.2 | Blue |

As apparently evaluated from Table 1, the organic EL devices of Examples 1 to 12 have enhanced efficiencies of light emission over publicly known Comparative Compound 1 as a hole transporting material, Comparative Compound 2 wherein N bonds directly to 3- and 6-position of carbazole, Comparative Compound 3 wherein N bonds to N of carbazole via bonding group and which has no substituent in its carbazole skeleton, and Comparative Compound 4 that is a compound with a type wherein N directlybonds to 3-position of carbazole. As the reason, it is conceivable that 3- and 9-position of carbazole skeleton in the aromatic amine derivative of the present invention are protected and there is a bonding group between carbazole skeletons and N.

Example 14

An organic EL device was fabricated in a similar procedure as Example 1 except that Compound H53 was employed instead of H232 and that an arylamine compound TBDB below instead of Compound H1.

About the resultant organic EL device, luminescent color was observed and recognized as blue. Further, driving voltage was measured at initial luminance of 5000 cd/m² under a room temperature and DC constant current driving and as a result, it was 6.5 V.

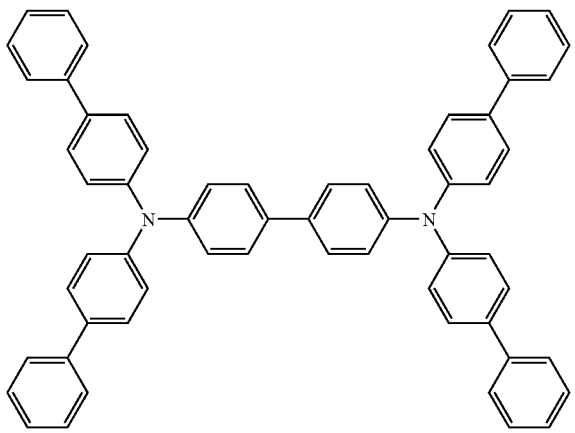

TBDB

Example 15

An organic EL device was fabricated in accordance with the same procedure as Example 14 except that Compound H60 was employed instead of H53.

About the resultant organic EL device, luminescent color was observed and recognized as blue. Further, driving voltage was measured at initial luminance of 5000 cd/m² under a room temperature and DC constant current driving and as a result, it was 6.6 V.

Comparative Example 7

An organic EL device was fabricated in accordance with the same procedure as Example 14 except that H232 was employed instead of H53.

About the resultant organic EL device, luminescent color was observed and recognized as blue. Further, driving voltage was measured at initial luminance of 5000 cd/m² under a room temperature and DC constant current driving and as a result, it was 7.2 V.

Comparative Example 8

An organic EL device was fabricated in accordance with the same procedure as Example 14 except that Comparative Compound 4 was employed instead of H53.

About the resultant organic EL device, luminescent color was observed and recognized as blue. Further, driving voltage was measured at initial luminance of 5000 cd/m² under a room temperature and DC constant current driving and as a result, it was 7.3 V.

As described above, the employment of the aromatic amine of the present invention for a hole injecting layer was proved to be effective in reducing the driving voltage.

Industrial Applicability

As described in detail above, the organic EL device employing the aromatic amine derivative of the present invention as materials for the organic EL device, particularly as a hole transporting material or a hole injecting material has an enhanced efficiency of light emission and is highly practical.

Therefore, the organic EL device of the present invention is useful for a planar light emitting member for wall televisions and a light source for a backlight of displays.

What is claimed is:

1. An aromatic amine derivative represented by the following general formula (1)

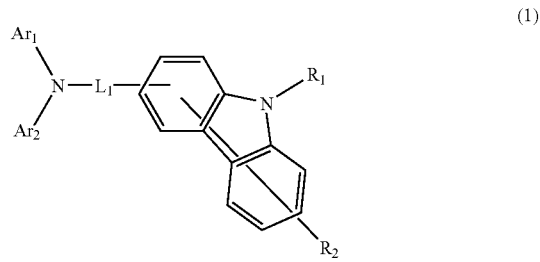

(1)

wherein $L_1$ represents a substituted or unsubstituted arylene group having 6 to 60 carbon atoms forming the aromatic ring, or a substituted or unsubstituted heteroarylene group having 5 to 60 atoms forming a ring; $Ar_1$ and $Ar_2$ each independently represents a 1-naphthyl group, a 2-naphthyl group, a 2-biphenyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group or a m-terphenyl-2-yl group; $R_1$ represents an unsubstituted aryl group having 6 to 60 carbon atoms forming the aromatic ring; $R_2$ represents a hydrogen atom, an unsubstituted aryl group having 6 to 60 carbon atoms forming the aromatic ring, a substituted or unsubstituted alkyl group having 1 to 50 carbon atoms, a substituted or unsubstituted alkoxy group having 1 to 50 carbon atoms, a substituted or unsubstituted aryloxy group having 6 to 50 atoms forming a ring, a substituted or unsubstituted arylthio group having 5 to 50 atoms forming a ring, a substituted or unsubstituted alkoxycarbonyl group having 2 to 50 carbon atoms, a halogen atom, a cyano group, a nitro group, a hydroxyl group or a carboxyl group; with the proviso that $L_1$, $Ar_1$, $Ar_2$ and $R_2$ do not contain a fluorene structure, and that the number of a carbazole structure in the aromatic amine derivative represented by the general formula (1) is 1.

2. The aromatic amine derivative according to claim 1, wherein $L_1$ represents an unsubstituted arylene group having 6 to 60 carbon atoms forming the aromatic ring, or an unsubstituted heteroarylene group having 5 to 60 atoms forming a ring; $R_1$ represents an unsubstituted aryl group having 6 to 60 carbon atoms forming the aromatic ring; $R_2$ represents a hydrogen atom, an unsubstituted aryl group having 6 to 60 carbon atoms forming the aromatic ring or an unsubstituted alkyl group having 1 to 50 carbon atoms.

3. The aromatic amine derivative according to claim 1, wherein $R_1$ is a substituted or unsubstituted phenyl group, a biphenylyl group, a terphenylyl group, an α-naphthyl group, a β-naphthyl group or a phenanthryl group.

4. The aromatic amine derivative according to claim 1, wherein $R_2$ is a substituted or unsubstituted aryl group bonding to 3- or 6-position of its carbazole skeleton.

5. The aromatic amine derivative according to claim 1, wherein $L_1$ is a substituted or unsubstituted phenylene group, a biphenylene group, a terphenylene group, a naphthylene group, or a phenanthrylene group.

6. The aromatic amine derivative according to claim 1, wherein a number of the ring carbon atoms forming rings contained in the aromatic amine derivative are 48 to 70.

7. An organic electroluminescent device comprising the aromatic amine derivative according to claim 1.

8. An organic electroluminescent device comprising as a hole transporting material or a hole injecting material, the aromatic amine derivative according to claim 1.

9. An organic electroluminescence device which comprises one or more organic thin film layers including at least one light emitting layer sandwiched between a cathode and an anode, wherein at least one of the organic thin film layers comprises the aromatic amine derivative according to claim 1 singly or as a mixture component.

10. The organic electroluminescence device according to claim 9, wherein the organic thin film layers include a hole transporting layer, and the hole transporting layer comprises the aromatic amine derivative.

11. The organic electroluminescence device according to claim 9, wherein the organic thin film layers include a hole injecting layer, and the hole injecting layer comprises the aromatic amine derivative.

12. The organic electroluminescence device according to claim 9, wherein the organic thin film layers comprise at least one of a hole transporting layer and a hole injecting layer, and wherein the aromatic amine derivative is contained as a component in the hole transporting layer or the hole injecting layer.

13. The organic electroluminescence device according to claim 9, wherein the light emitting layer comprises at least one of styrylamine and arylamine.

14. The organic electroluminescence device according to claim 9, which emits blue light.

15. The aromatic amine derivative according to claim 1, wherein $L_1$ is a phenylene group, a biphenylene group, a terphenylene group, a phenanthrylene group, a furyl group-substituted phenylene group, a dibenzofuranyl group-substituted phenylene group, or a dibenzofuranyl group;

$R_1$ is a phenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, or a m-terphenyl-2-yl group; and $R_2$ is a hydrogen aton, a phenyl group, a 1-naphthyl group, a 2-naphthyl group, a 2-biphenylyl group, a 3-biphenylyl group, a 4-biphenylyl group, a p-terphenyl-4-yl group, a p-terphenyl-3-yl group, a p-terphenyl-2-yl group or a m-terphenyl-2-yl group.

16. The organic amine derivative according to claim 1, wherein $Ar_1$ and $Ar_2$ are each independently a 1-naphthyl group, 2-naphthyl group, 2-biphenyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group, or m-terphenyl-2-yl group;

$L_1$ is at least one of a phenylene group and a biphenylene;

$R_1$ is at least one selected from the group consisting of a phenyl group, a 2-biphenylyl group and a 3-biphenylyl group;

$R_2$ is at least one of a hydrogen atom and a phenyl group.

17. The aromatic amine derivative according to claim 15, wherein $Ar_1$ and $Ar_2$ are each independently selected from the group consisting of a 2-biphenyl group and a 3-biphenyl group.

18. An organic electroluminescence device comprising one or more organic thin film layers containing the aromatic amine group of claim 1, wherein $Ar_1$ and $Ar_2$ are each independently a 2-biphenyl group and a 3-biphenyl group;

$L_1$ is at least one of a phenylene group and a biphenylene;
$R_1$ is at least one selected from the group consisting of a phenyl group, a 2-biphenylyl group and a 3-biphenylyl group;
$R_2$ is at least one of a hydrogen atom and a phenyl group; and the aromatic amine derivative is a hole transporting material.

19. An organic electroluminescence device comprising one or more organic thin film layers between a cathode and an anode,
wherein at least one organic thin film layer comprises, as a hole transport material, an aromatic amine derivative selected from the group consisting of:

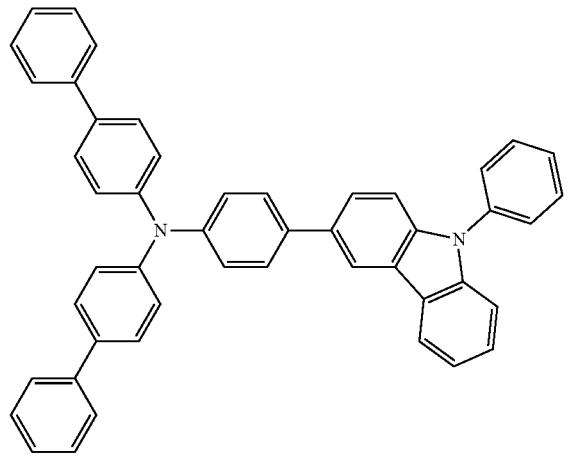

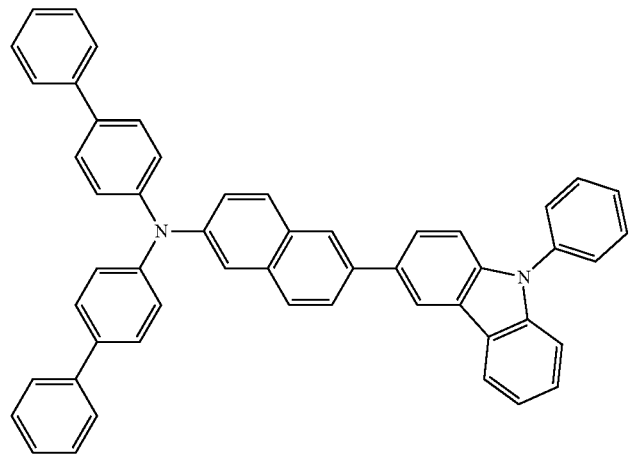
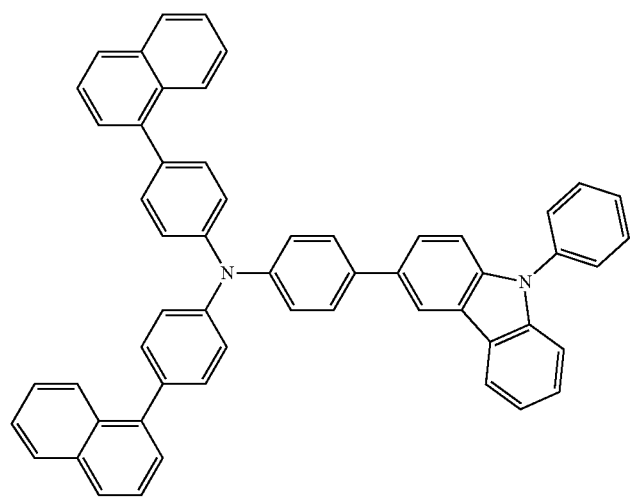
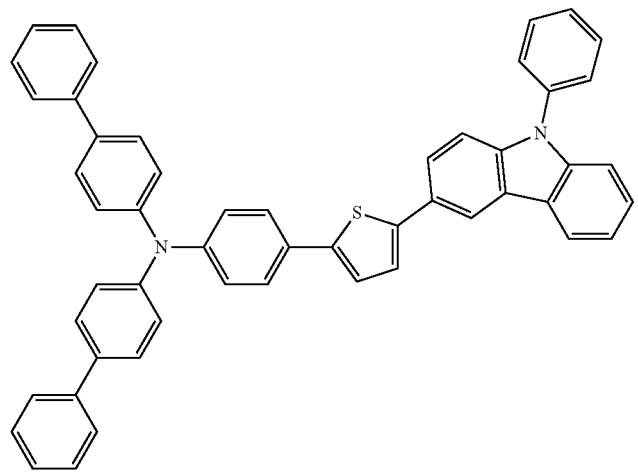

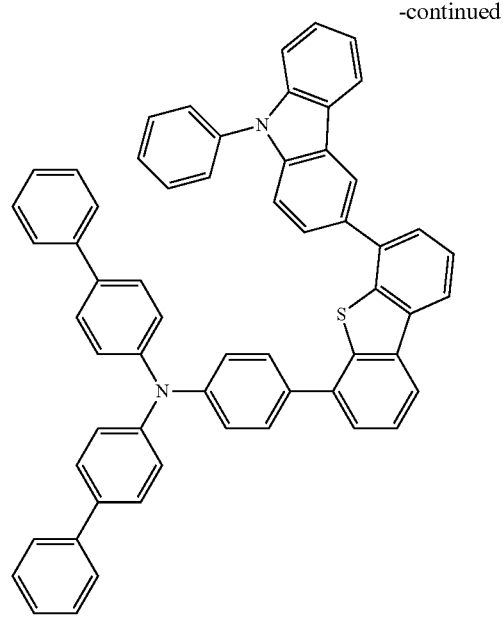
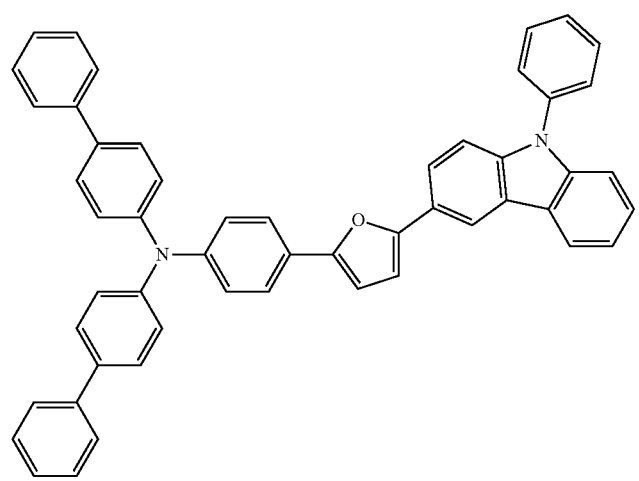
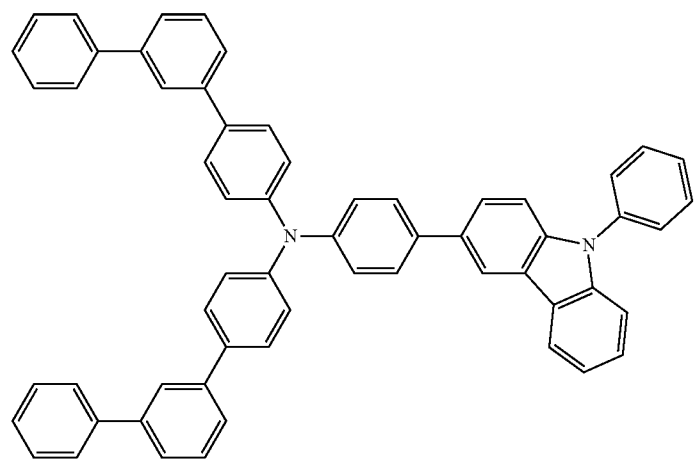

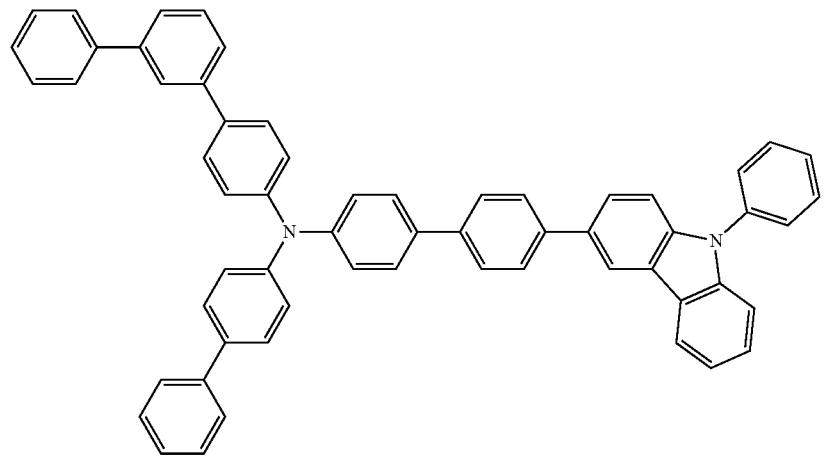
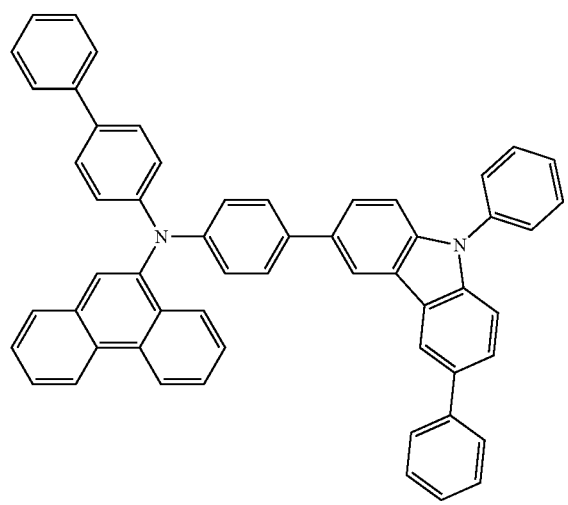
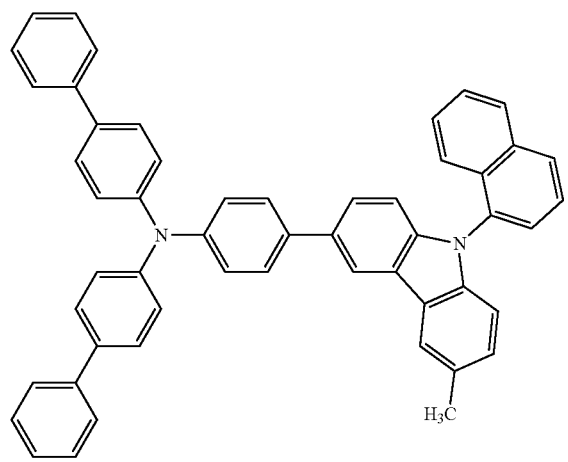

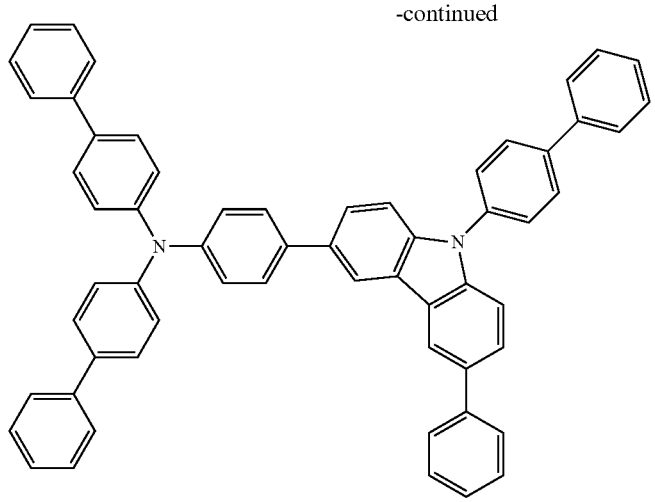
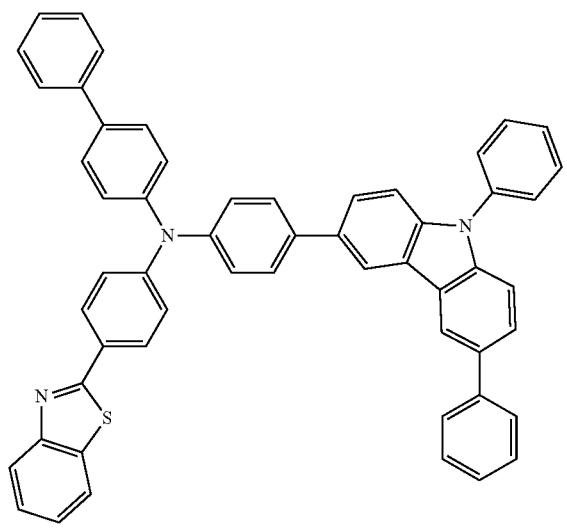
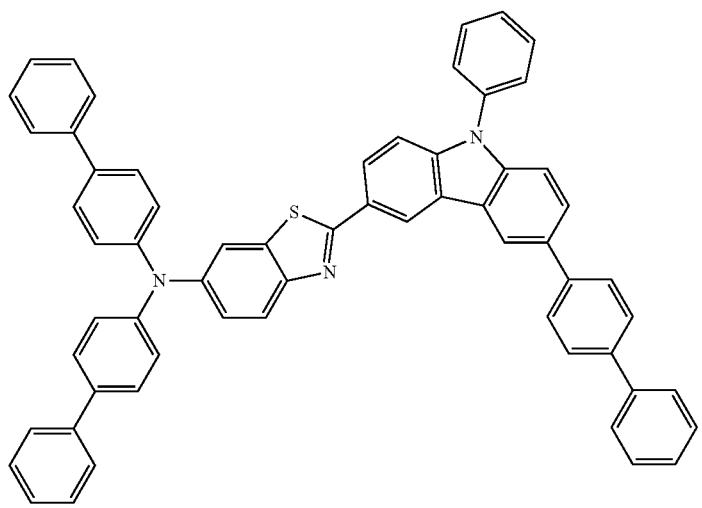

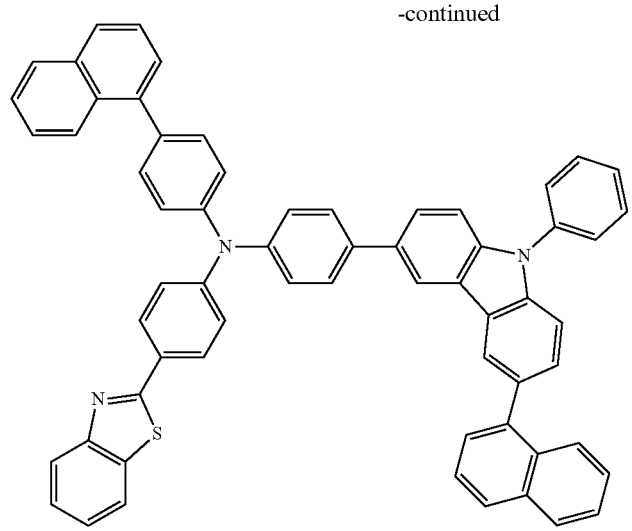
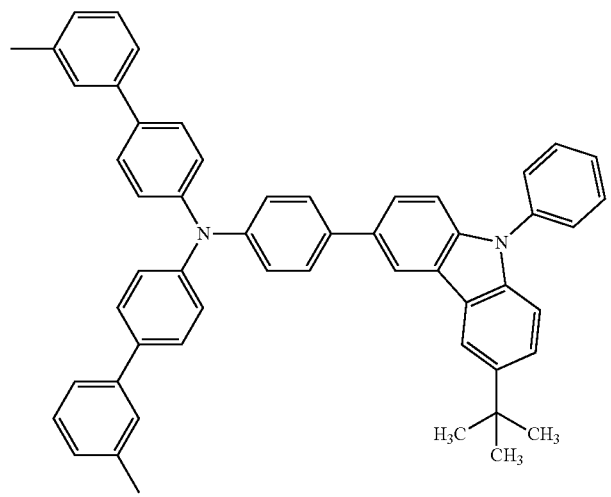
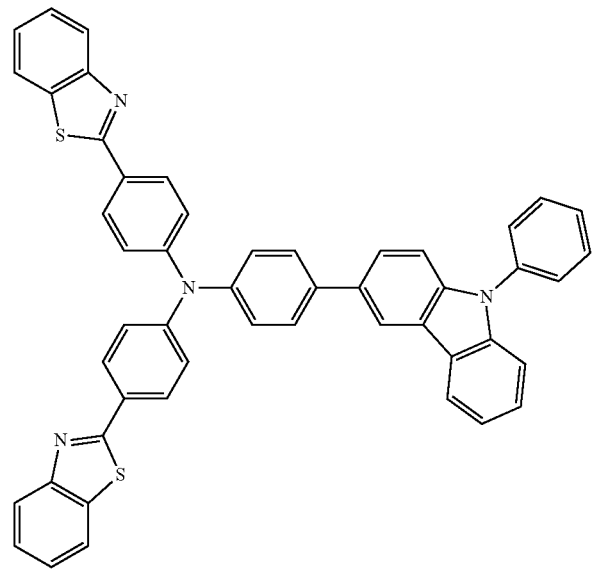

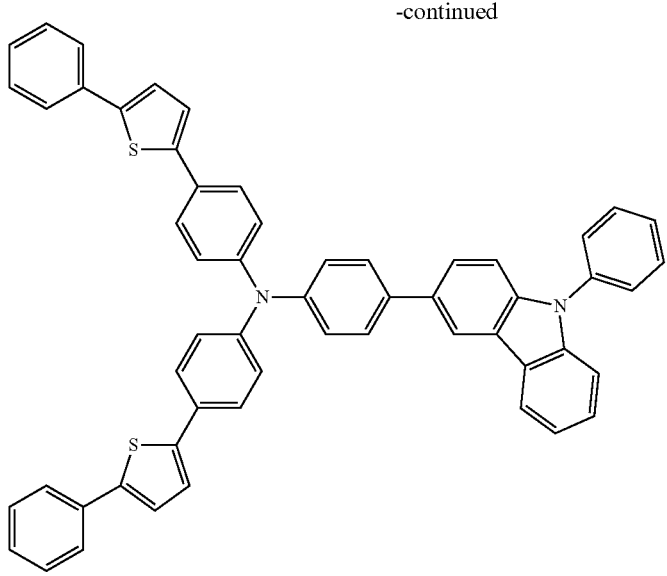
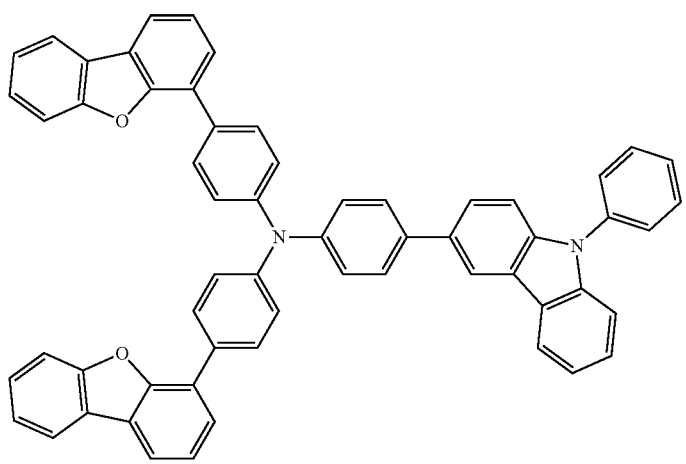
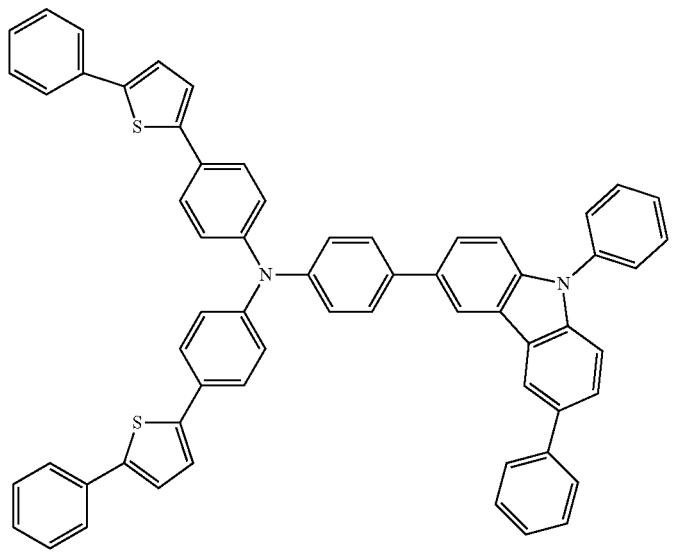

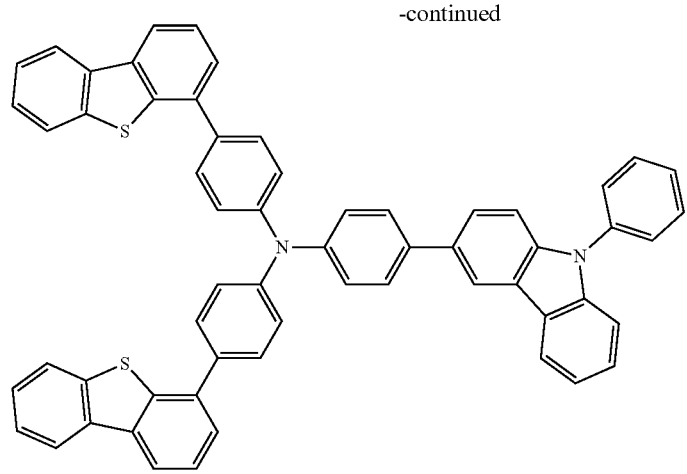
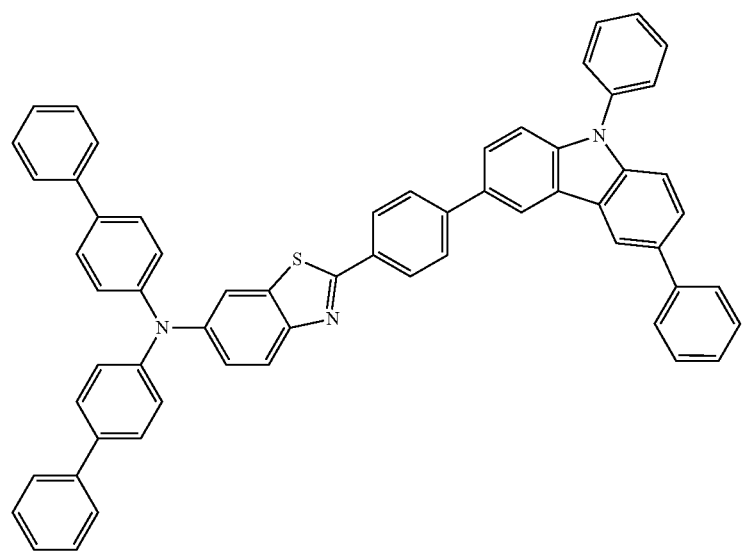
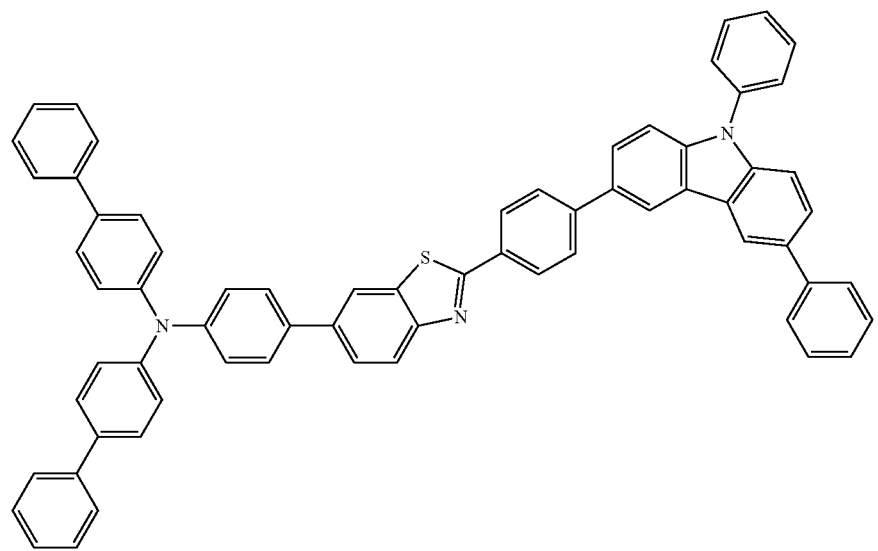

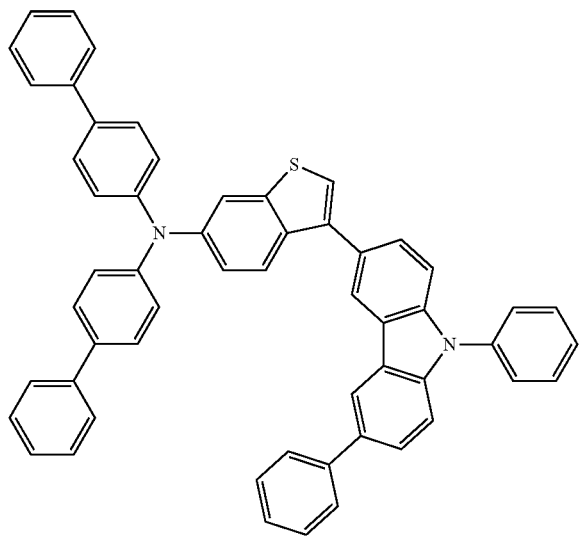
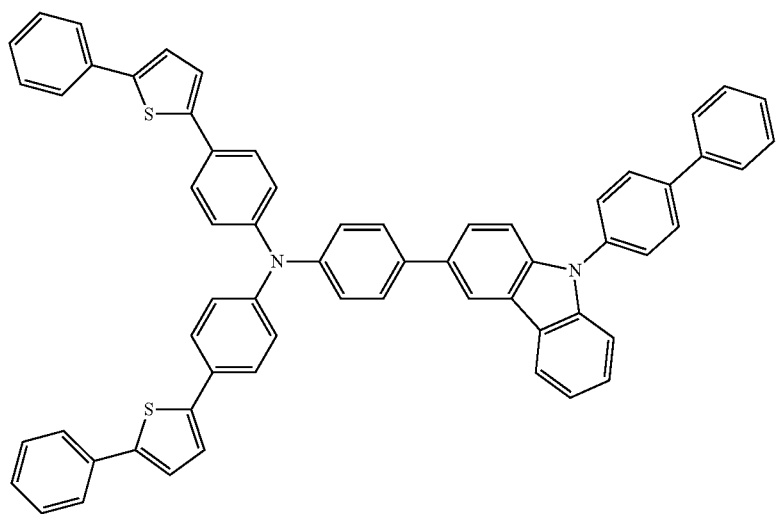
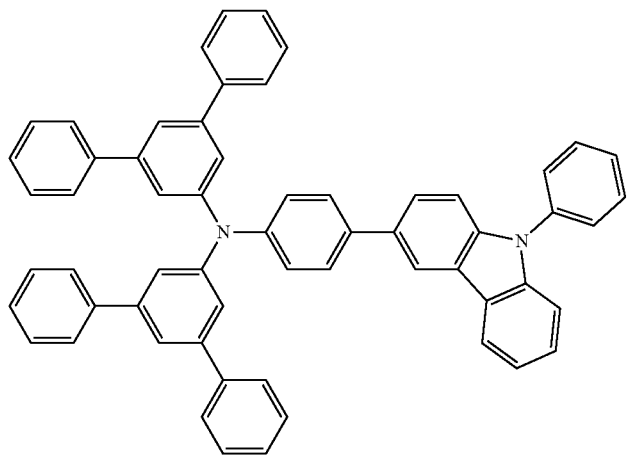

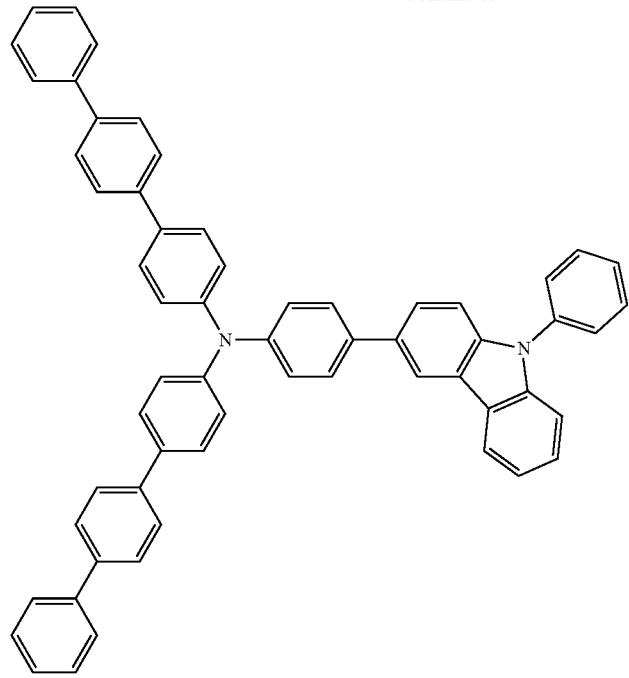
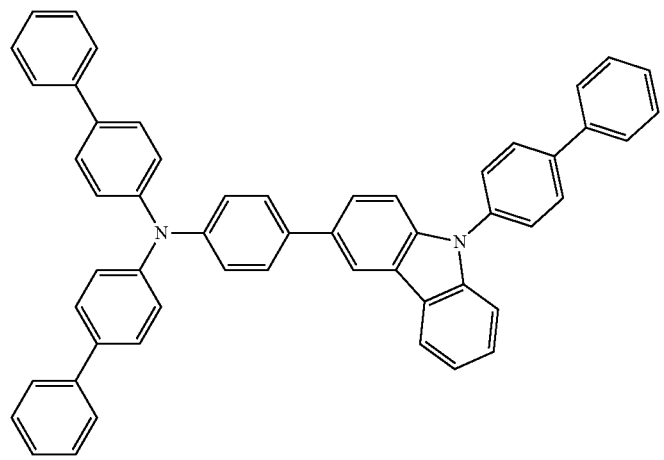
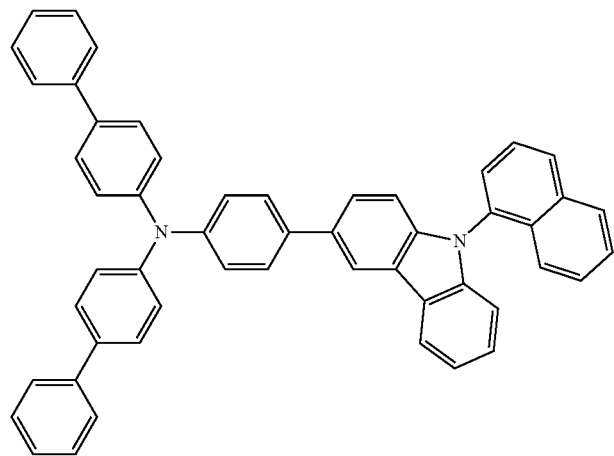

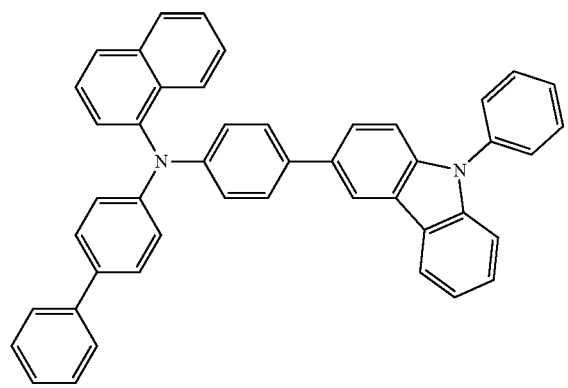

-continued

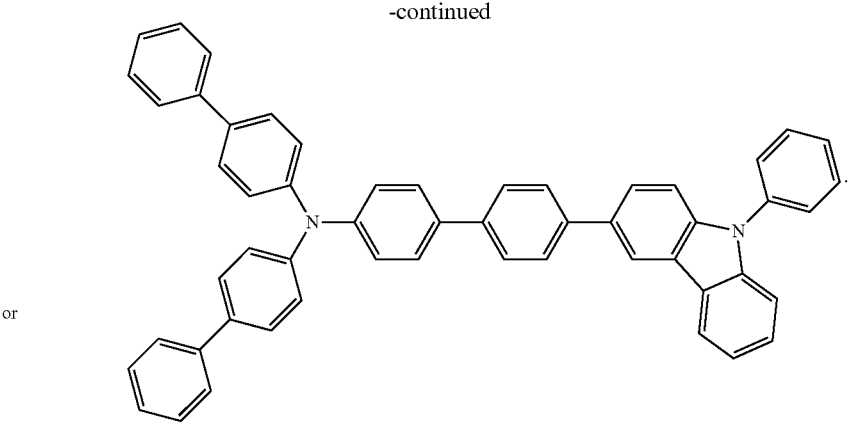

or

20. An organic electroluminescence device, comprising:
an anode, a cathode and one or more organic thin film layers between the anode and the cathode,
wherein at least one organic thin film layer is a hole transporting layer comprising at least one hole transport material of formula (2)

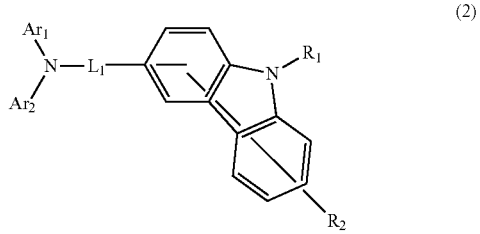

(2)

wherein $L_1$ is selected from the group consisting of a phenyl group and a biphenyl group;
$Ar_1$ and $Ar_2$ are each independently selected from the group consisting of 1-naphthyl group, 2-naphthyl group, 2-biphenyl group, 3-biphenylyl group, 4-biphenylyl group, p-terphenyl-4-yl group, p-terphenyl-3-yl group, p-terphenyl-2-yl group, m-terphenyl-4-yl group, m-terphenyl-3-yl group and a m-terphenyl-2-yl group;
$R_1$ is at least one of a phenyl group, a 2-biphenyl group and a 3-biphenyl group; and
$R_2$ is at least one of a hydrogen atom and a phenyl group.

21. An organic electroluminescence device which comprises one or more organic thin film layers including at least one light emitting layer sandwiched between a cathode and an anode, wherein the at least one light emitting layer comprises the aromatic amine derivative according to claim 1 singly or as a mixture.

* * * * *